US009228204B2

(12) United States Patent
Pulst et al.

(10) Patent No.: US 9,228,204 B2
(45) Date of Patent: Jan. 5, 2016

(54) CONSTRUCTS FOR MAKING INDUCED PLURIPOTENT STEM CELLS

(71) Applicant: University of Utah Research Foundation, Salt Lake City, UT (US)

(72) Inventors: Stefan M. Pulst, Salt Lake City, UT (US); Sharan Paul, Salt Lake City, UT (US); Warunee Dansithong, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/975,004

(22) Filed: Aug. 23, 2013

(65) Prior Publication Data

US 2014/0170752 A1 Jun. 19, 2014

Related U.S. Application Data

(63) Continuation-in-part of application No. 13/960,305, filed on Aug. 6, 2013, now abandoned, which is a continuation of application No. PCT/US2012/025117, filed on Feb. 14, 2012.

(60) Provisional application No. 61/442,695, filed on Feb. 14, 2011.

(51) Int. Cl.
*C12N 15/00* (2006.01)
*C12N 15/86* (2006.01)
*C12N 5/074* (2010.01)

(52) U.S. Cl.
CPC .............. *C12N 15/86* (2013.01); *C12N 5/0696* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2710/10343* (2013.01)

(58) Field of Classification Search
USPC ...................................................... 435/320.1
See application file for complete search history.

(56) References Cited

U.S. PATENT DOCUMENTS

| | | | |
|---|---|---|---|
| 2009/0047263 | A1 | 2/2009 | Yamanaka et al. |
| 2009/0191159 | A1 | 7/2009 | Sakurada et al. |
| 2009/0191171 | A1 | 7/2009 | Ma |
| 2009/0227032 | A1 | 9/2009 | Yamanaka et al. |
| 2009/0246875 | A1 | 10/2009 | Yamanaka et al. |
| 2009/0299763 | A1 | 12/2009 | Sakurada |
| 2009/0304646 | A1 | 12/2009 | Sakurada et al. |
| 2010/0003757 | A1 | 1/2010 | Mack et al. |
| 2010/0062534 | A1 | 3/2010 | Hochedlinger et al. |
| 2010/0075421 | A1 | 3/2010 | Yamanaka et al. |
| 2010/0105100 | A1 | 4/2010 | Sakurada et al. |
| 2010/0120069 | A1 | 5/2010 | Sakurada et al. |
| 2010/0150889 | A1 | 6/2010 | Townes et al. |
| 2010/0167291 | A1 | 7/2010 | Rosenberg et al. |
| 2010/0184051 | A1 | 7/2010 | Hochedlinger et al. |
| 2010/0279404 | A1 | 11/2010 | Yamanaka et al. |
| 2010/0311171 | A1 | 12/2010 | Nakanishi et al. |

FOREIGN PATENT DOCUMENTS

| | | |
|---|---|---|
| EP | 2263705 | 12/2010 |
| KR | 2009/0083761 | 8/2009 |
| WO | WO 2008/151058 | 12/2008 |
| WO | WO 2009/007852 | 1/2009 |
| WO | WO 2009/092042 | 7/2009 |
| WO | WO 2009/093022 | 7/2009 |
| WO | WO 2009/096614 | 8/2009 |
| WO | WO 2009/131262 | 10/2009 |
| WO | WO 2009/133971 | 11/2009 |
| WO | WO 2009/140655 | 11/2009 |
| WO | WO 2009/149233 | 12/2009 |
| WO | WO 2009/152485 | 12/2009 |
| WO | WO 2010/017562 | 2/2010 |
| WO | WO 2010/019569 | 2/2010 |
| WO | WO 2010/028019 | 3/2010 |
| WO | WO 2010/036923 | 4/2010 |

OTHER PUBLICATIONS

Takahashi (Cell, 2006, vol. 126:663-676).*
Yu (Science, 2007, vol. 318, p. 1917-1920).*
Nakagawa (Nat Biotechnol, Jan. 2008, vol. 26: 101-106; published online Nov. 11, 2007).*
Okita (Science, Nov. 7, 2008, vol. 322, p. 949-953).*
Feng (Cell Stem Cell, Apr. 3, 2009, vol. 4, p. 301-312).*
Shao (Expert Opin. Biol. Ther., Feb. 2010, vol. 10, No. 1, p. 231-242).*
Aoi (Science, Aug. 1, 2008, vol. 321, No. 5889, p. 699-702, available online Feb. 14, 2008).*
Aasen (Nature Biotech., Nov. 2008, vol. 26, No. 11, p. 1276-1284).*
Sugii (PNAS, Feb. 23, 2010, vol. 107, No. 8, p. 3558-3563).*
Stadtfeld (Cell Stem Cell, Mar. 6, 2008, vol. 2, p. 230-240; published online Feb. 14, 2008).*
Carey (PNAS, 2009, vol. 106, p. 157-162).*
Carey (Nature Methods, Jan. 2010, vol. 7, No. 1, p. 46-59).*
Sommer (Stem Cells, 2009, 27, 543-549).*
Kaji (Nature, Apr. 9, 2009, vol. 458, p. 771-776).*
Gonzalez (PNAS, Jun. 2, 2009, vol. 106, No. 22, p. 8918-8922).*
Paul, Annals of Neurol., 2012, vol. 72, Suppl. 16, pp. S103).*
Toes (PNAS, Dec. 1997, vol. 94, p. 14660-14665).*

(Continued)

*Primary Examiner* — Michael Wilson

(74) *Attorney, Agent, or Firm* — Thorpe North & Western LLP

(57) ABSTRACT

Systems, constructs, and methods for reprogramming cells are provided. In one aspect, for example, a transformation construct for generating iPS cells can include an expression vector having a plurality of reprogramming factors, each reprogramming factor being under control of a separate promoter.

12 Claims, 15 Drawing Sheets

(56) References Cited

OTHER PUBLICATIONS

Carey, et al.; "Reprogramming of murine and human somatic cells using a single polycistronic vector"; vol. 106, No. 1; Dec. 24, 2008; pp. 157-162.
Gonzalez, et al.; "Generation of mouse-induced pluripotent stem cells by transient expression of a single noviral polycistronic vector"; vol. 106; No. 22; pp. 8918-8922.
Lai, et al.; "Advancements in reprogramming strategies for the generation of induced pluripotent stem cells"; Journal of Assisted Reproduction and Genetics, Publishers-Plenum Publishers; vol. 28; No. 4, Mar. 9, 2011.
Liu, et al.; "Induced Pluripotent Stem (iPS) Cell Research Overview"; Cell Transplantation; vol. 20, No. 1; pp. 15-19, 2011.
Lowry, et al.; "The many ways to make an iPS cell"; vol. 26, No. 11, Nov. 1, 2008, Nature Biotechnology.
Montserrat, et al.; "Generation of Pig iPS Cells: A Model for Cell Therapy"; Journal of Cardiovascular Translational Research, 2011; vol. 4, No. 2, Nov. 19, 2010; pp. 121-130.
Okita, et al.; "Induced pluripotent stem cells: opportunities and challenges"; Phil. Trans. R. Soc. B 2011, 366, pp. 2198-2207.
Pourfathollah, et al.; "Generation of Induced Pluripotent Stem (IPS) Cells with Adenovectors Carrying embryonically Expressed Human Genes"; vol. 1, No. supp. 2, Nov. 19, 2011; 2 pages.
Shao, et al.; "Gene-delivery systems for IPS cell generation"; Feb. 1, 2010; pp. 1-19; PubMed Central (PMC) Author Manuscript Expert Opin. Biol. Ther.
Stadtfeld, et al.; "Induced Pluripotent Stem Cells Generated Without viral Integration"; Science, American Association for the Advancement of Science, Washington, DC; vol. 322, No. 5903, Nov. 7, 2008.
Zhou, et al.; "Adenoviral Gene Delivery Can Reprogram Human Fibroblasts to Induced Pluripotent Stem Cells"; vol. 27, No. 11, Nov. 1, 2009; pp. 2667-2674.

* cited by examiner

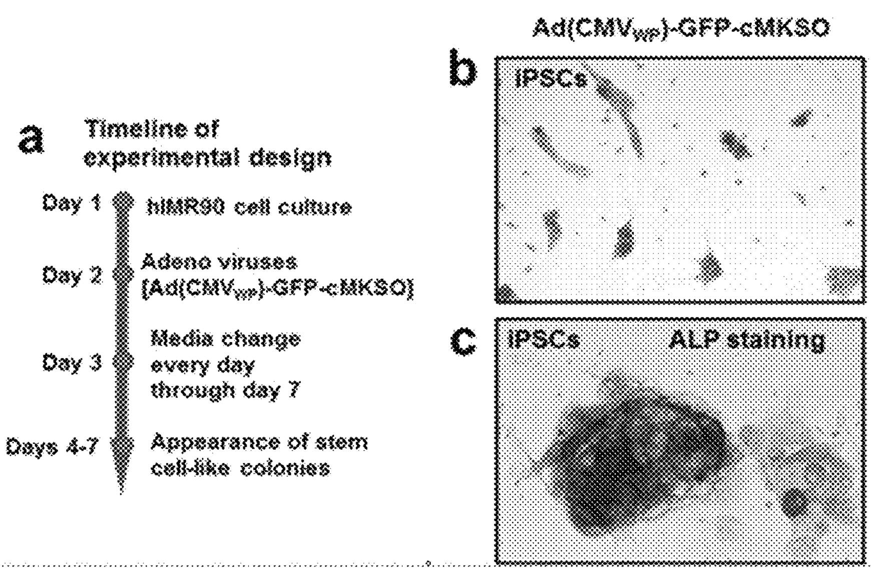
FIG. 18A-C
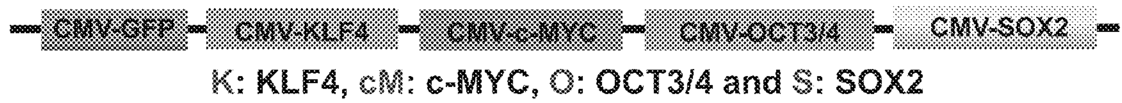
FIG. 19

CONSTRUCTS FOR MAKING INDUCED PLURIPOTENT STEM CELLS

PRIORITY DATA

This application is a continuation-in-part of U.S. patent application Ser. No. 13/960,305, filed on Aug. 6, 2013, which is a continuation of Patent Cooperation Treaty Patent Application Serial No. PCT/US2012/025117, filed on Feb. 14, 2012, which claims the benefit of U.S. Provisional Patent Application Ser. No. 61/442,695, filed on Feb. 14, 2011, all of which are incorporated herein by reference.

GOVERNMENT INTEREST

This invention was made with government support under grant numbers R01 NS033123 and NS073009 awarded by National Institutes of Health. The government has certain rights in this invention.

BACKGROUND

Current protocols for the generation of induced pluripotent stem (iPS) cells from somatic cells are slow (e.g. 30-45 days) and are inefficient (<0.1% of cells are reprogrammed). Additionally, the generation of iPS cells from somatic cells achieved by simultaneous viral transduction of defined reprogramming transcription factors using Lenti- or Retro- or Adeno-viruses requires multiple viral vectors for gene delivery. Lenti- or Retro-viruses can also result in insertional mutagenesis and can present significant barriers to research, clinical, and therapeutic application of iPS cells. A single gene delivery system does not ensure the infectivity and co-expression of all genes in one cell which is critical for reprogramming. Despite the progress in embryonic stem (ES) cells research in recent years, feeder cells such as inactivated mouse embryonic fibroblasts (iMEF) are still required to generate iPS cells from human or mouse fibroblasts. Feeder cells provide the essential support and nutrients to allow ES/iPS cells to grow, attach, and proliferate. The risk of contamination of viruses or other macromolecules from the mouse cells limits the use of such iPS cells for therapeutic purposes.

SUMMARY

The present disclosure provides systems, constructs, and methods for reprogramming cells. In one aspect, for example, a transformation construct for generating iPS cells can include an expression vector having a plurality of reprogramming factors, where each reprogramming factor is under control of a separate promoter. In one aspect, the expression vector can be selected from plasmids, viruses, and combinations thereof. In another aspect, the expression vector can be selected from adenoviral vectors, episomal vectors, retroviral vectors, and lentiviral vectors. In one specific aspect the expression vector can be an episomal vector.

Various reprogramming factors are contemplated for use in aspects of the present invention. In one aspect, for example, the plurality of reprogramming factors can include OCT3/4, SOX2, and at least one member selected from KLF4, c-Myc, NANOG, or LIN28. In another aspect, the plurality of reprogramming factors can include OCT3/4, SOX2, KLF4, and c-Myc. In yet another aspect, the plurality of reprogramming factors can consist of OCT3/4, SOX2, and KLF4. In a further aspect, the plurality of reprogramming factors includes OCT3/4, SOX2, NANOG, and LIN28. Furthermore, in one aspect, the expression vector can have a sequence that is at least 80% homologous to SEQ ID 72. In yet another aspect, the expression vector has a sequence that is at least 95% homologous to SEQ ID 72. In a further aspect, the expression vector has the sequence of SEQ ID 72.

Various promoters and/or sets of promoters are contemplated, and any appropriate promoter is considered to be within the present scope. In one aspect, for example, at least one of the reprogramming factors is under the control of a CMV promoter. In another aspect, the CMV promoter is a weak CMV promoter. Furthermore, in various aspects the expression vector can further include a reporter sequence under control of a separate promoter.

The present disclosure additionally provides methods of generating iPS cells. In one aspect such a method can include separately cloning a plurality of reprogramming factors including OCT3/4, SOX2, and at least one member selected from the group consisting of KLF4, c-Myc, NANOG, or LIN28 into separate vectors, where each reprogramming factor is controlled by a separate promoter. The method can further include consecutively cloning each of the reprogramming factors including each promoter into a single shuttle vector, linearizing the shuttle vector and recombining in bacterial cells to create an expression vector, infecting transformable cells with the expression vector, and growing the transformable cells for a period of time to generate iPS cells. In one specific aspect, the reprogramming factors can be cloned into separate vectors using blunt end ligation. In some aspects, the present method can further include generating the iPS cells in the absence of feeder cells, in the absence of a matrigel matrix, or in the absence of feeder cells and a matrigel matrix.

Furthermore, in one aspect an iPS cell is provided that is generated according to the methods and techniques of the present disclosure. In another aspect, a subsequent generation cell ultimately obtained from the iPS cell according to the present disclosure is provided. In yet another aspect, the differentiated cell derived from the iPS cell according to the present disclosure is provided. Non-limiting examples of such differentiated cell types can include endoderm, ectoderm, mesoderm, or an appropriate combination thereof. In some aspects, the differentiated cell can be a neuron.

BRIEF DESCRIPTION OF THE DRAWINGS

FIG. 18A shows the generation of iPS cells using the CMV weak promoter in accordance with another aspect of the present disclosure;

FIG. 18B shows the generation of iPS cells using the CMV weak promoter in accordance with another aspect of the present disclosure;

FIG. 18C shows the generation of iPS cells using the CMV weak promoter in accordance with another aspect of the present disclosure; and FIG. 19 shows a schematic view of an exemplary expression construct in accordance with another aspect of the present disclosure.

DETAILED DESCRIPTION

Figure 1:
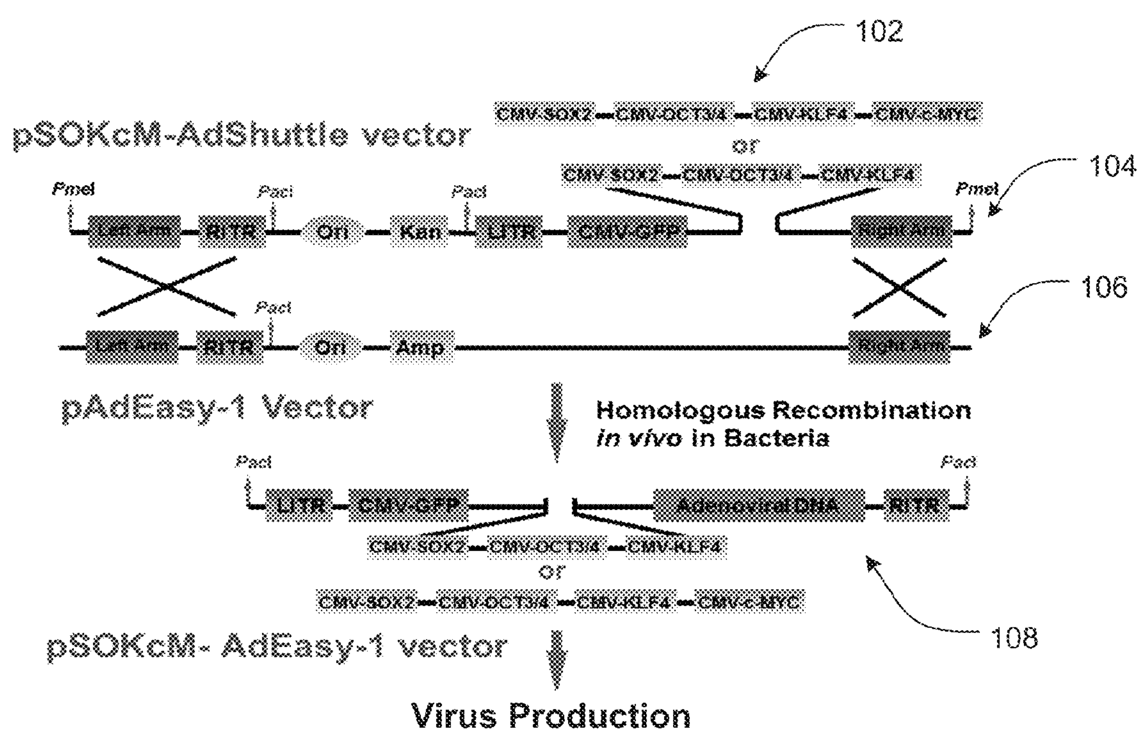
FIG. 1 is a schematic view of a vector system in accordance with one aspect of the present disclosure.

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

The following terminology will be used in accordance with the definitions set forth below.

It should be noted that, as used in this specification and the appended claims, the singular forms “a,” and, “the” include plural referents unless the context clearly dictates otherwise. Thus, for example, reference to “a cell” includes one or more of such cells and reference to “the flask” includes reference to one or more of such flasks.

As used herein, the term “substantially” refers to the complete or nearly complete extent or degree of an action, characteristic, property, state, structure, item, or result. For example, an object that is “substantially” enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of “substantially” is equally applicable when used in a negative connotation to refer to the complete or near complete lack of an action, characteristic, property, state, structure, item, or result. For example, a composition that is “substantially free of” particles would either completely lack particles, or so nearly completely lack particles that the effect would be the same as if it completely lacked particles. In other words, a composition that is “substantially free of” an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Disclosure

The inventors have developed a non-integrating vector system where multiple reprogramming factors are cloned in a single cassette in an expression vector. In some aspects, all defined reprogramming factors that are sufficient for the generation of iPS cells are cloned in a single cassette in an expression vector. Additionally, each gene corresponding to each reprogramming factor is expressed under the control of its own independent promoter that allows the balanced expression of all genes in one cell. In contrast to single expression of reprogramming factors in individual vectors, cells are reprogrammed into iPS cells in about 2-14 days with greater than about 80% efficiency without the need for feeder cells. These iPS cells show human ES cell morphology, and express ES cell surface markers and pluripotent cell-specific genes. The iPS cells can also be differentiated into cells of the three germ layers. Furthermore, iPS cells can be generated from a variety of cells, including, without limitation, human skeletal muscle cells and skin fibroblasts.

Several different standards to demonstrate pluripotency have traditionally been used. Except for the ability to generate normal embryos, iPS cells generated by the present invention in as little as 2-3 days without feeder cells meet all the reported criteria seen in iPS cells generated by other methods. Cells reprogrammed using the present techniques display features typical of human ES cells, including the presence of an unmethylated NANOG promoter, early initiation of mesenchymal to epithelial transition, expression of ES cell-marker genes and cell surface markers, as well as differentiation into germ layers in vitro and in vivo, including neurons.

Balanced expression of reprogramming factors under the control of individual promoters leads to a qualitative change in reprogramming and obviates the use of feeder cells. The short and reproducible time course of reprogramming can facilitate the study of these pathways and identify novel proteins important in the reprogramming process. This is particularly true for those proteins and lincRNAs that show overall little expression changes between the initial and final time points, but actually experience a change in between these time points. Initial pathway analysis highlights the importance of genes involved in cytokine-receptor pathways, with later upregulation of genes involved in hedgehog signaling, whereas genes involved in cell cycle and DNA replication are down-regulated at intermediate and late stages, as is described more fully herein. The more complete and coordinated activation of reprogramming pathways as a result of balanced expression of reprogramming factors can allow further detailed dissection of these pathways and their timing as well as analysis of the role of linc- and other non-coding RNAs in human reprogramming.

It should also be noted that the methods for vector construction, gene expression, generation of iPS cells, cell lines utilized, and other specific protocol details are shown as non-limiting examples in the following discussion. Furthermore, the techniques described herein can be utilized in a variety of contemplated transformation systems, and should not be seen as being limited to the iPS transformation system disclosed herein. Variation in the number of reprogramming factors included in the cassette and the specific types of reprogramming factors can vary, both within the iPS system and in other transformation systems.

A variety of promoters are contemplated, and any promoter that can be utilized as described herein is considered to be within the present scope. In some cases the selection of a given promoter or set of promoters can be a design choice that takes into account the particular expression vector utilized, any size requirements or limitations established by the promoter/vector combination, and the like. In one non-limiting aspect, however, the promoter can be a cytomegalovirus (CMV) promoter, and in some aspects a human CMV promoter. Additionally, in some aspects each reprogramming factor in the expression vector can have a separate promoter of the same promoter type, e.g. each reprogramming factor can have a separate CMV promoter. In other aspects, each reprogramming factor can have a separate promoter, but all of the promoters in the expression vector may not be of the same promoter type. Thus, in some cases different promoters can be utilized to affect the balance of expression of the reprogramming factors in a cell. In some aspects, each reprogramming factor may have a different type of promoter. It is also noted that a promoter can be modified to increase or decrease expression of a reprogramming factor if desired.

In some aspects it is contemplated that a promoter-driven reporter can be included in the cassette to, among other things, track transgene expression. Any reporter that can be loaded into the cassette with the reprogramming factors is considered to be within the present scope. In one specific example, the reporter can be a promoter driven GFP marker. Thus in some aspects a reporter can be expressed using a dedicated reporter promoter, while in other aspects a reporter can be expressed using one or more of the reprogramming factor promoters.

Furthermore, numerous expression vectors are contemplated, and any such vector that is capable of receiving and expressing multiple reprogramming factors each from dedicated promoters is considered to be within the present scope. Non-limiting examples can include adenoviral vectors, episomal vectors, retroviral vectors, lentiviral vectors, and the like.

As has been described, in one aspect the present disclosure provides a transformation construct for generating iPS cells that can include a vector backbone having a plurality of reprogramming factors, where each reprogramming factor is under control of a separate promoter. The vector backbone can be contained in a suitable delivery package such as, for example, an adenovirus particle, an episomal expression vehicle, etc.

As one specific example, and without using feeder cells and/or matrigel systems, the inventors have successfully created human induced pluripotent stem (iPS) cells from human embryonic fibroblast IMR90 cells by producing an adenoviral vector containing multi-reprogramming factors in a single cassette. It is noted that the use of IMR90 fibroblasts should not be seen as limiting, and any cell type capable of reprogramming is considered to be within the present scope. Non-limiting examples of cells and cell-types can include human fibroblasts, human fibroblasts from patients with SCA2, skeletal muscle (e.g. SKMC), and the like. Additionally, the present scope includes all fibroblast cell lines as well as other cells such as muscle and blood cells, as well as cell lines derived therefrom.

This adenoviral construct allows balanced expression of all reprogramming factors in single cell, and greatly speeds up the reprogramming efficiency of cells in a short period of time over conventional iPS cell generation methods. For example, traditional iPS cell generation methods can take about 30-45 days, whereas the present methods can generate iPS cells in 10 days or less. In one aspect, iPS cells can be generated in from about 2 to about 10 days. In another aspect, iPS cells can be generated in from about 2 to about 6 days. In yet another aspect, iPS cells can be generated in from about 2 to about 3 days. The time period for the generation of iPS cells is measured from the time of transfection with a viral cassette until the observable appearance of stem cell-like colonies.

As has been described, the current methods allow iPS cells to be generated without the use of feeder cells and/or matrigel systems. While not intending to be bound to any scientific theory, this may be due to a more rapid transformation of the cells into iPS cells. Because the multiple reprogramming factors are introduced simultaneously into recipient cells under the control of separate promoters, regardless of the expression vector utilized, this may allow a more rapid transformation into iPS cells that more quickly forms colonies of cells that have increased surface area compared to, for example, adhered fibroblasts. Such increased surface area also results in increased access to nutrients in the culture medium, thus rendering feeder cells unnecessary. Furthermore, the simultaneous or near simultaneous transformation into iPS cells may promote survival of iPS cells through secreted factors. Additionally, cells that are just about to transform into iPS cells, or that have just undergone this transition, begin to migrate towards each other to form colonies. This also suggests the presence of secretable factors to indicate location and initiate locomotion toward iPS cell colonies. Various classes of such secretable factors are contemplated, including, without limitation, peptides, proteins, lipoproteins, glycoproteins, glycolipids, and the like, and may be co-expressed with receptor molecules at the cell surface.

Numerous methods and techniques for generating an expression vector are contemplated, and can vary depending on the vector utilized, the cell system, the preferences of the technician, etc. As such, the following description is not considered to be limiting. In one aspect, reprogramming factors can be cloned separately into separate vectors, where each reprogramming factor is under the control of a separate promoter, such as, for example, a cytomegalovirus (CMV) promoter. One example of such a vector is pAdTrack-CMV. It is noted that the present scope includes any promoter that is capable of being separately associated with a set of reprogramming factors and loaded into a vector. Non-limiting examples can include the CAG-promoter, a combination of CMV early enhancer elements, chicken beta-actin promoter, and the like. Additionally, a mutated promoter, such as a mutated CMV promoter, can be utilized to alter the expression of the associated reprogramming factor.

Subsequently, multiple reprogramming factors along with the associated promoters can be consecutively subcloned into a shuttle vector. One non-limiting example can be using blunt end ligation. Any number of reprogramming factors can be subcloned into the shuttle vector. In one aspect, at least two reprogramming factors can be subcloned therein. In another aspect, at least three reprogramming factors can be subcloned therein. In another aspect, at least four reprogramming factors can be subcloned therein.

A variety of reprogramming factors and reprogramming factor combinations are contemplated, and any such factor or factor combination capable of generating iPS cells is considered to be within the present scope. Non-liming examples of reprogramming factors include OCT3/4, SOX2, KLF4, c-Myc, NANOG, LIN28, and the like, including combinations thereof. In one aspect, the reprogramming factors can include OCT3/4, SOX2 and at least one factor selected from KLF4, c-Myc, NANOG, or LIN28. In another aspect, the reprogramming factors can include OCT3/4, SOX2, and at least two factors selected from, KLF4, c-Myc, NANOG, or LIN28. In one specific aspect, the reprogramming factors include OCT3/4, SOX2, KLF4, and c-Myc. In one aspect, one example of an OCT3/4, SOX2, KLF4, and c-Myc construct is at least 80% homologous to SEQ ID 1. In another aspect, the construct can be at least 95% homologous, or 100% homologous to SEQ ID 1. Furthermore, in one aspect, the expression vector can have a sequence that is at least 80% homologous to SEQ ID 72. In yet another aspect, the expression vector has a sequence that is at least 95% homologous to SEQ ID 72. In a further aspect, the expression vector has the sequence of SEQ ID 72. In some aspects, SEQ ID 72 may be otherwise referred to as pAd-GFP-KcMOS. It should be noted that the order of the reprogramming factors as recited herein may not be limiting, but can be used in specific order when so specified. For example, pAd-GFP-KcMOS can be referred to in some aspects as pAd-SocMK. As such, the present scope includes sequences similar to SEQ ID 72 where the reprogramming factors have been inserted in a different order. A schematic representation of an exemplary expression construct pAd-GFP-KcMOS is shown in FIG. 19.

In another specific aspect, the reprogramming factors include or consist of OCT3/4, SOX2, and KLF4. In one aspect, one example of an OCT3/4, SOX2, and KLF4 construct is at least 80% homologous to SEQ ID 4. In another aspect, the construct can be at least 95% homologous, or 100% homologous to SEQ ID 4. In yet another specific aspect, the reprogramming factors include or consist of OCT3/4, SOX2, NANOG, and LIN28. In a further specific aspect, the reprogramming factors include OCT3/4, SOX2, NANOG, and LIN28. In yet another aspect, other members of the OCT, SOC, NANOG, and LIN families can be utilized.

In another aspect, at least one reprogramming factor can be selected from AIRE, CBFA2T3, CEBPE, CRABP2, EGR4, HIC2, IRX4, IRF7, KCNH2, KLF3, KLF4, KLF9, LIN28B, LHX6, LHX1, NFATC1, NFATC2, PEG3, POLR3G, PAX8, RAX2, RUNX3, SFRS17A, SOX8, TAF4B, ZNF57, and the like. In yet another aspect, at least one reprogramming factor can be selected from ETS1, FOXM1, HEY1, HOXA4, HOXA3, KLF6, KLF2, LZTS1, LBX2, MYBL1, MYBL2, MITF, POGK, RUNX1, SALL2, SOX6, SP140, SMAD6, SMAD9, TCF19, TOP2A, VGLL3, ZNF641, ZNF671, ZNF70, and the like.

Other non-limiting examples of reprogramming factors can include on or more selected from DBP, ZNF33B, CREB3L2, ZSCAN16, AHR, ZNF138, HSF4, HMX2, HEY1, ZNF192, PITX2, MAX, CIR1, PBX3, ZNF3, PRDM2, HOXC9, NFKB2, NRL, BATF3, SOX4, BARHL1, TSC22D3, MEF2D, GATAD2B, ZNF33A, KLF7, NR1D2, AHR, ZNF639, ETV6, IKZF4, NR1D2, ZNF217, HOXC8, GLIS3, HOXC6, ZNF397, ARID4A, ZNF496, MLLT10, ZFP36L1, NRL, PKNOX1, MTA3, PAX7, DMTF1, MZF1, RUNX1, HOXA2, HHEX, MLLT10, NFE2L1, PBX3, YEATS4, TAF6, SREBF2, RFX5, HCLS1, TP53, BACH1, TP53, ADNP, NFIL3, LMO4, KLF2, SCAND2, HOXA6, LMO4, SNAPC5, FOXC1, PCGF6, TAF5L, HOXB4, ETV6, HOXA4, ZNF256, ZNF449, ZNF193, RUNX1, ZBTB17, MYOG, NFIC, TBX5, HOXA5, CUX1, GLI3, CNOT7, TCF25, CNOT7, NPAT, SP4, MSC, IRF2, TBX5, RUNX1, ZBTB38, CREM, ZNF397, NR2F1, ZNF217, KLF5, RFXAP, HMGB2, CBL, ZNF93, ZSCAN12, MYST2, EGR2, SATB1, E2F1, PLAG1, PFDN1, E2F3, ZNF18, ENST00000300681, HLX, E2F2, SALL2, L3 MBTL1, RCAN1, ARNT2, RERE, GTF2I, HIF1A, RUNX1, SMAD9, ZNF211, SMAD6, HOXB7, MLL, CREB3L4, GLI2, HOXB8, TBX3, IRF9, NR2F2, CREB3L4, NCOR1, SMAD9, ARNTL, CITED2, ZNF213, CITED2, LZTR1, RFX5, MEIS1, BCL6, TAF5L, RB1, ATF6B, CBFA2T2, ZNF219, SCAND1, ZFP36L1, MYPOP, PBX2, SHOX2, TBX3, STAT2, EBF1, LZTS1, EPAS1, TCF7L2, ZNF236, DLX1, PBX1, ZNF75D, ETS2, TCF25, CSRNP2, TADA2A, ZFHX2, JUN, MMP14, ZBTB16, TFDP3, ZNF19, ZSCAN21, MYC, SOX6, GATAD1, ZFHX3, RUNX2, CREBBP, ELK1, ZNF187, HIF1A, NOBOX, ZSCAN20, ELK1, JDP2, FOXD1, HCFC1, BRD8, TCF21, SIM2, ZKSCAN4, HOXA7, ZNF174, MLLT10, ADNP, TFDP1, CREB3L2, FLI1, SMAD3, ZBTB25, TSC22D2, TCF19, TFDP1, EBF1, STAT1, ETV3, RUNX1, ZNF117, TGIF1, RXRB, USF2, PKNOX2, TFE3, ETV5, SP1, ZKSCAN3, TEAD2, RUNX2, SMAD5, ZNF71, RBPJ, ZNF85, TCF7L1, AR, CREB3L1, PBX1, UHRF1, CREBL2, NR2E3, MSRB2, NFKB1, THRA, NFATC4, NME2, ETS1, TCEAL1, KLF12, USF2, ELF2, CLOCK, NR3C1, UHRF1, ZNF45, ZKSCAN4, ZNF135, HOXB2, ARNT, NFYC, UBP1, MEIS2, GLI2, TBX2, ZFHX4, CTBP1, ZKSCAN2, KLF6, STAT5B, ZFP37, LASS2, TEAD1, NR2C2, CUX1, THRA, RUNX1T1, SP140, HMG20A, STAT3, MYBL2, ZSCAN18, MTA2, TOP2B, SCMH1, HOXB2, ZNF3, ZNF281, ZXDC, ARNTL2, EBF1, STATE, FOXO3, NR3C1, ZNF500, VAX2, MSRB2, PPARG, TCF4, CTBP1, HOXB3, DMTF1, SOX13, TADA3, HDAC1, ZKSCAN5, HOXB5, TARDBP, ZNF91, FOXC2, ZNF498, PTTG1, SUPT6H, GLI2, YY1, TAF12, FUBP1, STAT3, CREB1, ZEB2, ZNF175, PURA, CREM, ZNF268, ZNF132, SLC2A4RG, POU6F1, SMAD2, ZNF70, FOXO3, ATF1, RELA, TOP2A, TCF12, SP140, FUBP1, ZEB2, MSL3, BLZF1, MECOM, NFIC, PRRX1, KLF6, FOXM1, RELA, EGR1, CLOCK, ZNF202, TSHZ3, BACH1, PPARG, ZNF189, ZNF45, PHTF1, GTF2H4, PHTF1, SRF, FOXL1, ATF2, HOPX, NR2C1, ZNF69, SIX4, ELK3, ZNF167, MECOM, HMGB1, NFYB, ZNF148, ZEB1, RFXANK, PCGF2, STRN3, HOMEZ, ZNF498, NFAT5, SATB2, CTNNB1, ADNP2, TCF7L2, HOXB6, HIC1, ATF2, ZHX3, MTA1, GTF21RD1, CTNNB1, E2F7, TRERF1, FOXF2, TFCP2, HDX, PITX1, ZNF207, E2F7, PRDM2, LCOR, PITX1, ZNF155, CUX1, FOXO3, MEF2C, TFE3, ZEB1, ZNF197, and the like.

Furthermore, additional non-limiting examples of reprogramming factors can include on or more selected from SLC30A9, ZFP36L2, ELK4, ZHX3, TCFL5, GABPB1, NKX3-1, BLZF1, BLZF1, ZSCAN2, ZNF134, AFF1, NFYA, NCOR1, TRPS1, PLAGL2, PURB, GTF2H3, TAF7, CBFB, TRPS1, ATF6, ZSCAN30, FOXN2, CTCF, CREB3, SOX9, SIX1, E2F3, BHLHE41, FOSL1, TEAD3, ZHX3, TWIST1, BUD31, AFF1, NPAS1, TFCP2, TAF1B, TFEB, AFF4, ZNF174, ETV1, ZSCAN30, ZNF35, SOX5, ETV1, NFYC, ETV1, TRIM22, NFE2L3, TSHZ1, ZNF83, ENO1, AFF4, FOXN2, TCF7L2, SMAD4, BNC1, ETV1, FOS, GAS7, TRIM28, NCOR1, ZSCAN22, ELK4, SALL1, GATAD2A, DRAP1, TFAM, MEIS3, NFIX, MSX2, SMAD1, EGR3, POU2F2, GABPB1, ELF1, NFYC, IRF3, ZNF215, MAFK, ENST00000445531, KLF10, BHLHE40, TFAM, TSC22D1, MEF2B, CSRNP1, HR, CSRNP1, JUND, TARDBP, RARG, ATF5, TCF3, BCL3, PRDM1, ELF1, JUNB, GCFC1, MAFF, TULP4, USF1, IRF1, RBCK1, NOTCH1, AHCTF1, ZNF134, PPARD, ZNF274, TGIF2, UBN1, PRDM1, KLF3, MEF2B, ZNF444, DRGX, RAX2, MNT, PPARA, ZNF41, ZNF215, HMGA1, ZNF169, RBCK1, ZNF169, MBD1, MYCL1, TARDBP, C2orf3, ZNF81, FOXO4, MAX, MYNN, PLAGL2, FOSB, MSX1, KLF16, ZNF197, SOLH, ELF4, ZHX1, NFIA, IRF3, GCFC1, TEAD4, ZHX2, TFEB, E2F5, NKX1-1, AATF, GATA2, HNRNPAB, NFATC2, ZNF92, MAX, ZNF628, KLF4, RXRA, ZNF232, CSDA, PA2G4, YBX1, XBP1, MLL, NPAS2, SCML2, CSDA, SOX13, MYOD1, PPARD, NOTCH1, CNBP, TFIP11, IRF7, ZSCAN29, NKX2-3, ZNF24, HNF1B, C11orf9, FBXW7, MEF2D, REXO4, NFATC3, SOX8, ZNF207, SPEN, MGA, SNAPC4, ZRANB2, PA2G4, AHCTF1, MNT, ARID3A, RNF4, ERF, ETV4, DLX2, KLF9, ESRRA, YBX1, GATAD2A, ESRRA, TP73, KLF17, NKX6-3, MXD1, NFYC, HOXA9, TBP, TP73, HSF1, MBD1, TSC22D4, CEBPB, MTF1, RARA, BTAF1, MBD1, TLX2, TAF13, MRRF, CITED1, NFATC1, MLL, FOXL2, LASS5, NR1H3, NFATC1, LEF1, ZNF81, POU3F1, MXD1, PAX8, NOLC1, MGA, TBX1, SCML1, GABPA, NR1D1, MEF2A, POU2F1, HMBOX1, MAFG, HMX1, ZGPAT, IRX4, MBD1, MAFG, GRHL2, SPDEF, ATF3, PRRX2, NR1H2, E2F6, MAFB, MRRF, KLF11, HR, HEYL, CNBP, SNAPC2, MLX, FOXA3, ATF3, PITX3, ZNF24, ZSCANSA, AEBP1, E2F6, ZNF37A, LHX1, E2F6, HMBOX1, ETV2, FOXK2, ATF3, MAFB, RUNX3, ZGLP1, FOXK2, ZNF394, SPIB, ETV2, ZNF394, VDR, HMBOX1, HMG20B, LASS6, MYNN, ZGLP1, FOXK2, NR6A1, ARGFX, HIRA, CDX1, KLF1, ESR1, EN2, ZKSCAN1, HMG20B, TCF15, TPRX1, HMG20B, RARA, NFYA, ZNF263, RORA, PURB, TAF5, GSX1, HNF1A, UNCX, SEBOX, LASS6, FOXE3, IRX2, BATF2, DUXA, MAF, E2F4, MLL, ZNF148, MAFA, ZNF165, SIX2, LHX6, ECSIT, DUX4, HES6, TAF4, TFAP2E, SIX3, NR4A2, RELB, IRX2, LHX3, NFE2, NR4A2, MLL4, HOXA10, SPEN, E4F1, NKX1-2, SREBF1, NKX2-5, HES6, ZNF169, CCRN4L, RFX3, TBX19, RBCK1, FOXH1, HOXB9, HES6, MESP1, LBX1, STAT4, DUX4, NFX1, NR2F6, HES6, HES1, HMX1, PPARA, ZNF445, DUX4L4, SOX11, EVX1, PBX4, ZXDC, ZNF131, LMO1, ZNF3, KDM5B, STATSA, DUX4, PHFSA, REL, ZNF446, MLL4, ZNF157, IRF5, HOXA9, TAF10, HSF1, ZNF133, TRERF1, NR113, ISL2, LMX1B, SIM1, SCAND2, MYNN, ARX, TBX6, VSX1, TBX10, NR5A2, GATA6, PAX6, TFDP2, KDM5B, SNAPC5, HAND1, PAX4, DUX4, NFX1, ZNF277, SNAPC5, ZBTB48, POU5F1, ESRRG, HOXD9, CBFA2T2, FOXD2, TEF, PHF1, DDIT3, SUPT4H1, LASS3, ZNF33A, RORB, POU5F1, DMRT1, HINFP, EDF1, CDX1, ATF4, ZNF323, CNOT8, POU4F2, VPS72, FOSL2, ATF3, NFXL1, ZIC1, SPI1, CREB5, CEBPD, C5orf41, HSF1, DUX4, ZNF33A, NEUROG3, TRIM25, SREBF1, GCM1, EMX1, LASS4, PRDM2, HMX3, ONECUT2, SIX5, HOPX, ESRRB, HSF2, HOXC4, PROP1, ZNF33A, ZSCAN2, SHOX, HOXA3, NR4A3, MESP2, and the like.

Additionally, it should be noted that any one or more of the above reprogramming factors can be utilized with any other reprogramming factor described herein or in any combination with any other reprogramming factor described herein.

Turning now to FIG. 1, a schematic outline of one non-limiting example of an expression system (e.g. AdEasy-1) is provided. Reprogramming factors of interest, such as, and without limitation, OCT3/4, SOX2, KLF4, and c-Myc, can be first cloned separately into a vector under separate promoters 102 (e.g. pAdTrack-CMV). Then, each reprogramming factor along with the promoter can be consecutively subcloned into a shuttle vector 104 (e.g. pAdTrack) using a technique such as, for example, blunt end ligation. The resultant plasmid can be linearized by digesting with a restriction endonuclease such as PmeI, and recombination can be carried out using high competence bacterial cells, such as *E. coli* BJ5183 cells, by homologous recombination. In some cases, high competence bacterial cells can allow for more efficient recombination. In cases where an adenoviral vector is to be used, the recombinant adenoviral plasmid 106 (e.g. pSOKcM-AdEasy-1) can then be linearized 108 with an enzyme such as Pad and transfected into an adenovirus packaging cell line for virus production. One non-limiting example of such a cell line is HEK 293A. The "left arm" and "right arm" shown in FIG. 1 represent the regions mediating homologous recombination between the shuttle vector 104 and the adenoviral backbone vector 106. The recombination can be confirmed by multiple restriction endonuclease analyses, and the production of recombinant adenoviruses can be followed by GFP expression.

Figure 2A:
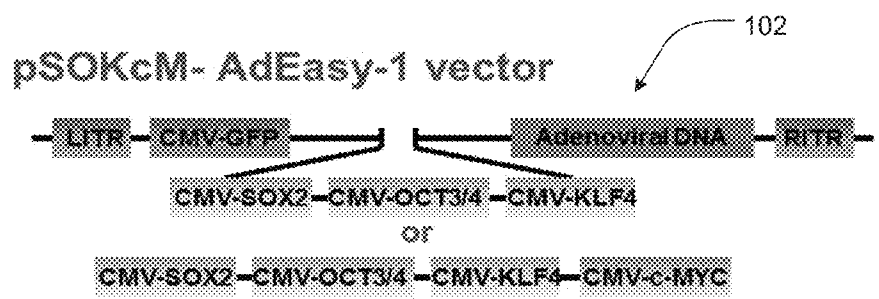
FIG. 2A is a schematic view of a vector system in accordance with another aspect of the present disclosure.
Figure 2B:
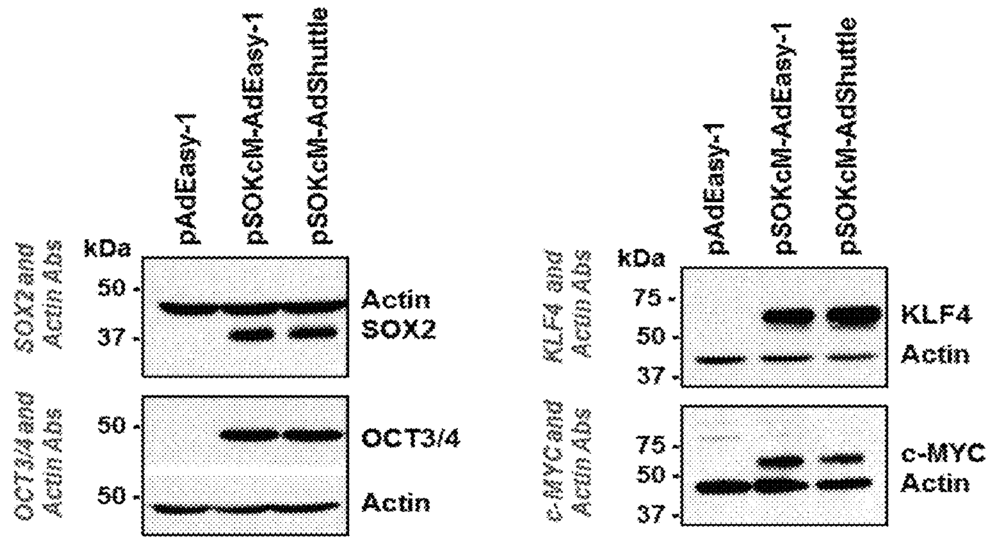
FIG. 2B shows data demonstrating protein expression of multiple reprogramming factors in accordance with another aspect of the present disclosure.
Figure 3A:
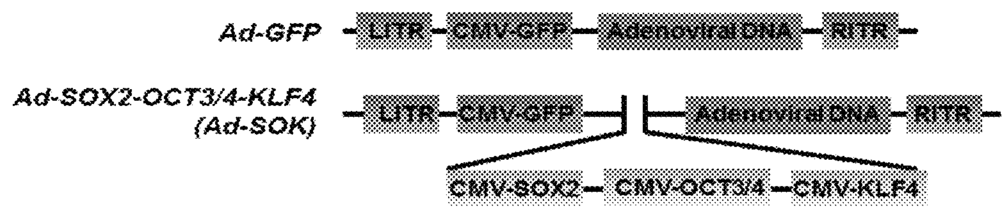
FIG. 3A is a schematic view of an adenoviral construct in accordance with yet another aspect of the present disclosure.
Figure 3B:
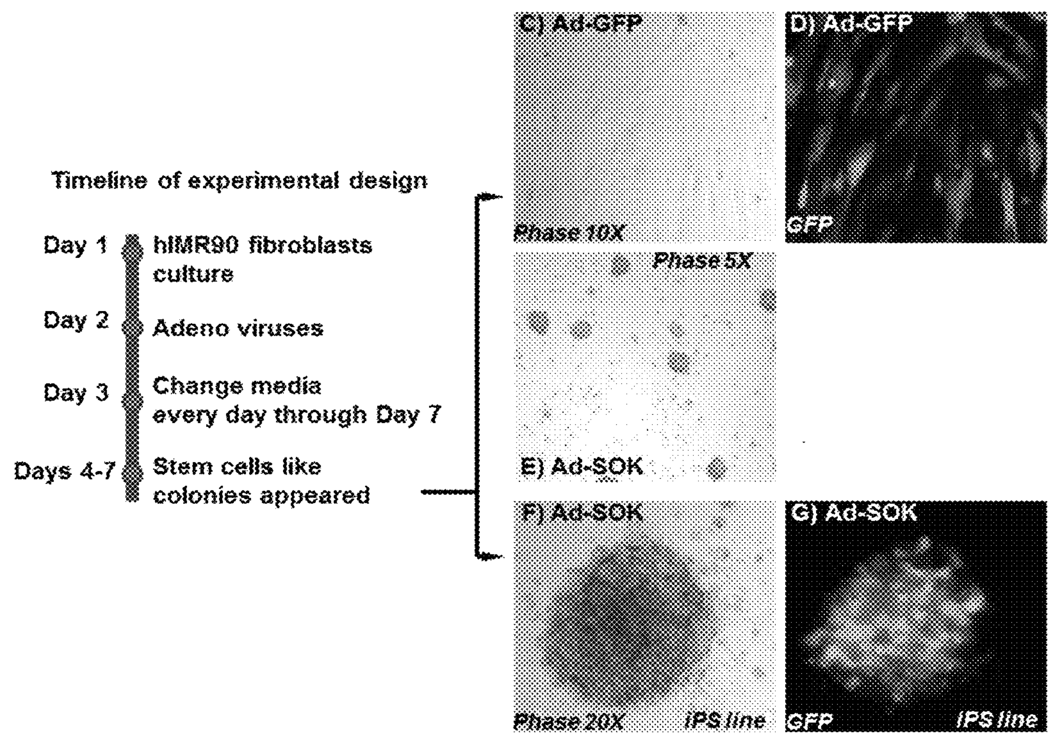
FIG. 3B shows iPS cells generated with adenoviral constructs without feeder cells, IMR90 cells transduced with Ad-GFP, and iPS cell colonies in IMR90 cells transduced with Ad-SOK in accordance with another aspect of the present disclosure.

Validation of protein expression can be accomplished using any of a number of known methods, such as western blotting, and the like. As one example, FIG. 2A shows a schematic representation of an adenoviral vector containing multi-reprogramming factors in a single cassette, pSOKcM-AdEAsy-1 102. FIG. 2B shows SH5Y cells that were transiently transfected with pSOKcM-AdEasy-1 and pSOKcM-AdShuttle constructs. Protein extracts from harvested cells at 40-54 hrs post-transfection were probed by Western blot analysis using the antibodies indicated. Blots were re-probed for Actin as an internal loading control. These results indicate that the recombinant adenoviral construct expresses all proteins from the adenoviral vector in cells tested.

iPS cells can thus be generated using an expression vector containing multi-reprogramming factors. iPS cells can be generated from a variety of transfectable cell types, and any type of cell capable of transfection is considered to be within the present scope. One specific example of such a transfectable cell type includes IMR90 human fetal fibroblasts. As is shown in FIG. 3, iPS cells can be generated with an adenoviral vector without feeder cells or a matrigel matrix. In FIG. 3A, adenoviral constructs (AdEasy-1): Ad-GFP or Ad-SOK are shown. In FIG. 3B a timeline of experimental design is shown. IMR90 cells were transduced with adenoviruses, Ad-GFP or Ad-SOK on day 2. Culture medium was changed every day with regular cell culture medium. Colonies appeared at days 4-7 in culture dishes. The top of FIG. 3B shows photomicrographs of IMR90 cells transduced with Ad-GFP on day 7; phase contrast in the top left image and GFP expression in the top right image. FIG. 3B middle and bottom images show iPS cell-like colonies appearing in IMR90 cells transduced with Ad-SOK on days 4-7, as shown by phase contrast (FIG. 3B middle and bottom left). GFP expression in fluorescence microscopy of the same colony is shown in FIG. 3B bottom right. Thus by days 4-7, several colonies showing ES cell-like morphology emerged and all colonies looked identical. The resultant colonies (iPS cells) can be further expanded or subjected to characterization.

Figure 4A:
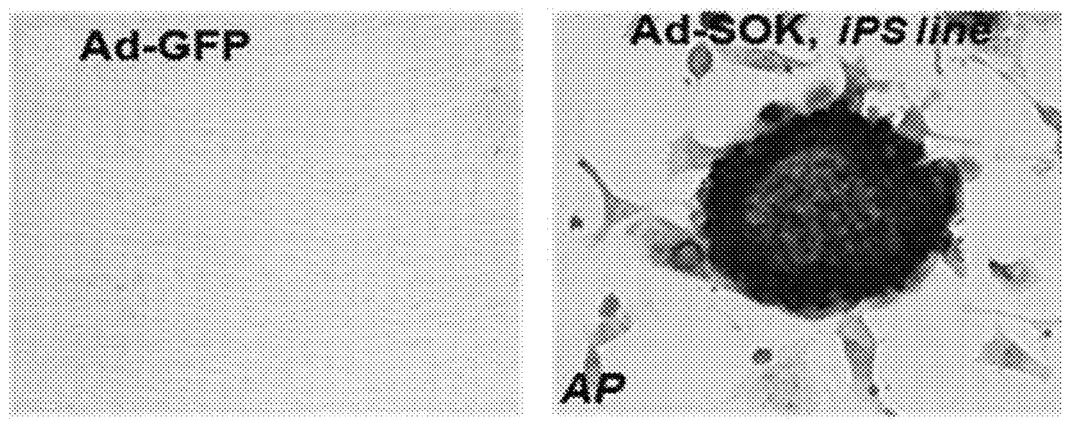
FIG. 4A shows IMR90 cells transduced with adenoviruses, either Ad-GFP (a) or Ad-SOK (b) in accordance with a further aspect of the present disclosure.
Figure 4B:
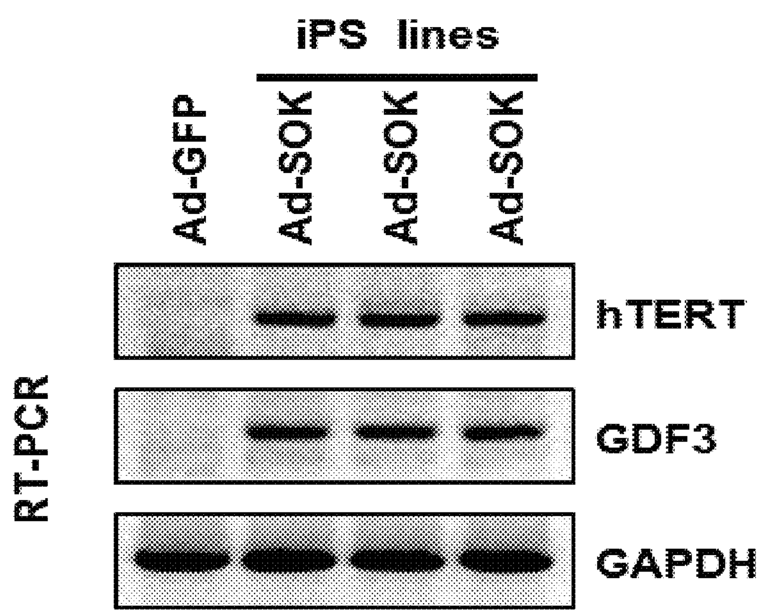
FIG. 4B shows RT-PCR data of EX cell marker genesin accordance with yet a further aspect of the present disclosure.

Following generation, iPS cells can be further characterized. The undifferentiated state of human ES cells/iPS cells express high levels of membrane alkaline phosphatase (AP), and AP staining can be used to characterize such stem cells. For AP staining, iPS cells are generated from iMR90 cells in 24 well plates using the methods as described. At day 7, iPS cells are fixed with 4% paraformaldehyde for 2 minutes, followed by 15-minute incubation with staining solution (Alkaline Phosphatase Detection Kit; Millipore). AP staining data demonstrate the positive staining for iPS cells, as shown in FIG. 4A. In this case, IMR90 cells are transduced with adenoviruses, Ad-GFP or Ad-SOK for 7 days. Human iPS cells generated from Ad-SOK are positive for alkaline phosphatase (AP) staining. FIG. 4B shows RT-PCR analyses of ES cell marker genes, IMR90 cells are transduced with adenoviruses. Ad-GFP or Ad-SOK for 7 days. Total RNA is isolated from harvested cells and synthesized cDNAs (150 ng) are used for RT-PCR analyses. Human iPS cells express many undifferentiated ES cell marker genes including telomerase reverse transcriptase (hTERT) and growth and differentiation factor 3 (GDF3). FIG. 4B shows an expression profile by RT-PCR analyses, demonstrating that iPS cells derived from IMR90 cells highly express the hTERT and GDF3 genes.

Figure 5A:
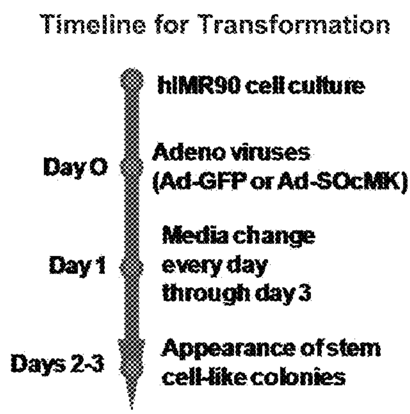
FIG. 5A shows a timeline for transformation in accordance with another aspect of the present disclosure.
Figure 5B:
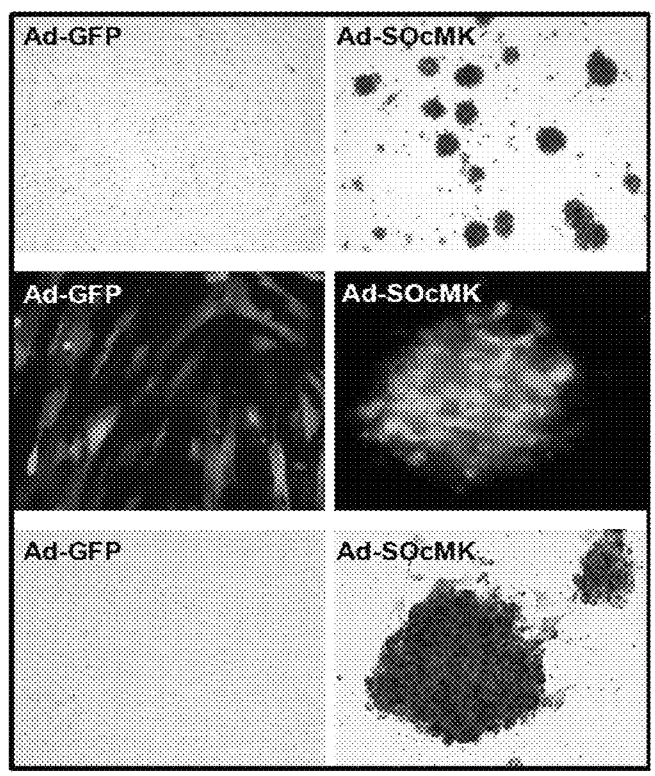
FIG. 5B shows cells tested for ALP staining in accordance with another aspect of the present disclosure.
Figure 5C:
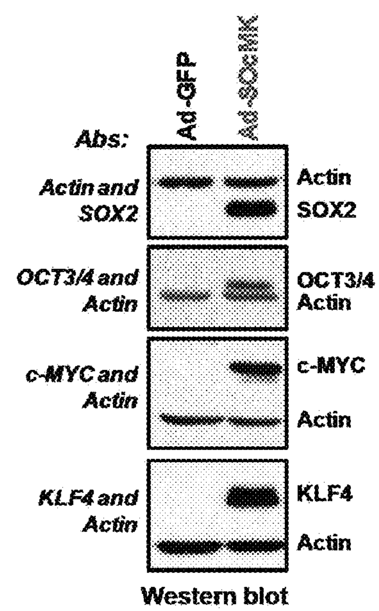
FIG. 5C shows a Western blot analyses in accordance with another aspect of the present disclosure.

In another aspect of the present disclosure, somatic cell reprogramming was tested using the adenovirus containing OCT3/4, SOX2, KLF4, and c-Myc (Ad-SOcMK) shown in FIG. 1. IMR90 cells were transduced with the adenovirus, and the timeline for transformation is shown in FIG. 5A. Briefly, the IMR90 cells were transduced with Ad-SOcMK or Ad-GFP for 12 or 21 hrs, after which the medium was replaced with human ES cell medium. Within 1 day, Ad-SOcMK-transduced cells took on a different appearance and began to form small cell clusters. By day 2 or 3, several colonies of cells showing ES cell-like morphology emerged in the dish (FIG. 1B, top right and middle right). Cells were also tested for ALP staining, as is shown in FIG. 5B, bottom right. The ALP assay reveals strong staining of IMR90-derived iPS cells indicating pluripotency, while no ALP staining is observed in the GFP-transduced cells (FIG. 5B, lower left). The expression of exogenous individual protein factors in protein extracts from harvested cells was also investigated by Western blot analyses, as is shown in FIG. 5C. The results demonstrate that all RFs in the adenovirus are highly expressed in transduced IMR90 cells but not in Ad-GFP-transduced cells.

Gene expression changes during the reprogramming process have traditionally been difficult to study. One reason for this difficulty in human cells may be due to the fact that currently known methods of reprogramming occur at low frequency and take such long periods of time to occur. This is particularly true for a new class of regulatory RNAs, called long inter-spersed non-coding (line) RNAs. The short and synchronized reprogramming process of the present disclosure can facilitate the study of global transcription changes. To pursue these issues, the inventors have studied global gene expression changes during reprogramming to determine the correlation between gene expression changes and reprogramming. Using singular value decomposition, for example, regulated functional pathways in early and intermediate stages of reprogramming of human cells have been identified, including a set of novel lincRNAs.

Figure 6A:
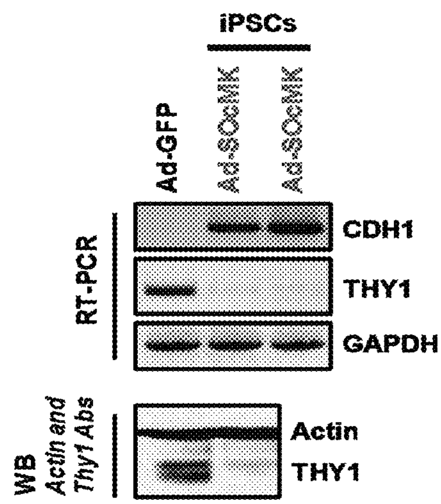
FIG. 6A shows real-time PCR and Western blot data in accordance with another aspect of the present disclosure.
Figure 6B:
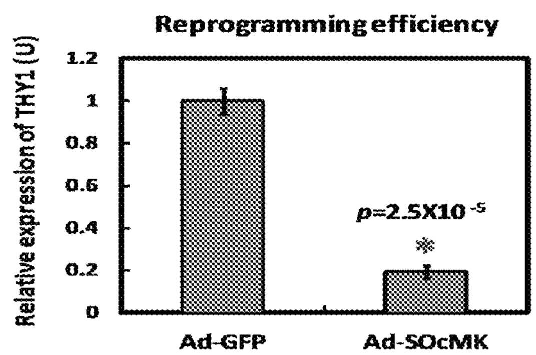
FIG. 6B shows real-time PCR and Western blot data in accordance with another aspect of the present disclosure.

Without intending to be bound to any scientific theory, mesenchymal-to-epithelial transition (MET) is a key regulatory event during reprogramming of somatic cells to the pluripotent state. Expression of exogenous reprogramming factors effectively activate the epithelial program and shut down key mesenchymal genes to favor the MET transition of somatic cells toward induced pluripotency. These events are associated with depletion of the mesenchymal marker THY1, and upregulation of the epithelial marker CDH122-24. To investigate this, the steady-state levels of THY1 and CDH1 in iPS cells generated with Ad-SOcMK are measured, RT PCR and Western blot analyses reveals upregulation of CDH1 and concomitant reduction of THY1 in iPSCs when compared with control (See FIG. 6A). As THY1 is exclusively expressed in fibroblasts and fibroblast cells dramatically switched the state in a short period of time, the expression level of THY1 by real-time PCR can be determined as a function of reprogramming efficiency, Real-time PCR and Western blot data reveals a decrease in levels of THY1 by ~80% in Ad-SOcMK transduced cells as cells are reprogrammed (See FIG. 6A lower panel, and FIG. 6B).

Figure 7A:
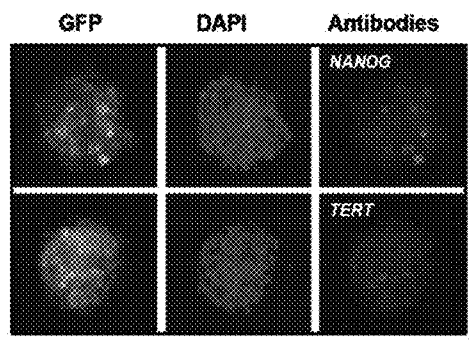
FIG. 7A shows data demonstrating expression of markers in iPS cells in accordance with another aspect of the present disclosure.
Figure 7B:
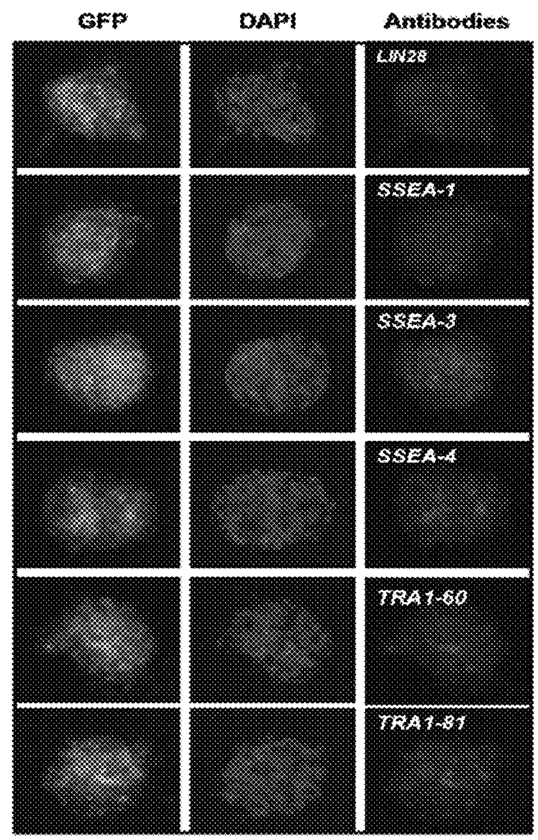
FIG. 7B shows data demonstrating expression of markers in iPS cells in accordance with another aspect of the present disclosure.

It was next examined whether iPS cells generated with Ad-SOcMK express human ES cell-marker genes such as NANOG, Telomerase reverse transcriptase (TERT), LIN28, stage specific embryonic antigens (SSEA-1, -3, and -4), and tumor-related antigens (TRA1-60 and -81). Expression of each marker in iPS cells was studied by immunofluorescence using antibodies against endogenous proteins (FIGS. 7A-B). The corresponding secondary antibodies were conjugated with Dylight variants. Immunostaining data revealed expression of ES cell markers in iPS cells generated with Ad-SOcMK from IMR90 cells.

Figure 8A:
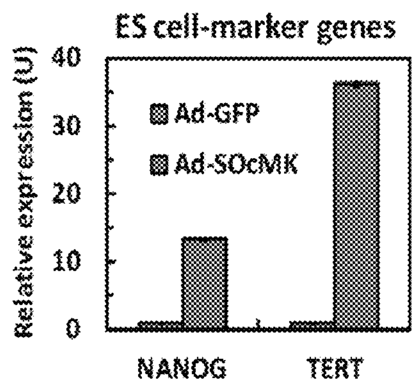
FIG. 8A shows data representing isolated RNA from iPS cells that demonstrate high expression of undifferentiated ES cell-marker genes in accordance with another aspect of the present disclosure.
Figure 8B:
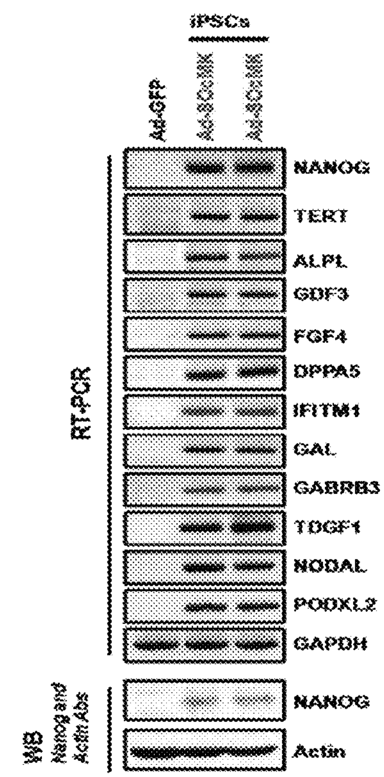
FIG. 8B shows data representing isolated RNA from iPS cells that demonstrate high expression of undifferentiated ES cell-marker genes in accordance with another aspect of the present disclosure.
Figure 8C:
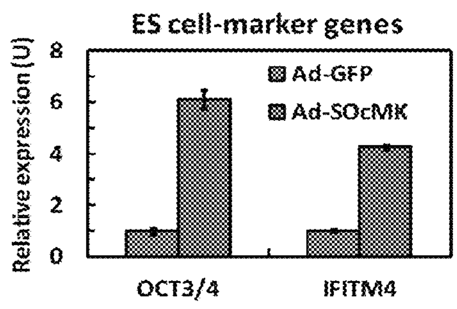
FIG. 8C shows data representing isolated RNA from iPS cells that demonstrate high expression of undifferentiated ES cell-marker genes in accordance with another aspect of the present disclosure.
Figure 8D:
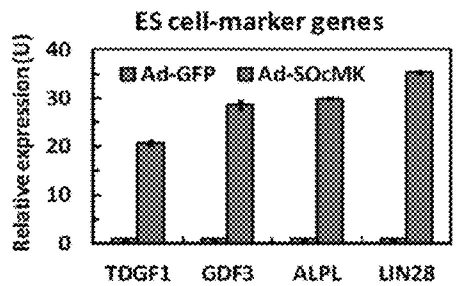
FIG. 8D shows data representing isolated RNA from iPS cells that demonstrate high expression of undifferentiated ES cell-marker genes in accordance with another aspect of the present disclosure.
Figure 8E:
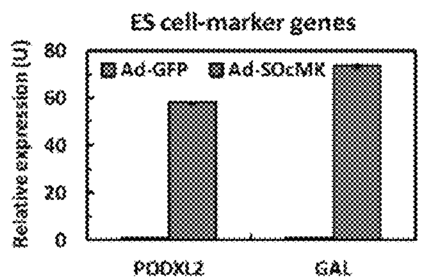
FIG. 8E shows data representing isolated RNA from iPS cells that demonstrate high expression of undifferentiated ES cell-marker genes in accordance with another aspect of the present disclosure.
Figure 8F:
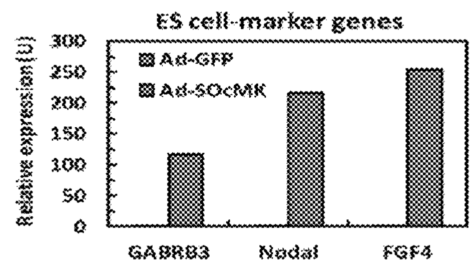
FIG. 8F shows data representing isolated RNA from iPS cells that demonstrate high expression of undifferentiated ES cell-marker genes in accordance with another aspect of the present disclosure.

To measure steady state levels of undifferentiated ES cell-marker genes, real-time RT-PCR, semi-quantitative PCR, and Western blot analyses can be performed. Real-time and semi-quantitative PCR analysis of isolated RNA from iPS cells demonstrate high expression of undifferentiated ES cell-marker genes, including NANOG, TERT, L1N28, ALPL, growth and differentiation factor 3 (GDF3), fibroblast growth factor 4 (FGF4), developmental pluripotency-associated 5 (DPPA5), interferon induced transmembrane protein 1 (IFITM1), galanin prepropeptide (GAL), gamma-aminobutyric acid (GABA) A receptor, beta 3 (GABRB3), teratocarcinoma-derived growth factor 1 (TDGF1), Nodal homolog (NODAL) and podocalyxin-like 2 (PODXL2) (See FIGS. 8A-F). Western blot analyses in protein extracts from harvested iPS cells confirmed protein expression of NANOG in iPS cells generated with Ad-SOcMK (FIG. 8B, bottom panel).

Figure 9:
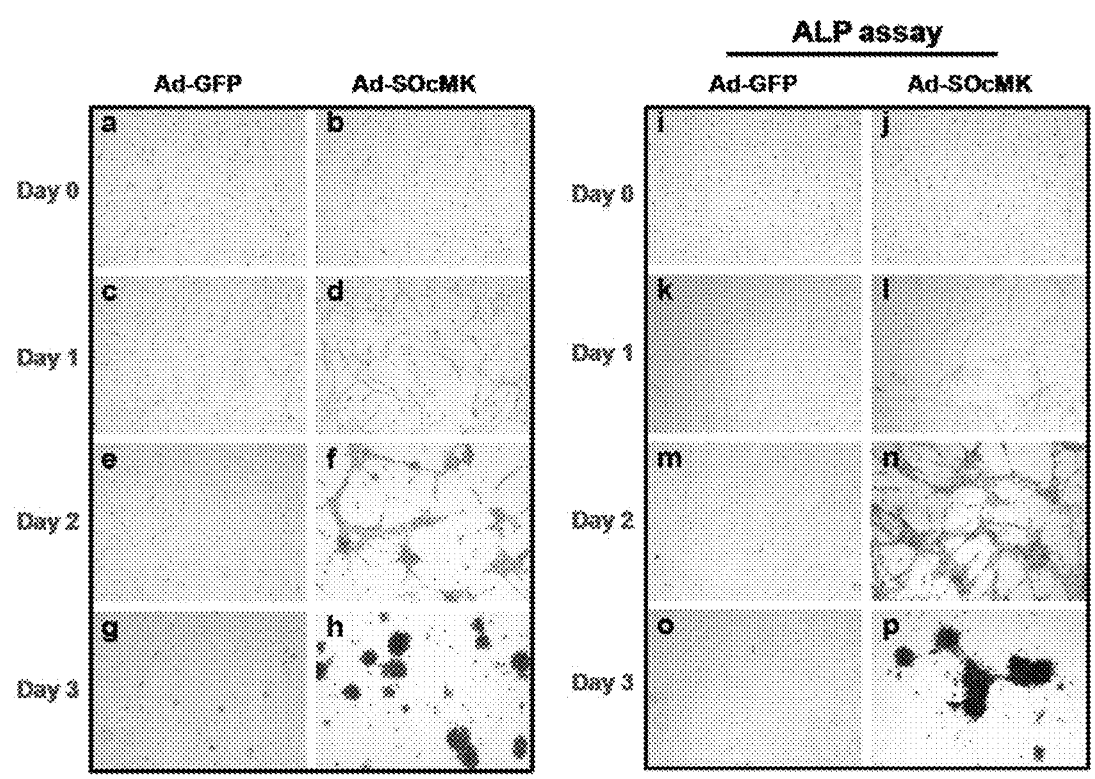
FIG. 9 shows images of cells undergoing morphological changes in accordance with another aspect of the present disclosure.

One of the prominent morphological changes during MET is the transformation of elongated fibroblasts into tightly packed clusters of rounded cells. Ad-SOcMK transduced cells undergo progressive epithelial-like morphological changes from elongated fibroblasts (FIG. 9, panels a, h) to packed clusters of rounded cells as visualized by phase contrast microscopy (FIG. 9, panels d, f, h), Morphological changes occur in close association with expression of ALP. ALP-positive cells appeared as early as day 1 in Ad-SOcMK transduced cells and ALP positive cells progressively increased as reprogramming time increased (FIG. 9, panels l, n, p). Cells transduced with Ad-GFP showed neither morphological changes (FIG. 9, panels c, e, g) nor staining for ALP (FIG. 9, panels k, m, o). Thus, reprogramming of IMR90 cells by Ad-SOcMK results in rapid and specific mesenchymal to epithelial transition with very high efficiency.

Such reprogramming of somatic cells is also accompanied by significant epigenetic changes. As one example, the NANOG promoter changes from a highly methylated state in somatic cells to being unmethylated and active in iPS cells. In one aspect, bisulfite genomic sequence analysis can be used to evaluate the methylation status of cytosine guanine dinucleotides (CpGs) in the NANOG promoter. CpGs are highly unmethylated iPS cells when compared with the highly methylated CpGs in parent IMR90 cells. This indicates that the NANOG promoter is active in iPS cells derived from IMR90 cells resulting in increased steady-state levels (FIG. 8B, lower panel). In order to exclude the possibility of viral DNA integration into genomic DNA, Southern blot analysis can be performed by digesting genomic DNA from iPS cells generated with Ad-SOcMk with BamHI and AscI for KLF4 and c-MYC probes, respectively. Notably, Southern blot analyses does not detect genomic integration of the adenoviral transgene into iPS cells derived from IMR90 cells (data not shown). In addition, chromosomal G-band analyses showed that iPS cells generated with Ad-SOcMK had a normal karyotype of 46XX (data not shown).

Figure 10:
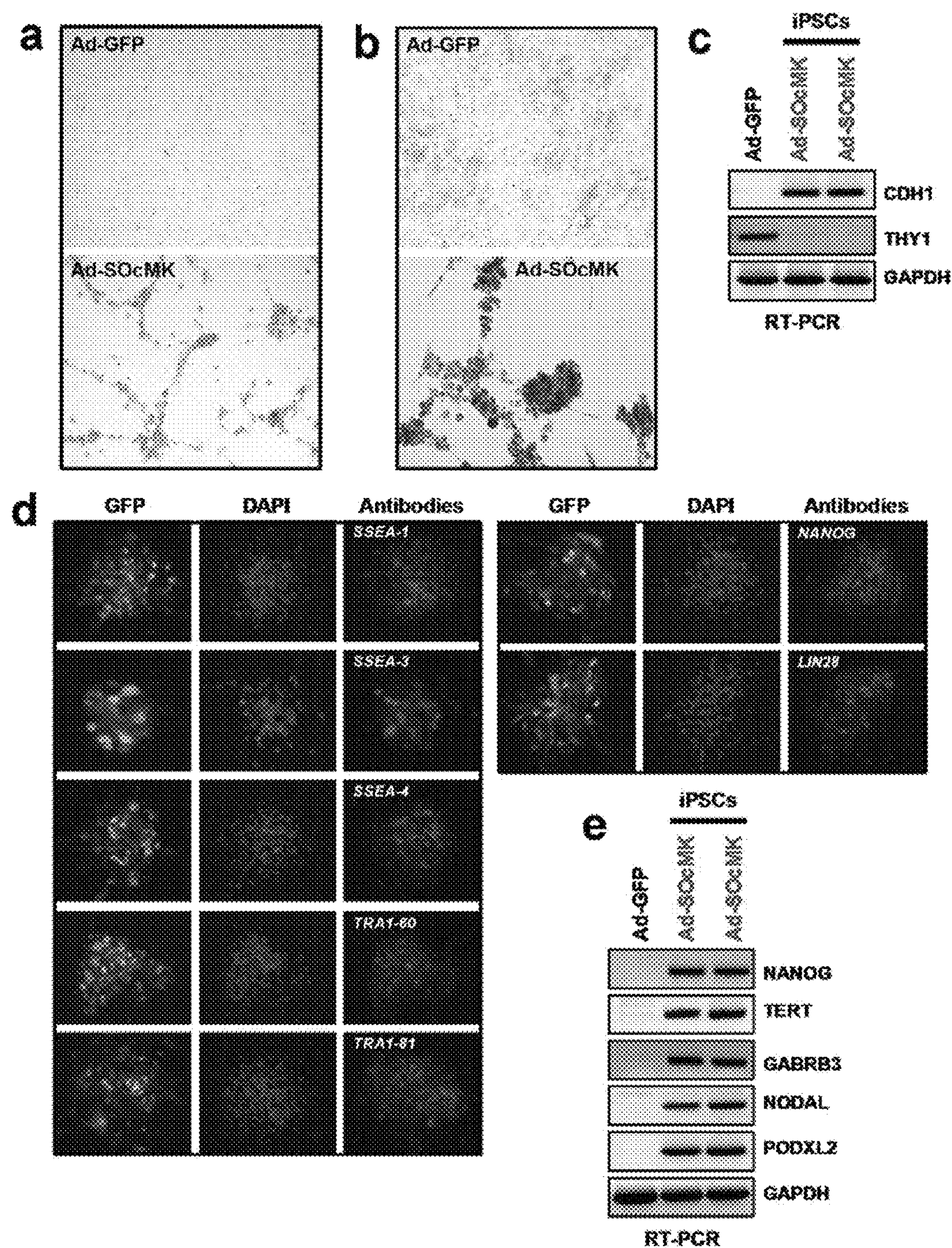
FIG. 10A shows data from SkMC-derived iPS cells in accordance with another aspect of the present disclosure.
FIG. 10B shows data from SkMC-derived iPS cells in accordance with another aspect of the present disclosure.
FIG. 10C shows data from SkMC-derived iPS cells in accordance with another aspect of the present disclosure.
FIG. 10D shows data from SkMC-derived iPS cells in accordance with another aspect of the present disclosure.
FIG. 10E shows data from SkMC-derived iPS cells in accordance with another aspect of the present disclosure.
Figure 11:
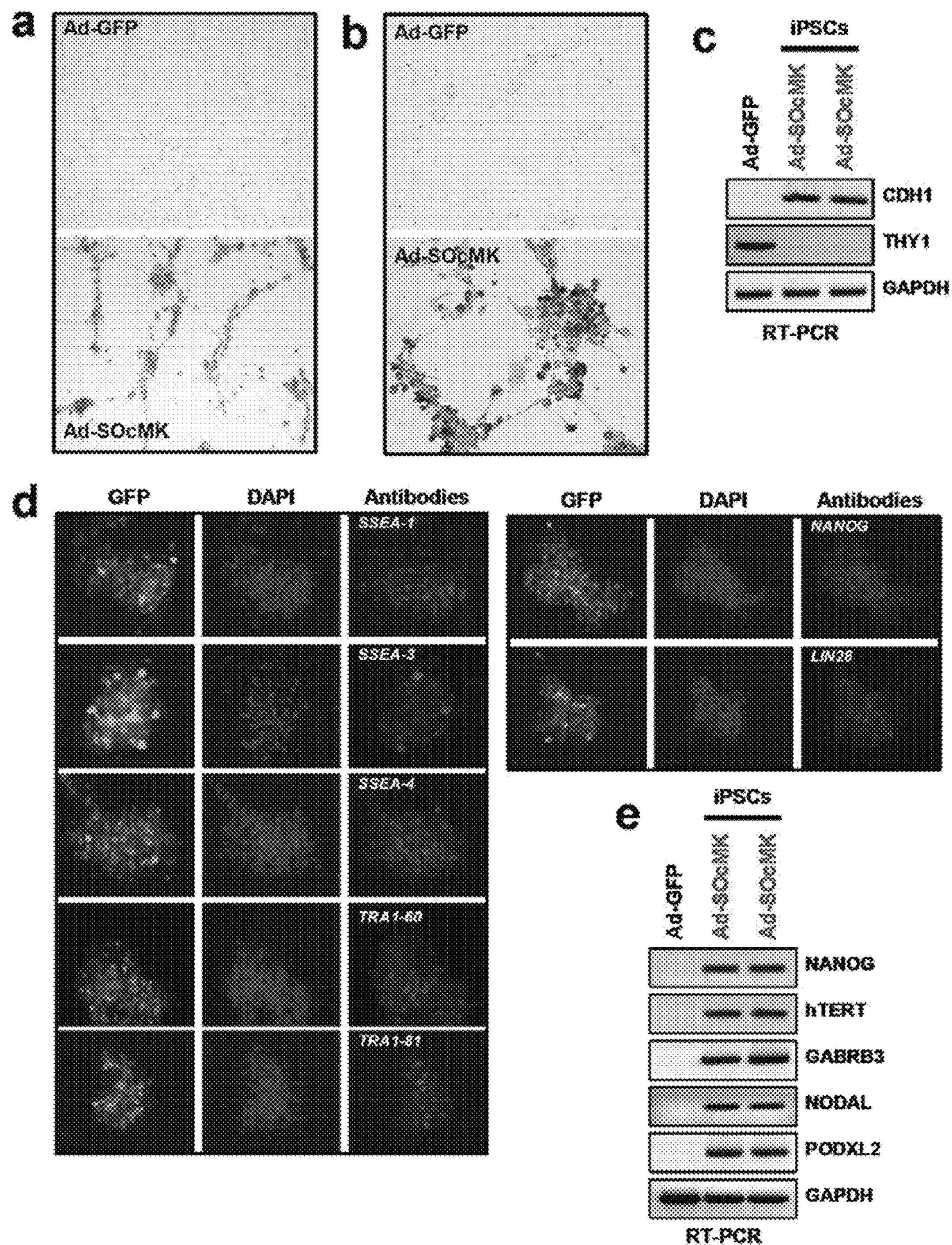
FIG. 11A shows data from SCA2 skin fibroblast-derived iPS cells in accordance with another aspect of the present disclosure.
FIG. 11B shows data from SCA2 skin fibroblast-derived iPS cells in accordance with another aspect of the present disclosure.
FIG. 11C shows data from SCA2 skin fibroblast-derived iPS cells in accordance with another aspect of the present disclosure.
FIG. 11D shows data from SCA2 skin fibroblast-derived iPS cells in accordance with another aspect of the present disclosure.
FIG. 11E shows data from SCA2 skin fibroblast-derived iPS cells in accordance with another aspect of the present disclosure.

As has been described, a variety of cell types can be utilized to generate iPS cells according to aspects of the present disclosure, and any such capable cell is considered to be within the present scope. As examples, human skeletal muscle cells (SkMCs) and spinocerebellar ataxia 2 (SCA2) patient skin fibroblasts can be used. When SkMCs and SCA2 skin fibroblasts are transduced, several iPS cell colonies resembling ES cell-like morphology emerge in the dishes as early as day 3. The SkMC and SCA2 skin fibroblast-derived iPS cells positively stain for ALP, and immunofluorescence and RT-PCR analysis data reveals that these iPS cells express many undifferentiated ES cell-marker genes and followed the MET process (For SkMCs see FIG. 10, panels a-e; for SCA2 see FIG. 11, panels a-e). These findings demonstrate that the expression vectors of the present disclosure can be used to generate iPS cells rapidly and efficiently from a number of somatic cells in a short period of time.

Figure 12:
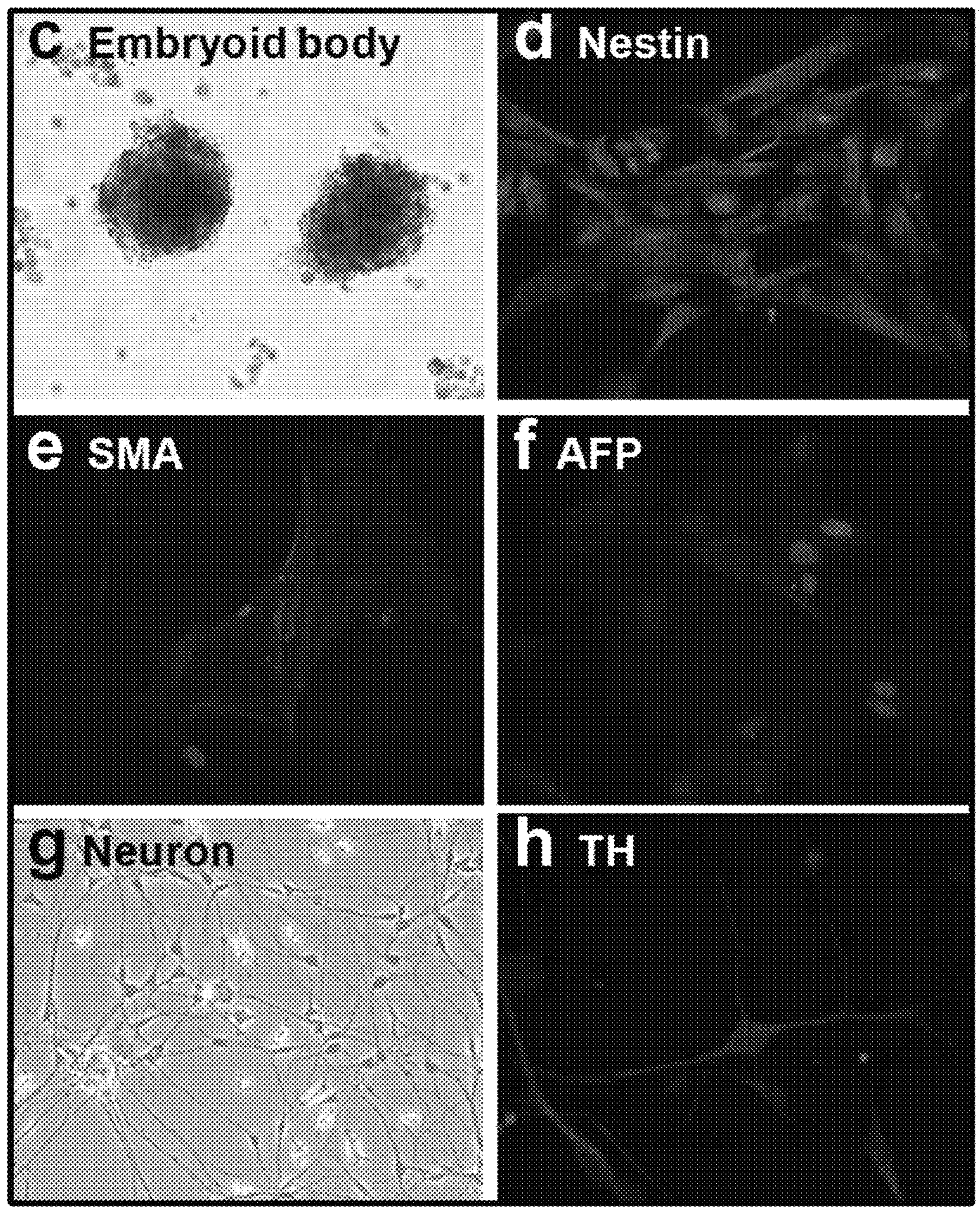
FIG. 12 shows immunohistochemistry data from differentiated iPS cells in accordance with another aspect of the present disclosure.

One of the useful characteristics of pluripotency is the ability of iPS cells to differentiate into all three germ layers. The following non-limiting example is provided to show such differentiation. For example, for in vitro differentiation, freshly prepared iPS cells with Ad-SOcMK as have been described were cultured in ES cell medium without basic fibroblast growth factor (bFGF) for 8-9 days. The resultant embryoid bodies (EBs) in suspension cultures (see FIG. 12, panels c-j) are allowed to differentiate further in chamber slides. After 9-10 days in adherent culture, attached cells show various types of morphologies. Immunocytochemistry reveals the detection of Nestin (ectoderm, FIG. 12, panel d), smooth muscle actin (SMA) (mesoderm, FIG. 12, panel e), and alpha-fetoprotein (AFP) (endoderm, FIG. 12, panel f). To test whether iPS cells could be differentiated into neurons, iPS cells are seeded on inactivated MEF cells and cultured for 22-25 days. Morphological and immunostaining data revealed that the iPS cells were differentiated into neurons with a subpopulation of neurons staining with the dopaminergic marker tyrosine hydroxylase (TH) (FIG. 12, panels g, h).

Figure 13:
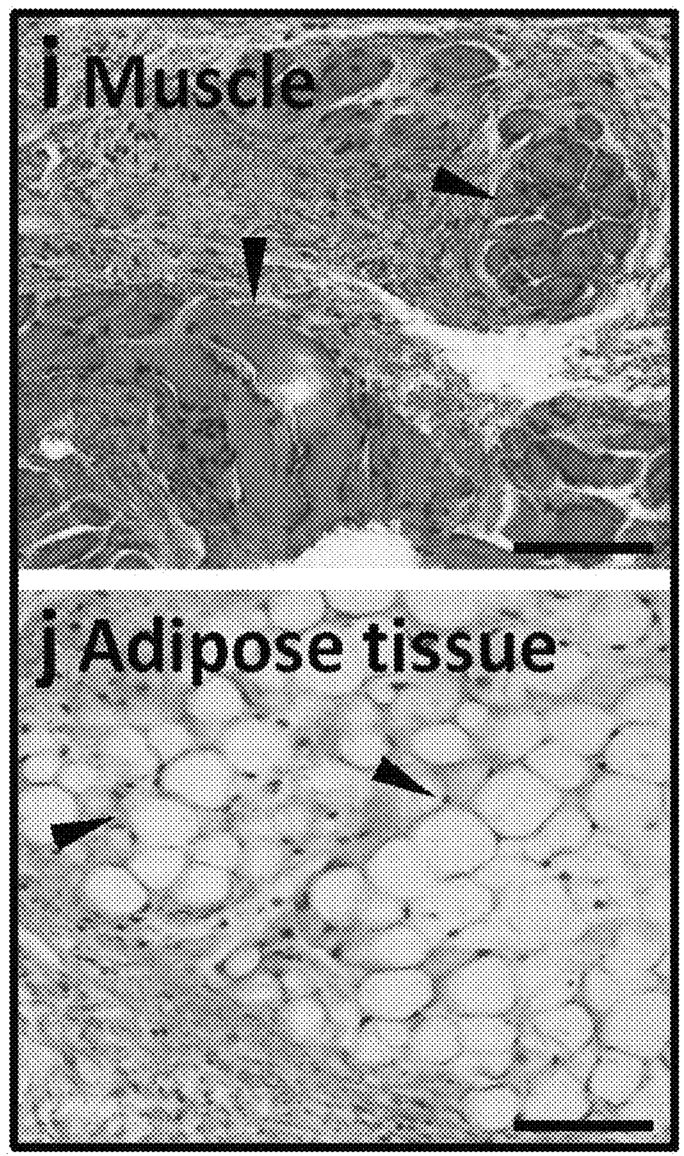
FIG. 13 shows histological data revealing development of muscle and adipose tissues in accordance with another aspect of the present disclosure.

To examine developmental potential in vivo, iPS cells generated with Ad-SOcMK are injected into NOD/SCID mice subcutaneously. After 9-10 weeks, teratomas develop and histological data reveals development of muscle and adipose tissues (mesoderm) (FIG. 13, panels I, j). Thus, iPS cells generated according to aspects of the present disclosure show pluripotency with the potential of differentiating into germ layers in vitro and in vivo.

Figure 14:
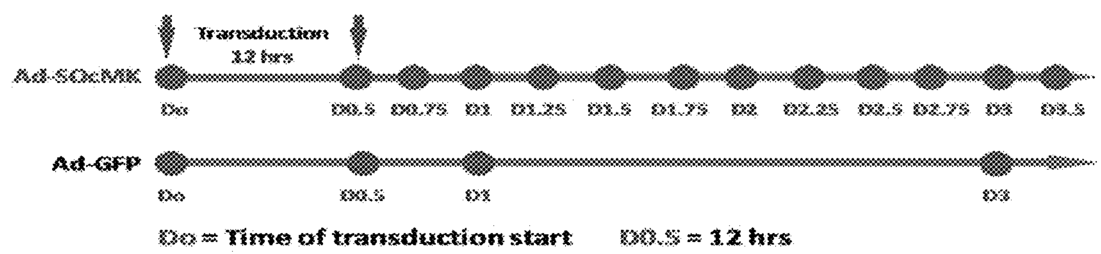
FIG. 14 shows an illustration of an experimental time line in accordance with another aspect of the present disclosure.

As has been described, traditional methods for reprogramming of human primary somatic cells have low efficiency, making the molecular characterization of reprogramming difficult. Given the rapid time course and absence of feeder cell contamination, the techniques according to aspects of the present disclosure can allow monitoring of expression changes at multiple time points during the reprogramming process as compared to just the beginning (fibroblasts) and final (iPS cells) time points. In one aspect, therefore, RNAs are isolated from Ad-SOcMK and Ad-GFP transduced IMR90 cells at 0, 24, 48 and 72 hrs post-transduction and queried for global gene expression changes by hybridization to oligonucleotide arrays representing 27,958 protein coding genes and 7,419 lincRNAs. Differential expression analyses (>2 fold change) shows changes in 6,852 genes for 0/24 hr, 12,945 for 0/48 hr, and 14,158 for 0/72 hr (data not shown). Based on the significant and rapid changes in global gene expression, the experiment is repeated and RNA expression is analyzed at 6 hr intervals for 84 hrs after Ad-SOcMK transduction, FIG. 14 shows an illustration of the experimental time line. To identify temporal waves of gene expression across time points, the entire data set is analyzed, including Ad-GFP-transduced control cells (>1.5-fold differential expression) by using singular value decomposition (SVD)25.

Figure 15A:
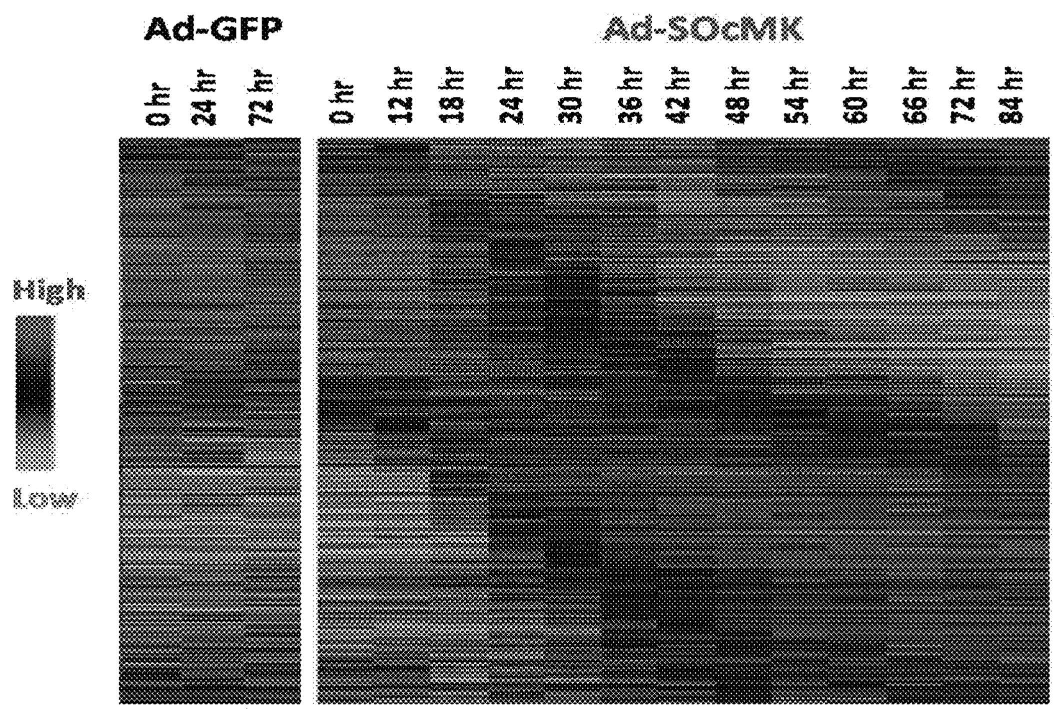
FIG. 15A shows a heat-map of a gene expression profile in accordance with another aspect of the present disclosure.
Figure 15B:
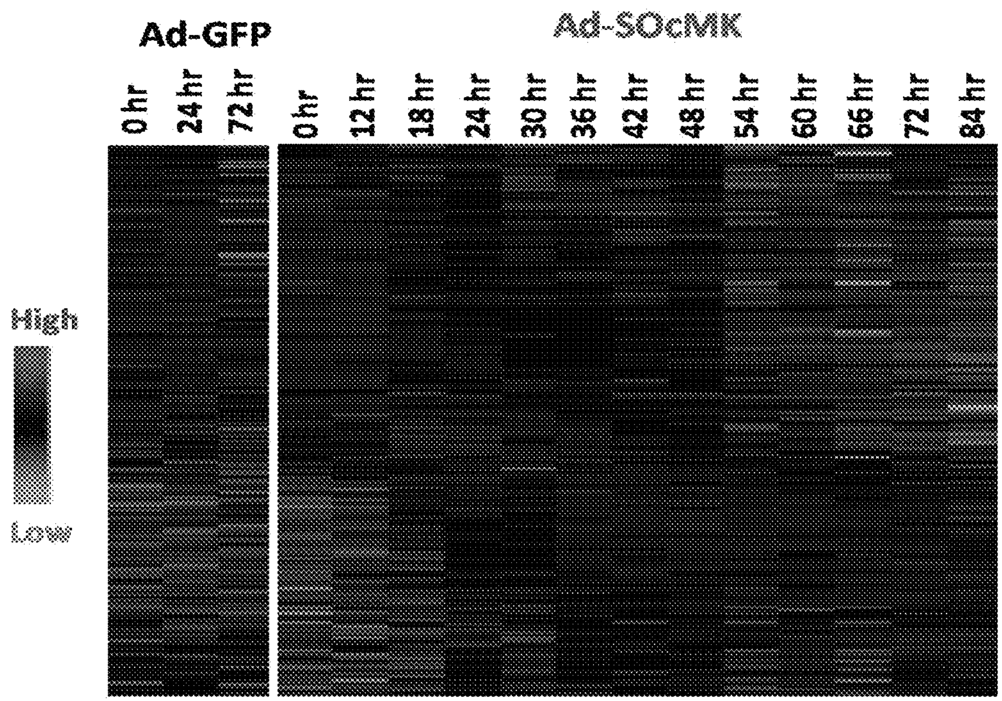
FIG. 15B shows a heat-map of a gene expression profile in accordance with another aspect of the present disclosure.

FIG. 15A shows a heat-map of the gene expression profile for this data set including lincRNAs (21,372 genes). As can be seen in FIG. 15A, a large class of RNAs is highly expressed in IMR90 cells with rapid reduction in the following 12-24 hrs. A second class of RNAs shows little change initially, and then exhibits increased expression with a return to or below initial levels by 72-84 hrs. Additionally, genes in a third group have low expression in the first 24-48 hrs, but then become highly expressed from that time on. Similar clustering of lincRNA expression can be observed (>four-fold differential expression, 1059 lincRNAs, FIG. 15B). Of note, changes in a large number of genes would have remained undetectable as the expression levels were similar at 0/12 hrs compared with 74/82 hrs, while expression greatly changed at the intervening time points.

Gene ontology and KEGG annotation can then be used to examine pathway-wide changes (Table 1). To do this, the heat-map of gene expression (FIG. 15A) is broken down into an early wave: 10%-40% percentile genes, an intermediate wave: 40%-75% percentile genes, and a late wave: 75%-95% percentile genes: Genes related to cytokine-cytokine receptor interactions are up-regulated in the early wave and remain no through 72 hrs (z-score >4.1 at all time points). Genes related to hedgehog signaling show increased expression in the intermediate and late waves (z-score >4.3). Genes involved in DNA replication and cell cycle genes are down-regulated in the intermediate and late wave (z-score >6.2). Additionally, it was validated that various randomly selected genes are specifically enriched or down regulated in ES cells from the two microarray data sets by real-time PCR. For all genes, expression changes are in the same direction within the same order of magnitude (data not shown).

TABLE 1

| KEGG pathway genes | | | | | | |
|---|---|---|---|---|---|---|
| Wave | KEGG Pathway | Gene Set | Number of Genes Up | Number of Genes Down | z-score (Up) | z-score (Down) |
| Early | Cytokine-cytokine receptor interaction | 265 | 13 | | 4.14 | |
| Intermediate | Hedgehog signaling pathway | 56 | 14 | | 4.89 | |
| | Cytokine-cytokine receptor interaction | 265 | 41 | | 4.88 | |
| | Protein digestion and absorption | 78 | 16 | | 4.29 | |

TABLE 1-continued

| KEGG pathway genes | | | | | | |
|---|---|---|---|---|---|---|
| Wave | KEGG Pathway | Gene Set | Number of Genes Up | Number of Genes Down | z-score (Up) | z-score (Down) |
| Late | Cytokine-cytokine receptor interaction | 265 | 57 | | 5.87 | |
| | Gastric acid secretion | 74 | 20 | | 4.6 | |
| | Malaria | 49 | 15 | | 4.55 | |
| | Hedgehog signaling pathway | 56 | 16 | | 4.37 | |
| | Neuroactive ligand-receptor interaction | 311 | 55 | | 4.14 | |
| Intermediate | Cell cycle | 122 | | 27 | | 7.21 |
| | DNA replication | 35 | | 12 | | 6.78 |
| | Oocyte meiosis | 111 | | 19 | | 4.68 |
| | TGF-beta signaling pathway | 83 | | 15 | | 4.4 |
| Late | DNA replication | 35 | | 16 | | 6.98 |
| | Cell cycle | 122 | | 33 | | 6.23 |
| | Homologous recombination | 27 | | 11 | | 5.27 |
| | Systemic lupus erythematosus | 122 | | 27 | | 4.42 |
| | Pathways in cancer | 325 | | 56 | | 4.34 |
| | Pancreatic cancer | 70 | | 18 | | 4.33 |
| | TGF-beta signaling pathway | 83 | | 20 | | 4.23 |

As has been described, in some aspects an altered promoter can be utilized to alter the expression of a particular reprogramming factor. The expression of the reprogramming factor can be increased or decreased, depending on the desired results. In one specific aspect, a weakened CMV promoter ($CMV_{WP}$) can be utilized. It should be understood that the discussion of the $CMV_{WP}$ should not be seen as limiting, and is merely exemplary. Because of strong promoter activity, CMV promoter (589 bp) has previously been used in mammalian system to express a protein in order to study protein functionality. Decreasing the expression of a reprogramming factor can be beneficial in the reprogramming process. In some cases, overexpression of a protein may actually hamper the reprogramming process. As such, in some cases factors can be tuned to more beneficial rates of expression. Additionally, by decreasing the size of the CMV promoter without interruption of promoter activity, a greater sequence size can be loaded into the expression vector. To this end, $CMV_{WP}$ has been developed to, among other reasons, regulate protein expression and allow a higher amount of genetic material to be cloned into a single cassette.

Figure 16:
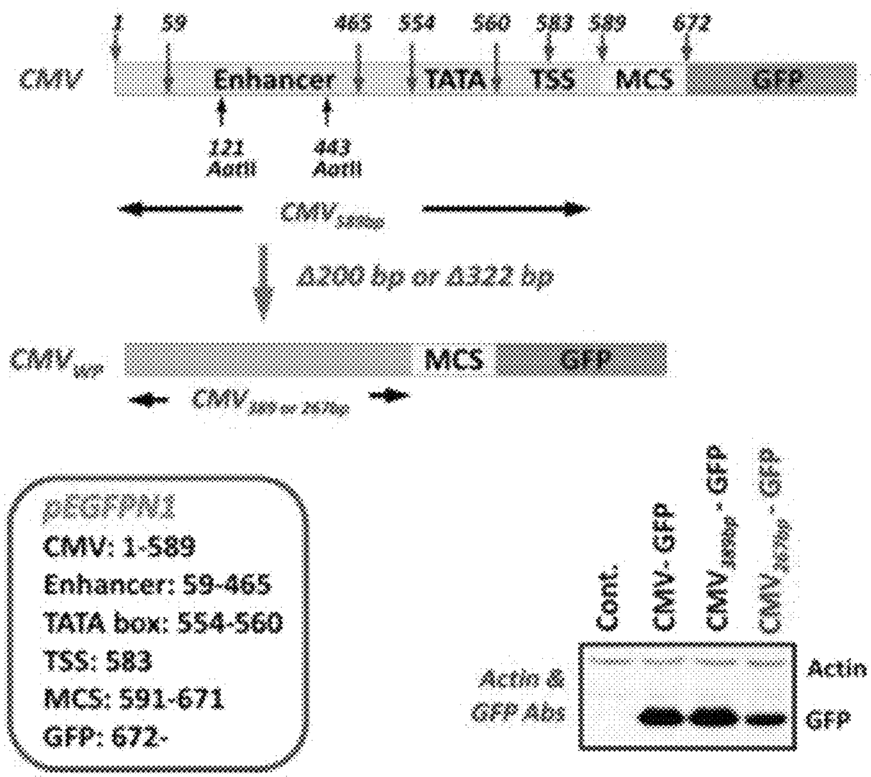
FIG. 16 shows the construction of a CMV weak promoter in accordance with another aspect of the present disclosure.

The inventors have constructed a series of mutant CMV promoters by deleting 200 or 322 bp from original CMV promoter ($CMV_{589bp}$) sequence of pEGFPN1 (Clontech Inc., USA) plasmid using either PCR or restriction digestion methods. The resultant mutant CMV promoters are tested for promoter activity by Western blot analyses expressing in HEK293 or SH-SY5Y cells. Of these, $CMV_{\Delta(121\text{-}443)bp}$-GFP construct, designated as CMV weak promoter-GFP ($CMV_{WP}$-GFP) results in the significant reduction of the GFP protein expression by >60% when compared with $CMV_{589bp}$-GFP or $CMV_{\Delta(1\text{-}200)bp}$-GFP. As is shown in FIG. 16, construction of CMV promoter variants is shown. 200 bp deleted from the 5' end through PCR or 322 bp deleted by AatII digestion from the CMV promoter region of pEGFPN1 is shown in the upper panel of FIG. 16. Validation of promoter activity is shown in the lower panel of FIG. 16. Protein extracts from HEK293 or SH-SY5Y cells transfected with CMV promoter variants were subjected to Western blot analyses using the antibodies indicated. The blots were re-probed for Actin as an internal loading control. $CMV_{\Delta(121-443)bp}$ promoter [CMV weak promoter ($CMV_{WP}$)] results in significant reduction of GFP protein expression.

Figure 17:
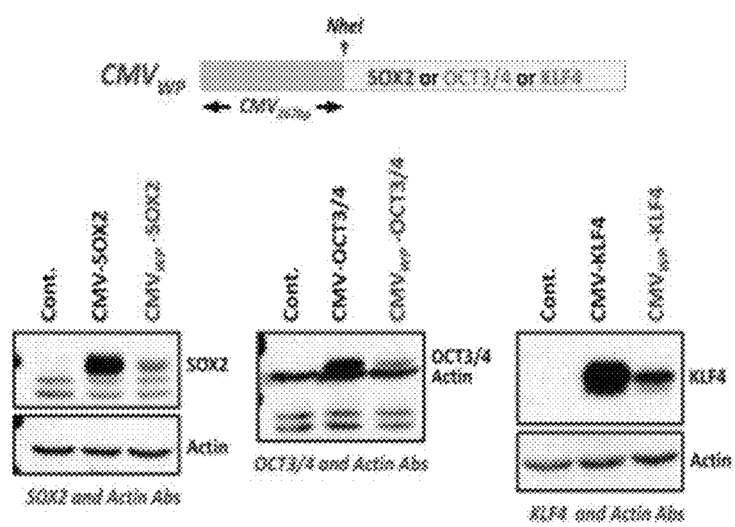
FIG. 17 shows the validation of the CMV weak promoter in accordance with another aspect of the present disclosure.

In order to validate this $CMV_{WP}$ activity further, reprogramming factors OCT3/4, SOX2, KLF4 and c-MYC genes were cloned separately into pre-GFP deleted $CMV_{WP}$-GFP plasmid at NheI site and tested for promoter activity by Western blot analyses expressing in HEK293 or SH-SY5Y cells. The Western blot data revealed the reduction of promoter activity of $CMV_{WP}$ by >70% when compared with $CMV_{589bp}$ promoter (See FIG. 17).

iPS cells are then generated using the $CMV_{WP}$ in the viral cassette as has previously been disclosed for the CMV promoter. In short, IMR90 cells are plated at a density of $1.5\text{~}2.5\times10^6$ cells per 10 cm tissue culture dish without feeder cells. The next day (day 2), IMR90 cells are about 60-70% confluent and the cells are transduced with medium (DMEM, 5% FBS, 1% NEAA, 0.5% penicillin-streptomycin) containing adenoviruses, Ad-GFP (control) or Ad($CMV_{WP}$)-GFP-cMKSO viruses. From day 3 onward, the culture medium is replaced with human ES cell medium including DMEM/F12, 20% Knockout Serum Replacement (KSR), 1× nonessential amino acids, 1× sodium pyruvate, 1× L-glutamine, 0.1 mM b-mercaptoethanol, 25 ng/ml basic fibroblast growth factor (bFGF), and 0.5% penicillin-streptomycin. The medium is changed every day and incubated for 7-8 days. By days 4-7, several colonies showing ES cell-like morphology emerge and all colonies look identical, as shown in FIG. 18B. The resultant colonies (iPSCs) can be further expanded or subjected to characterization. SEQ ID 2, SEQ ID 3, and SEQ ID 4 are examples of adenovirus cassettes utilizing $CMV_{WP}$.

Additionally, as has been described, the undifferentiated state of human ES/iPS cells express high levels of membrane alkaline phosphatase (ALP) and ALP staining can be used to characterize the stem cells. For ALP staining, iPS cells are generated from iMR90 cells in 12 wells plate using the methods described. An experimental timeline is shown in FIG. 18A. At day 4, iPS cells are fixed with 4% paraformaldehyde for 2 minutes, followed by 15-minute incubation with staining solution (Alkaline Phosphatase Detection Kit; Millipore). ALP staining data demonstrates the positive staining for iPS cells, as is shown in FIG. 18C. As such, the $CMV_{WP}$ promoter can be utilized to generate iPS cells according to the methods and techniques described herein.

EXAMPLES

Materials

Reprogramming factors: OCT3/4, SOX2, GKLF4 and c-Myc. Plasmids containing the reprogramming factors (pEP4 E02S ET2K, pCEP4-M2L, pEP4 E02S EN2K, pEP4 E02S CK2M EN2L) are purchased from Addgene Inc., USA.

Each of the reprogramming factors was PCR amplified from the plasmids with NheI restriction sites. The authenticity of each gene was verified by NheI restriction digestion analyses and DNA sequencing.

Plasmid, pEGP-N1 (4.7 kb) is purchased from Clontech Inc., USA.

Adenoviral plasmid (pAdEasy-1, 33.4 kb), Shuttle vectors (pAdTrack and pAdTrack-CMV), Competent cells (AdEasier cells: *E. coli* BJ5183 containing pAdEasy-1 backbone), and Packaging cells (HEK 293A) were generous gift from CoraliePoizet, Larry Kedes Lab, University of Southern California, Los Angeles, Calif., USA.

All enzymes related to cloning experiments are purchased from New England Biolabs Inc., USA.

Human embryonic fibroblast IMR90 cells were obtained from the American Type Culture Collection (ATCC), Catalog No. CCL-186. IMR90 cells were maintained in DMEM medium containing 10% fetal bovine serum (FBS).

Human skeletal muscle cells (SkMCs) were obtained from Lonza Inc., USA, Catalog NO. CC-2661. SkMCs were maintained in SkGM medium (catalog #3160, Lonza Inc., USA), containing 10% FBS.

Human spinocerebellar ataxia 2 (SCA2) skin fibroblasts containing (CAG)57 were obtained from Coriell Cell Repositories, USA Catalog No. # GM04319. SCA2 skin fibroblasts were cultured in MEM medium containing 15% FBS.

DMEM (Invitrogen, cat. no. 11965-092)

Fetal bovine serum, FBS (Hyclone, Thermo Scientific)

KO serum replacement (KOSR; Invitrogen, cat. no. 10828-028)

PBS without Ca/Mg (Hyclone, Thermo Scientific)

L-Gin, 100× (Invitrogen Inc.,)

Nonessential amino acid solution (NEAA) (Invitrogen Inc.,)

2-Mercaptoethanol, 1000×, 55 mM (Invitrogen Inc.,)

Sodium Pyruvate, 100× (Invitrogen Inc.,)

Basic fibroblast growth factor (bFGF; Invitrogen, cat. no. 13256-029)

7.5% BSA solution (wt/vol; Invitrogen, cat. no. 15260-037)

Penicillin/streptomycin, 100× (Invitrogen Inc.,)

0.25% Trypsin/EDTA (Invitrogen, cat. no. 25200-056)

0.05% Trypsin/EDTA (Invitrogen, cat. no. 25300-054)

Collagenase type IV (Invitrogen, cat. no. 17104-019)

Attachment factor, AF 1×, (Invitrogen, cat. no. 17104-019)

Equipment

Inverted tissue culture microscope with phase contrast microscope, Nikon Eclipse, TS100 (5×, 10×, 20×, 40× objectives)

Stereomicroscope (Nikon; SMZ-1500 or similar)

Incubator, Hera cell 240i, Thermo Scientific

Biosafety cabinet with aspirator for tissue culture

Biosafety cabinet with aspirator for tissue culture, fitted for stereomicroscope Tissue culture centrifuge, Sorvall, Legend X1 Centrifuge, Thermo Scientific.

Tissue culture dishes and Flasks, 100 mm, 150 mm and T-25

Tissue culture plates, 4, 6 and 12-well

Filter unit: Millex-HV, PVDF, 0.45 nm, 33 mm, Millipore Inc.,

Conical tubes, 15 and 50 ml

Water bath Isotemp (Fisher Scientific, USA)

Plastic disposable transfer pipettes, 1, 5, 10 and 25 ml

Glass disposable transfer pipettes, 5 ml

Disposable sterile filter system (0.22 μm, 250 ml and 500 ml)

Disposable syringes, 60, 30, 10 and 1 ml

Hypodermic needle, 27-30G

Freezing container (Nalgene Labware, cat. no. 5100)

Cell lifter (Corning, cat. no. 3008)

Reagent Setup

Culture medium 1 (CM-1): DMEM, 10% FBS, and 1% penicillin-streptomycin

Transduction medium: culture medium 2 (CM-2): DMEM, 5% FBS, 1% NEAA, and 0.5% penicillin-streptomycin.

Culture medium 3 (CM-3): DMEM, 10% FBS, 1% NEAA, and 0.5% penicillin-streptomycin.

Mouse embryo fibroblast (MEF) medium: DMEM, 10% FBS, 1% NEAA, and 0.5% penicillin-streptomycin.

hiPS cell medium: DMEM/F12 containing 20% KOSR (vol/vol), 50 ng/ml bFGF, 1× L-Gln, 1×NEAA, 1× Sodium Pyruvate, 100 μM 2-mercaptoethanol, 50 U/ml penicillin, and 50 mg/ml streptomycin.

2× cell-freezing medium: DMEM, 20% DMSO (vol/vol), 40% FBS (vol/vol), and 1% penicillin-streptomycin 2× iPS cell-freezing medium: DMEM/F12, 20% DMSO (vol/vol), 60% FBS (vol/vol), and 20% hiPS medium (vol/vol).

Example 1

Cloning of Reprogramming Factors

Cloning techniques follow methods published in Molecular cloning (A laboratory manual by Tom Maniatis, J. Sambrook, and E. F. Fritsch), which is incorporated herein by reference.

pEGFP-N1 plasmid (4.7 kb; purchased from Clontech Inc., USA.) is digested with BglII and NotI to remove the GFP open reading frame (ORF) from the plasmid backbone. The digestion reaction mix is as follows:

| | |
|---|---|
| pEGFP-N1 Plasmid DNA (1 μg/ul) | 10 μl |
| 10X Buffer | 5 μl |
| BglII (10 U/μl) | 1 μl |
| NotI(10 U/μl) | 1 μl |
| H2O | 33 μl |
| Total | 50 μl |

The digestion reaction mix is incubated at 37° C. for 3-4 hrs. Heat inactivation is performed at 65° C. for 30 min. The digested product is then electrophoresed on a 0.8% agarose gel and the plasmid back bone (3.9 kb) is purified using a gel extraction kit (Qiagen).

Each of the reprogramming factors (OCT3/4, SOX2, GKLF4 and c-Myc) are PCR amplified from pEP4 E02S ET2K or pCEP4-M2L or pEP4 E02S EN2K or pEP4 E02S CK2M EN2L plasmids (Addgene) with NheI restriction sites. The PCR products are cloned into pEGFP N1 (GFP deletion) at NheI site from the above digestion reaction. The ligation reaction mix is as follows:

| | |
|---|---|
| Vector DNA (10 ng/μl) | 1 μl |
| Insert DNA (PCR product) | 5 μl |
| 10X Buffer | 2 μl |
| T4 DNA ligase (3 U/μl) | 1 μl |
| H2O | 11 μl |
| Total | 20 μl |

The ligation reaction mix is incubated at 16° C. for 18-24 hrs. The DNA is mixed with DH5α competent cells (New England Biolabs Inc.) and the transformation is performed. The cell suspension is inoculated onto 10 cm petri dishes containing LB-agar plus 50 μg/ml of kanamycin. The agar plates are incubated at 37° C. for 20-24 hrs. The positive clones of each gene are verified by NheI restriction digestion analyses and DNA sequencing.

In order to clone the four reprogramming factors into the pAdTrack shuttle vector, each cassette from the above reaction is consecutively subcloned into the shuttle vector (Sox2 cassette at HindIII site, OCT3/4 cassette at EcoRV site, KLF4 cassette at SalI site, and c-Myc cassette at NotI site), designated as pAdSOcMK shuttle vector, as is shown in FIG. 1. The ligation reaction mix is as follows:

| | |
|---|---|
| pShuttle Vector DNA (10 ng/μl) | 1 μl |
| Insert DNA (CMV-SOX2-SV40PA) (10 ng/μl) | 5 μl |
| 10X Buffer | 2 μl |
| T4 DNA ligase (3 U/μl) | 1 μl |
| H2O | 11 μl |
| Total | 20 μl |

The ligation reaction mix is incubated at 16° C. for 18-24 hrs. The DNA is mixed with DH5α competent cells and the transformation is performed. The cell suspension is inoculated onto 10 cm petri dishes containing LB-agar plus 50 μg/ml of kanamycin. The agar plates are incubated at 37° C. for 20-24 hrs. The positive clones of each gene are verified by restriction digestion analyses and DNA sequencing.

Example 2

Generation of Recombinant Adenoviral Plasmids by Homologous Recombination in *E. Coli* (FIG. 1)

High competence bacterial cells (*E. coli* BJ5183) are utilized in the following methods to achieve efficient recombination.

Recombinant pAdShuttle plasmid clones containing the reprogramming factors (pAdSOcMK) from Example 1 are grown in 4.0 ml LB/kanamycin in a 5-ml conical tube, and shaken overnight in a 37° C. orbital shaker. The plasmid DNA is purified by an alkaline lysis procedure. It has been found that efficient homologous recombination in AdEasiercells is improved by maintaining the integrity of the shuttle vector DNAs. Plasmids purified with commercial DNA minipreparation kits can contain significant numbers of nicked DNA molecules that may be detrimental to efficient and faithful recombination. The conventional alkaline lysis procedure can provide consistent and reliable results.

The recombinant shuttle vector plasmid is linearized by digesting with the restriction endonuclease PmeI, and purified using a gel extraction kit (Qiagen). The digestion reaction mix is as follows:

| | |
|---|---|
| Recombinant shuttle vector DNA (1 μg/μl) | 10 μl |
| 10X Buffer | 5 μl |
| PmeI (10 U/μl) | 1 μl |
| 100X BSA | 0.5 μl |
| H2O | 33.5 μl |
| Total | 50 μl |

The digestion reaction is incubated at 37° C. for 3-4 hrs. Heat inactivation is performed at 65° C. for 30 min. The digested product is electrophoresed on a 0.8% agarose gel and the plasmid back bone is purified using a gel extraction kit (Qiagen).

10 μl (100 ng/μl) of the linearized plasmid is mixed with 50-100 μl of *E. coli* BJ5183 cells and incubated on ice for 40-60 min. The bacteria/DNA mix is then heat shocked at 42° C. for 1.5-2 min and immediately incubated on ice for 0.5-1 min. The cells are immediately placed in 250-300 μl of LB-Broth and grown at 37° C. for 1.5-2 hrs.

100 μl of the cell suspension is inoculated onto each of three 10 cm petri dishes containing LB-agar plus 50 μg/ml of kanamycin. The agar plates are incubated at 24-30° C. for 2-3 days until colonies appear. Each colony is isolated and grown in 4 ml LB medium containing 50 μg/ml of kanamycin at 24-30° C. for 2 days in an orbital shaker.

Plasmid DNA is isolated using the conventional alkaline lysis method. Pact restriction digestion is performed on candidate clones. Correct recombinants usually yield a large fragment (~30 kb) and a smaller fragment of 4.5 kb.1-3 μl of correct recombinant plasmids (pAdSOcMK adenoviral vector) are retransformed into DH10B competent cells. The correct clones are subjected to restriction enzyme and/or PCR analysis to verify authenticity. The plasmids are purified with Pure Link Maxi Kit (Invitrogen Inc.,) in order to transfect into the packaging cells (HEK 293A cells) for virus production.

Example 3

Adenovirus Production in Packaging Cells (HEK 293A)

Day 1: HEK 293A cells (E1-transformed human embryonic kidney cells) are plated at a density of $1\text{-}2\times10^6$ cells per T-25 flask in cell culture medium containing DMEM, 10% FBS, and 1% penicillin-streptomycin. The cells are incubated at 37° C., 5% $CO_2$ for 24 hr.

Day 2: The confluency can be about 50-70% at the time of transfection. The recombinant adenoviral plasmids (pAdSOcMK) are digested with PacI (often 5 μg DNA is needed for one transfection). The digested plasmids are ethanol precipitated and resuspended in 25-30 μl of sterile $H_20$. A standard lipofectamine transfection is performed according to manufacturer's protocol (Invitrogen Inc.). Mix 5 μg of PacI-digested plasmid and 25 μl of Lipofectamine in 500 μl of OptiMem I medium, and incubate at room temperature for 15-30 min. While waiting, medium from the recipient cells can be removed and the cells can be wash once with a serum-free medium (DMEM).2.5-3.0 ml Opti-Mem I is added to a T-25 flask containing the cells. Incubate the cells (37° C., 5% CO2) for 10-15 min. The lipofectamine-DNA mix is added to the flasks with the cells and returned to the incubator for 5-6 hrs. The lipofectamine/DNA medium is removed and 5-7 ml of fresh cell culture medium is added, and the cells are incubated at 37° C., 5% CO2.

Incubation continues until ~90% of the cells detach (die) from the flask surface. This often takes approximately 20-30 days. Transfections and viral production can be monitored by GFP expression. The cells are scraped off the flask with a scrapper at 20-30 days post-transfection and the medium with the cells is collected in 15/50 ml conical tubes. The tubes are spun in a benchtop centrifuge, and supernatant (sup 1) is collected and the pellet is resuspended in 2-3 ml sterile PBS. The cells are frozen in a dry ice/methanol bath or a −80° C. freezer, thawed in a 37° C. water bath, and vortexed vigorously. This procedure of freeze/thaw/vortex is repeated for 3-4 more cycles. The samples are spun briefly, and the supernatant (sup 2) is collected. Sup 1 and sup 2 are mixed (hereinafter "adenovirus particles"). The adenovirus particles are filtered with a 0.45 μm syringe filter and stored at −20/−80° C. until use.

Example 4

Amplification of Adenoviruses

Two 50-70% confluent T-25 flasks of HEK 293A cells are infected using 40-50% of the viral supernatant containing the adenovirus particles from Example 3 for each flask. Cytopathic effect (CPE) or cell lysis should appear at 7-10 days post infection. Effective production of adenoviruses can be monitored by GFP expression. When >90% of the cells die, the cells are scraped off and adenoviral supernatant is prepared as described in Example 3. Authenticity of recombinant adenovirus can be confirmed by infecting the viral supernatant to any infectable cells and Western blot and/or PCR analyses of target genes. Multiple rounds of infection cycles in HEK 293A cells can be carried out to harvest adenoviral particles.

Example 5

Generation of iPS Cells by Adenoviral Vector Containing Multi-Reprogramming Factors from IMR90 Human Fetal Fibroblasts without Using Feeder Cells Human embryonic fibroblast IMR90 cells are purchased from the American Type Culture Collection (ATCC) (Manassas, Va., http://www.atcc.org; Catalog No. CCL-186). IMR90 cells are cultured and maintained in culture medium 1 (CM-1) containing DMEM, 10% FBS, and 1% penicillin-streptomycin according to manufacturer's protocol.

The fibroblasts IMR90 are thawed as follows:

1. Prepare 9 ml of CM-1 in a 15 ml conical tube.
2. A vial of frozen fibroblasts is removed from the liquid nitrogen tank and placed into a 37° C. water bath until most (but not all) cells are thawed.
3. The vial is wiped with ethanol, the cap is opened, and the cell suspension is transferred to the tube prepared in step 1.
4. The tube is centrifuged at 1100 rpm for 3 minutes, and the supernatant is discarded.
5. The cells are re-suspended in 10 ml of CM-1, and transferred to a 100 mm dish (0.5-1×105 cells/dish). The cells are incubated in a 37° C., 5% CO2 incubator until the cells become 80~90% confluent. The medium is changed every other day.

The fibroblasts are passaged as follows:

1. The medium is discarded the cells are washed once with PBS.
2. The PBS is aspirated, and 1.5 ml per dish of 0.05% trypsin/0.53 mM EDTA is added, and the cells are incubated for 1-2 minutes at 37° C.
3. 8.5 ml of CM-1 is added, and the cells are separated into a single cell suspension by pipetting up and down several times.
4. The cell suspension is adjusted to 40 ml by the addition of CM-1 medium, and transferred to dishes (10 ml per 10 mm dish). Thus the cells are divided up in a 1:4 ratio. The cells are incubated at 37° C., 5% CO2 until the cells become 80-90% confluent. This commonly takes 4-5 days after passage.

Adenoviral transduction is accomplished as follows:

Day 1: IMR90 cells are plated at a density of $1.5\text{~}2.5\times10^6$ cells per 10 cm tissue culture dish in CM-1 without feeder cells and incubated at 37° C., 5% $CO_2$ for 24 hr.

Day 2: When IMR90 cells are about 60-70% confluent, the culture medium is removed and the cells are transduced with culture medium 2 (CM-2) including DMEM, 5% FBS, 1% NEAA, 0.5% penicillin-streptomycin and also containing adenovirus particles as generated in either of Examples 3 and 4, Ad-GFP or Ad-SOK or Ad-SOcMK at 100-500 pfu/cell. The cells are incubated at 37° C., 5% CO2 for 24 hr.

Day 3: The culture medium is changed with culture medium 3 (CM-3) including of DMEM, 10% FBS, 1%

NEAA, 0.5% penicillin-streptomycin. The cells are incubated at 37° C., 5% $CO_2$ for 24 hr.

Day 4: Incubation continues. The medium is changed every day with CM-3 and incubated for more 3-4 days.

By days 4-7, several colonies showing ES cell-like morphology emerge and all colonies look identical, as shown in FIG. 3.

Example 6

Adenovirus Transduction and iPSC Generation

IMR90 cells (1.0-1.5×106) are cultured overnight on 100 mm dishes without feeder cells. On the following day, cells are transduced with Ad-SOcMK or Ad-GFP (control). Adenoviruses are removed at 24 hrs post-transduction (day 1), and replaced with human ES cell medium consisting of DMEM/F12 (#11330-32, Invitrogen Inc., USA), 20% Knockout Serum Replacement (KSR) (#10828-028, Invitrogen Inc., USA), 1× nonessential amino acids, 1× sodium pyruvate, 1× L-glutamine, 0.1 mM β-mercaptoethanol, 25 ng/ml basic fibroblast growth factor (bFGF) (#PHG0263, Invitrogen Inc., USA), and 0.5% penicillin-streptomycin. The medium is changed every day and by days 2-3, several colonies showing ES cell-like morphology emerged on the dish. The same protocol is used to generate iPSCs from SkMCs and SCA2 patient skin fibroblasts. Feeder cells are not used.

Example 7

Western Blot Analysis

Protein extracts are resolved by SDS-PAGE and transferred to Hybond P membranes (Amersham Bioscience Inc., USA). After blocking with 5% skim milk in 0.1% Tween 20/PBS, the membranes are incubated with primary antibodies in 5% skim milk in 0.1% Tween 20/PBS for 2 hrs at room temperature or overnight at 4° C. After several washes with 0.1% Tween 20/PBS, the membranes are incubated with the corresponding secondary antibodies conjugated with HRP in 5% skim milk in 0.1% Tween 20/PBS for 2 hrs at room temperature. Following three additional washes with 0.1% Tween 20/PBS, signals are detected by using the Immobilon Western Chemiluminescent HRP Substrate (#WBKLSO100, Millipore Inc., USA) according to the manufacturer's protocol. The antibodies with their sources and dilutions are listed in Table 2.

TABLE 2

Antibodies

| Antibodies | Dilutions (Western blot) | Dilutions (Immuno-fluorescence) | Vendors name | Catalog # |
|---|---|---|---|---|
| Primary Antibodies: Monoclonal antibodies (mAb): | | | | |
| OCT-3/4 (C-10) | 1:5000 | | Santa Cruz Inc., USA | sc-5279 |
| GKLF (B-9) | 1:7000 | | " | sc-166100 |
| c-MYC (9E10) | 1:5000 | | " | sc-40 |
| SSEA-1 | | 1:500 | Millipore Inc., USA | MAB4301-20 |
| SSEA-3 | | 1:500 | " | MAB4303-20 |
| SSEA-4 | | 1:500 | " | MAB4304-20 |
| TRA-1-60 | | 1:500 | " | MAB4360-20 |
| TRA-1-81 | | 1:500 | " | MAB4381-20 |
| Smooth Muscle Actin (SMA) | | 1:500 | " | CBL171 |
| Alpha Feto Protein (AFP) | | 1:500 | " | 2004189 |
| Polyclonal antibodies (pAb): Host: Rabbit | | | | |
| SOX-2 (H-65) | 1:4000 | | Santa Cruz Inc., USA | sc-20088 |
| LIN-28 (H-44) | | 1:500 | " | sc-67266 |
| TERT (H-231) | | 1:500 | " | sc-7212 |
| NANOG | 1:3000 | 1:500 | Cell Signaling Tech., USA | 3580 |
| THY1 | 1:4000 | | Cell Signaling Tech., USA | 9798 |
| Nestin | | 1:500 | Millipore Inc., USA | AB5922 |
| mAb conjugated with HRP: | | | | |
| Beta-Actin (AC-15) | 1:10000 | | Sigma Inc., USA | A3854 |
| Secondary Antibodies: Conjugation: HRP | | | Sigma Inc., USA | A2304 |
| anti-mouse IgG | 1:5000 | | | |
| anti-rabbit IgG | 1:5000 | | Santa Cruz Inc., USA | sc-2077 |
| Conjugation: Dylight 549 | | | | |
| anti-mouse IgG | | 1:2000 | Fisher Scientific, USA | 35507 |
| anti-rabbit IgG | | 1:2000 | " | 35557 |

Example 8

Alkaline Phosphatase Staining and Immunocytochemistry

ALP staining was performed using the Alkaline Phosphatase Detection Kit (#SCR004, Millipore Inc., USA). Briefly, iPS cells are fixed with 4% paraformaldehyde/PBS for 2 min, followed by 15 min incubation with staining solution according to the manufacturer's protocol. For immunocytochemistry, cells are fixed in 4% paraformaldehyde/PBS for 20 min at room temperature. The cells are then permeabilized with 70% ethanol and stored at 4° C. After washing with PBS, cells were blocked with 10% BSA/PBS for 2 hrs at room temperature. Slides were incubated with primary antibodies in 10% BSA/PBS for 2 hrs at room temperature or overnight at 4° C., washed three times with PBS and incubated with the corresponding secondary antibodies conjugated with Dylight variants. Following incubation, cells are washed three times with PBS and nuclei stained with 4',6-diamidino-2-phenylindole (DAPI) (Sigma Inc., USA). The slides are mounted with mounting medium, Vectashield (Vector Inc., USA) and cells visualized using confocal microscopy (Nikon Eclipse Ti microscopy). The antibodies with their sources and dilutions are listed in Table 2.

Example 9

PCR Analysis

Total RNA is prepared from harvested cells using the RNAeasy Kit (Qiagen Inc., USA). cDNA is synthesized from 5 μg of total RNA using MMLV reverse transcriptase and random hexanucleotide primers (New England Biolab Inc., USA) according to the manufacturer's protocol. To study gene expression of iPS cells, cDNAs (150 ng for semi-quantitative and 5 ng for real-time PCR) derived from the total RNA is subjected to PCR analysis. In regular PCR, the PCR products are cloned and verified by sequencing. Primer sequences used for semi-quantitative and real-time PCR are listed in Tables 3 and 4.

TABLE 3

| Primers |
|---|
| CDH1 |
| Forward: SEQ ID 5<br>5'-AGCCATGGGCCCTTGGAGCCGCAG-3'<br>Reverse: SEQ ID 6<br>5'-GGAATAACCCAGTCTCTCTTCTGTC-3' |
| GAL |
| Forward: SEQ ID 7<br>5'-TGCGGCCCGAAGATGACATGAAACC-3'<br>Forward: SEQ ID 8<br>5'-CCCAGGAGGCTCTCAGGACCGCTC-3' |
| THY1 |
| Forward: SEQ ID 9<br>5'-GAGGAGGCTGCAGCAGCGGAAGAC-3'<br>Forward: SEQ ID 10<br>5'-GAGCCAGCAGGCTGATGCCCTCAC-3' |

TABLE 3-continued

| Primers |
|---|
| GABRB3 |
| Forward: SEQ ID 11<br>5'-CCTTGCCCAAAATCCCCTATGTCAAAGC-3'<br>Reverse: SEQ ID 12<br>5'-GTATCGCCAATGCCGCCTGAGACCTC-3' |
| NANOG |
| Forward: SEQ ID 13<br>5'-ATTATAAATCTAGAGACTCCAGG-3'<br>Reverse: SEQ ID 14<br>5'-CATGGAGGAAGGAAGAGGAGAGAC-3' |
| TDGF1 |
| Forward: SEQ ID 15<br>5'-CTGCTGCCTGAATGGGGGAACCTGC-3'<br>Reverse: SEQ ID 16<br>5'-GCCACGAGGTGCTCATCCATCACAAGG-3' |
| ALPL |
| Forward: SEQ ID 17<br>5'-TTATAAGGCGGCGGGGGTGGTGGC-3'<br>Reverse: SEQ ID 18<br>5'-CGAAGGGGAACTTGTCCATCTCCAG-3' |
| NODAL |
| Forward: SEQ ID 19<br>5'-ATCATCCGCAGCCTACAGGCAG-3'<br>Reverse: SEQ ID 20<br>5'-CTGTCCCTCCTGGGCCCGCCAGG-3' |
| TERT |
| Forward: SEQ ID 21<br>5'-CCTGCTCAAGCTGACTCGACACCGTG-3'<br>Reverse: SEQ ID 22<br>5'-GGAAAAGCTGGCCCTGGGGTGGAGC-3' |
| PODXL2 |
| Forward: SEQ ID 23<br>5'-CTCAACCAGCAGCTCCTAGAAGGG-3'<br>Reverse: SEQ ID 24<br>5'-GCTGGCCCGCGCCTGGCAGCTGC-3' |
| GDF3 |
| Forward: SEQ ID 25<br>5'-CTTATGCTACGTAAAGGAGCTGGG-3'<br>Reverse: SEQ ID 26<br>5'-GTGCCAACCCAGGTCCCGGAAGTT-3' |
| GAPDH |
| Forward: SEQ ID 27<br>5'-TGAAGGTCGGAGTCAACGGATTTGG-3'<br>Reverse: SEQ ID 28<br>5'-GGAGGCCATGTGGGCCATGAG-3' |
| FGF4 |
| Forward: SEQ ID 29<br>5'-CTACAACGCCTACGAGTCCTACAAG-3'<br>Reverse: SEQ ID 30<br>5'GTTGCACCAGAAAAGTCAGAGTTG-3' |

TABLE 3-continued

| Primers |
|---|
| OCT3/4* |
| Forward: SEQ ID 31<br>5'-AGGAGTCCCAGGACATCAAAGCTCTG-3' |
| SOX2* |
| Forward: SEQ ID 32<br>5'-CCGGCGGCAATAGCATGGCGAGCGG-3' |
| DPPA4 |
| Forward: SEQ ID 33<br>5'-ATATCCCGCCGTGGGTGAAAGTTC-3'<br>Reverse: SEQ ID 34<br>5'-ACTCAGCCATGGACTGGAGCATCC-3' |
| KLF4* |
| Forward: SEQ ID 35<br>5'-TCCAATTCGCTGACCCATCCTCCG-3' |

TABLE 3-continued

| Primers |
|---|
| IFITM1 |
| Forward: SEQ ID 36<br>5'-<br>CCCCAAAGCCAGAAGATGCACAAGGAGG-<br>3'<br>Reverse: SEQ ID 37<br>5'-CGTCGCCAACCATCTTCCTGTCCCTAG-3' |
| c-MYC* |
| Forward: SEQ ID 38<br>5'-ATGGTGACCGAGCTGCTGGGAGGAG-3' |
| Poly A* |
| Reverse: SEQ ID 39<br>5'-ATACATTGATGAGTTTGGACAAAC-3' |

*Primers used for exogenous gene.

TABLE 4

| Primers | |
|---|---|
| THY1 | TDGF1 |
| Forward: SEQ ID 40<br>5'-GAGGAGGCTGCAGCAGCGGAAGAC-3'<br>Reverse: SEQ ID 41<br>5'-CCACTAGGCAGGCCGTTAGGCTGG-3' | Forward: SEQ ID 42<br>5'-GGATACAGCACAGTAAGGAGC-3'<br>Reverse: SEQ ID 43<br>5'-GCACAGACCCACAGTTCTC-3' |
| OCT3/4 | GDF3 |
| Forward: SEQ ID 44<br>5'-TCTCCCATGCATTCAAACTGAG-3'<br>Reverse: SEQ ID 45<br>5'-CCTTTGTGTTCCCAATTCCTTC-3' | Forward: SEQ ID 46<br>5'-CCCGAGACTTATGCTACGTAAAG-3'<br>Reverse: SEQ ID 47<br>5'-GGCAGACAGGTTAAAGTAGAGG-3' |
| NANOG | ALPL |
| Forward: SEQ ID 48<br>5'-AGCTACAAACAGGTGAAGACC-3'<br>Reverse: SEQ ID 49<br>5'-GTGGTAGGAAGAGTAAAGGCTG-3' | Forward: SEQ ID 50<br>5'-GATGTGGAGTATGAGAGTGACG-3'<br>Reverse: SEQ ID 51<br>5'-GGTCAAGGGTCAGGAGTTC-3' |
| TERT | GABRB3 |
| Forward: SEQ ID 52<br>5'-GCACGGCTTTTGTTCAGATG-3'<br>Reverse: SEQ ID 53<br>5'-CGGTTGAAGGTGAGACTGGC-3' | Forward: SEQ ID 54<br>5'-CAAGGCAAAGAATGACCGTTC-3'<br>Reverse: SEQ ID 55<br>5'-TGCTGAATTCCTGGTATCGC-3' |
| LIN28 | NODAL |
| Forward: SEQ ID 56<br>5'-GCAGAAGCGCAGATCAAAAG-3'<br>Reverse: SEQ ID 57<br>5'-CGGACATGAGGCTACCATATG-3' | Forward: SEQ ID 58<br>5'-AGGAGTTTCATCCGACCAAC-3'<br>Reverse: SEQ ID 59<br>5'-TCTGCCATTATCCACATACAGC-3' |
| IFITM4 | FGF4 |
| Forward: SEQ ID 60<br>5'-ATCAACATCCACAGCGAGAC-3'<br>Reverse: SEQ ID 61<br>5'-CAACCATCTTCCTGTCCCTAG-3' | Forward: SEQ ID 62<br>5'-CCATGAAGGTCACCCACTTC-3'<br>Reverse: SEQ ID 63<br>5'-CTCTTGCATTAAACTCTTCATCCG-3' |
| PODXL2 | CDH1 |
| Forward: SEQ ID 64<br>5'-CCCAGCGAAGAGAATGAAGAG-3'<br>Reverse: SEQ ID 65<br>5'-AATGGAACCTGCCTTCTCAG-3' | Forward: SEQ ID 66<br>5'-CCCAATACATCTCCCTTCACAG-3'<br>Reverse: SEQ ID 67<br>5'-CCACCTCTAAGGCCATCTTTG-3' |

TABLE 4-continued

| Primers | |
|---|---|
| GAL | GAPDH |
| Forward: SEQ ID 68<br>5'-GCGCACAATCATTGAGTTTCTG-3'<br>Reverse: SEQ ID 69<br>5'-AGACAAACATGCCCAGGAGG-3' | Forward: SEQ ID 70<br>5'-GAAGGTGAAGGTCGGAGTCAACG-3'<br>Reverse: SEQ ID 71<br>5'-GAAGATGGTGATGGGATTTCC-3' |

Example 10

Bisulfite Sequencing

To assess the methylation status of CpGs in the promoter region of NANOG, genomic DNA is purified from IMR90 cells transduced with Ad-GFP or Ad-SOcMK using the DNeasy Kit (Qiagen Inc., USA). Purified genomic DNA (1 μg) is used to convert unmethylated cytosines (C) to uracil (U) using EZ DNA methylation kit (#D5001, Zymo Research Inc., USA), according to the manufacturer's protocol. Treated DNA is purified with QIAquick column (Qiagen Inc., USA) and purified DNA (150 ng) from each sample is subjected to PCR analyses for the promoter region of NANOG using the following primers: forward 5'-CACCATGCGTGGCTAATTTTTGTA-3', reverse 5'-TTAAAATCCTGGAGTCTCTAGATTT-3'. The resulting PCR products are subcloned into the pCR2.1-TOPO vector (Invitrogen Inc., USA). Ten clones of each sample are verified by sequencing.

Example 11

In Vitro Differentiation

To determine the differentiation ability of iPS cells in vitro, the floating culture method is used to form Embryoid bodies (EBs). Briefly, IMR90 cells are transduced with Ad-SOcMK. On day 3, the resultant iPS cells are mechanically dissociated and cultured in ES cell medium (without bFGF) in non-coated T25 flasks. The medium is changed every other day. After 7 days in floating culture, ball-shaped structures typical for EBs are formed. EBs are then transferred to 0.1% gelatin-coated chamber slides using the same medium. The medium is changed every other day once EBs are attached to the slide. Differentiated cells are fixed after 8 days in adherent culture and stained with antibodies recognizing marker proteins for each germ layer.

Example 12

Teratoma Formation

To examine the in vivo development potential of iPS cells, IMR90 cells are transduced with Ad-SOcMK. On day 3, the resultant iPSCs are injected subcutaneously to 4 of 6-week-old male nonobese diabetic severe combined immunodeficient (NOD/SCID) mice (Charles River Laboratories) (3×106 iPSCs for each mouse). For control experiment, IMR90 cells (3×106 cells) are also injected into one mouse. After 9-10 weeks, tumors are dissected and fixed in 4% paraformaldehyde. Teratoma experiments are conducted in Comparative Oncology Resource Core at the University of Utah. Samples are embedded in paraffin and stained with hematoxylin and eosin in the Tissue Resource and Application Core (TRAC) at the University of Utah. All procedures are performed in accordance with protocols approved by the University of Utah Animal Research Committee guidelines.

Example 12

Microarray Analyses

IMR90 cells are transduced with Ad-SOcMK or Ad-GFP. Adenoviruses are removed at 12 hrs post-transduction and cells are sampled at every 6 hrs. Total RNA is prepared from each sample using Qiagen RNeasy kit according to manufacturer's protocol. Human genome SurePrintG3 8×60K carrying 27,958 genes and 7,419 LincRNA targets (Agilent Technologies, Inc.) are used for microarray hybridization to examine the global gene expression. Approximately 1 μg of RNA from each sample is labeled using Agilent Two-Color Quick Amp Labeling Kit following manufacturer's instructions. All arrays are hybridized at 65° C. for 17 hrs and scanned using an Agilent scanner G2505C. The gene expression raw data is extracted using Agilent Feature Extraction Software version 10.5. Quality control is done on the basis of Agilent quality control metrics. Singular value decomposition (SVD) of the qualified data, with gene expression centered at its time average, identified several "eigengenes," i.e., significant patterns of expression variation across time. Sorting the data according to the two most significant eigengenes gives a global picture of the dynamics of gene expression, in which individual genes appear to be classified into groups of similar regulation and function25. Array experiments are performed in Microarray Core Facility at the University of Utah.

Of course, it is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail in connection with what is presently deemed to be the most practical embodiments of the disclosure, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A transformation construct for generating induced pluripotent stem (iPS) cells, comprising:

an expression vector including a plurality of reprogramming factors, each reprogramming factor being under control of a separate promoter, wherein the plurality of reprogramming factors includes OCT3/4, SOX2, and at least one member selected from the group consisting of KLF4, c-Myc, NANOG, and LIN28.

2. The construct of claim 1, wherein the expression vector is selected from the group consisting of plasmids, viruses, and combinations thereof.

3. The construct of claim 1, wherein the expression vector is selected from the group consisting of adenoviral vectors, episomal vectors, retroviral vectors, and lentiviral vectors.

4. The construct of claim 1, wherein the expression vector is an episomal vector.

5. The construct of claim 1, wherein the plurality of reprogramming factors includes OCT3/4, SOX2, KLF4, and c-Myc.

6. The construct of claim 1, wherein the plurality of reprogramming factors consists of OCT3/4, SOX2, and KLF4.

7. The construct of claim 1, wherein the plurality of reprogramming factors includes OCT3/4, SOX2, NANOG, and LIN28.

8. The construct of claim 1, wherein the expression vector has a sequence that is at least 80% homologous to SEQ ID 72.

9. The construct of claim 1, wherein the expression vector has a sequence that is at least 95% homologous to SEQ ID 72.

10. The construct of claim 1, wherein at least one of reprogramming factor is under the control of a CMV promoter.

11. The construct of claim 10, wherein the CMV promoter is a weak CMV promoter.

12. The construct of claim 1, wherein the expression vector further includes a reporter sequence under control of a separate promoter.

* * * * *

SEQUENCE LISTING

<160> NUMBER OF SEQ ID NOS: 72

<210> SEQ ID NO 1
<211> LENGTH: 16309
<212> TYPE: DNA
<213> ORGANISM: Artificial Sequence
<220> FEATURE:
<223> OTHER INFORMATION: The adeno shuttle vector containing multi-reprogramming factors has been provided as complementary sequence (pAd-kcMOS). In the text, it should be read as pAd-SOcMK (S; SOX2, O; OCT3/4, cM; c-MYC, K; KLF4)
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (1945)..(1947)
<223> OTHER INFORMATION: n is a, c, g, or t
<220> FEATURE:
<221> NAME/KEY: misc_feature
<222> LOCATION: (7317)..(7317)
<223> OTHER INFORMATION: n is a, c, g, or t
<220> FEATURE:
<221> NAME/KEY: misc_feature
<222> LOCATION: (10202)..(10204)
<223> OTHER INFORMATION: n is a, c, g, or t
<220> FEATURE:
<221> NAME/KEY: misc_feature
<222> LOCATION: (12445)..(12447)
<223> OTHER INFORMATION: n is a, c, g, or t
<220> FEATURE:
<221> NAME/KEY: misc_feature
<222> LOCATION: (12462)..(12464)
<223> OTHER INFORMATION: n is a, c, g, or t
<220> FEATURE:
<221> NAME/KEY: misc_feature
<222> LOCATION: (13447)..(13449)
<223> OTHER INFORMATION: n is a, c, g, or t
<220> FEATURE:
<221> NAME/KEY: misc_feature
<222> LOCATION: (13464)..(13466)
<223> OTHER INFORMATION: n is a, c, g, or t
<220> FEATURE:
<221> NAME/KEY: misc_feature
<222> LOCATION: (14767)..(14772)
<223> OTHER INFORMATION: n is a, c, g, or t

<400> SEQUENCE: 1

```
nnnttaatta annntccctt ccagctctct gccccttttg gattgaagcc aatatgataa      60

tgagggggtg gagtttgtga cgtggcgcgg ggcgtgggaa cggggcgggt gacgtagtag     120

tgtggcggaa gtgtgatgtt gcaagtgtgg cggaacacat gtaagcgacg gatgtggcaa     180

aagtgacgtt tttggtgtgc gccggtgtac acaggaagtg acaattttcg cgcggtttta     240

ggcggatgtt gtagtaaatt tgggcgtaac cgagtaagat ttggccattt tcgcgggaaa     300

actgaataag aggaagtgaa atctgaataa ttttgtgtta ctcatagcgc gtaannncgc     360

gttaagatac attgatgagt ttggacaaac cacaactaga atgcagtgaa aaaaatgctt     420

tatttgtgaa atttgtgatg ctattgcttt atttgtaacc attataagct gcaataaaca     480

agttaacaac aacaattgca ttcattttat gtttcaggtt cagggggagg tgtgggaggt     540

tttttaaagc aagtaaaacc tctacaaatg tggtatggct gattatgatc agttatctag     600
```

-continued

```
atccggtgga tctgagtccg gacttgtaca gctcgtccat gccgagagtg atcccggcgg    660
cggtcacgaa ctccagcagg accatgtgat cgcgcttctc gttggggtct ttgctcaggg    720
cggactgggt gctcaggtag tggttgtcgg gcagcagcac ggggccgtcg ccgatggggg    780
tgttctgctg gtagtggtcg gcgagctgca cgctgccgtc ctcgatgttg tggcggatct    840
tgaagttcac cttgatgccg ttcttctgct tgtcggccat gatatagacg ttgtggctgt    900
tgtagttgta ctccagcttg tgccccagga tgttgccgtc ctccttgaag tcgatgccct    960
tcagctcgat gcggttcacc agggtgtcgc cctcgaactt cacctcggcg cgggtcttgt   1020
agttgccgtc gtccttgaag aagatggtgc gctcctggac gtagccttcg ggcatggcgg   1080
acttgaagaa gtcgtgctgc ttcatgtggt cggggtagcg gctgaagcac tgcacgccgt   1140
aggtcagggt ggtcacgagg gtgggccagg gcacgggcag cttgccggtg gtgcagatga   1200
acttcagggt cagcttgccg taggtggcat cgccctcgcc ctcgccggac acgctgaact   1260
tgtggccgtt tacgtcgccg tccagctcga ccaggatggg caccaccccg gtgaacagct   1320
cctcgccctt gctcaccatg gtggcgaccg gtagcgctag cggatctgac ggttcactaa   1380
accagctctg cttatataga cctcccaccg tacacgccta ccgcccattt gcgtcaatgg   1440
ggcggagttg ttacgacatt ttggaaagtc ccgttgattt tggtgccaaa acaaactccc   1500
attgacgtca atggggtgga gacttggaaa tccccgtgag tcaaaccgct atccacgccc   1560
attgatgtac tgccaaaacc gcatcaccat ggtaatagcg atgactaata cgtagatgta   1620
ctgccaagta ggaaagtccc ataaggtcat gtactgggca taatgccagg cgggccattt   1680
accgtcattg acgtcaatag gggcgtact tggcatatga tacacttgat gtactgccaa   1740
gtgggcagtt taccgtaaat actccaccca ttgacgtcaa tggaaagtcc ctattggcgt   1800
tactatggga acatacgtca ttattgacgt caatgggcgg gggtcgttgg gcggtcagcc   1860
aggcgggcca tttaccgtaa gttatgtaac gcggaactcc atatatgggc tatgaactaa   1920
tgaccccgta attgattact attannncta gcagatctgg taccgtcgat aatagtaatc   1980
aattacgggg tcattagttc atagcccata tatggagttc cgcgttacat aacttacggt   2040
aaatggcccg cctggctgac cgcccaacga cccccgccca ttgacgtcaa taatgacgta   2100
tgttcccata gtaacgccaa tagggacttt ccattgacgt caatgggtgg agtatttacg   2160
gtaaactgcc cacttggcag tacatcaagt gtatcatatg ccaagtacgc cccctattga   2220
cgtcaatgac ggtaaatggc ccgcctggca ttatgcccag tacatgacct tatgggactt   2280
tcctacttgg cagtacatct acgtattagt catcgctatt accatggtga tgcggttttg   2340
gcagtacatc aatgggcgtg gatagcggtt tgactcacgg ggatttccaa gtctccaccc   2400
cattgacgtc aatgggagtt tgttttggca ccaaaatcaa cgggactttc caaaatgtcg   2460
taacaactcc gccccattga cgcaaatggg cggtaggcgt gtacggtggg aggtctatat   2520
aagcagagct ggtttagtga accgtcagat ccgctagcat ggctgtcagc gacgcgctgc   2580
tcccatcttt ctccacgttc gcgtctggcc cggcgggaag ggagaagaca ctgcgtcaag   2640
caggtgcccc gaataaccgc tggcgggagg agctctccca catgaagcga cttcccccag   2700
tgcttcccgg ccgcccctat gacctggcgg cggcgaccgt ggccacagac ctggagagcg   2760
gcggagccgg tgcggcttgc ggcggtagca acctggcgcc cctacctcgg agagagaccg   2820
aggagttcaa cgatctcctg gacctggact ttattctctc caattcgctg acccatcctc   2880
cggagtcagt ggccgccacc gtgtcctcgt cagcgtcagc ctcctcttcg tcgtcgccgt   2940
cgagcagcgg ccctgccagc gcgccctcca cctgcagctt cacctatccg atccgggccg   3000
```

-continued

```
ggaacgaccc gggcgtggcg ccgggcggca cgggcggagg cctcctctat ggcagggagt   3060
ccgctccccc tccgacggct cccttcaacc tggcggacat caacgacgtg agcccctcgg   3120
gcggcttcat ggccgagctc ctgcggccag aattggaccc ggtgtacatt ccgccgcagc   3180
agccgcagcc gccaggtggc gggctgatgg gcaagttcgt gctgaaggcg tcgctgagcg   3240
cccctggcag cgagtacggc agcccgtcgg tcatcagcgt cagcaaaggc agccctgacg   3300
gcagccaccc ggtggtggtg gcgccctaca acggcgggcc gccgcgcacg tgccccaaga   3360
tcaagcagga ggcggtctct tcgtgcaccc acttgggcgc tggacccccct ctcagcaatg   3420
gccaccggcc ggctgcacac gacttccccc tggggcggca gctccccagc aggactaccc   3480
cgaccctggg tcttgaggaa gtgctgagca gcagggactg tcaccctgcc ctgccgcttc   3540
ctcccggctt ccatccccac ccggggccca attacccatc cttcctgccc gatcagatgc   3600
agccgcaagt cccgccgctc cattaccaag agctcatgcc acccggttcc tgcatgccag   3660
aggagcccaa gccaaagagg ggaagacgat cgtggccccg gaaaaggacc gccacccaca   3720
cttgtgatta cgcgggctgc ggcaaaacct acacaaagag ttcccatctc aaggcacacc   3780
tgcgaaccca cacaggtgag aaaccttacc actgtgactg ggacggctgt ggatggaaat   3840
tcgcccgctc agatgaactg accaggcact accgtaaaca cacggggcac cgcccgttcc   3900
agtgccaaaa atgcgaccga gcattttcca ggtcggacca cctcgcctta cacatgaaga   3960
ggcattttta agctagcgct accggactca gatcggccgc gactctagat cataatcagc   4020
cataccacat ttgtagaggt tttacttgct ttaaaaaacc tcccacacct ccccctgaac   4080
ctgaaacata aaatgaatgc aattgttgtt gttaacttgt ttattgcagc ttataatggt   4140
tacaaataaa gcaatagcat cacaaatttc acaaataaag catttttttc actgcattct   4200
agttgtggtt tgtccaaact catcaatgta tcttaatcga cgcggcctaa tagtaatcaa   4260
ttacggggtc attagttcat agcccatata tggagttccg cgttacataa cttacggtaa   4320
atggcccgcc tggctgaccg cccaacgacc cccgcccatt gacgtcaata atgacgtatg   4380
ttcccatagt aacgccaata gggactttcc attgacgtca atgggtggag tatttacggt   4440
aaactgccca cttggcagta catcaagtgt atcatatgcc aagtacgccc cctattgacg   4500
tcaatgacgg taaatggccc gcctggcatt atgcccagta catgacctta tgggactttc   4560
ctacttggca gtacatctac gtattagtca tcgctattac catggtgatg cggttttggc   4620
agtacatcaa tgggcgtgga tagcggtttg actcacgggg atttccaagt ctccacccca   4680
ttgacgtcaa tgggagtttg ttttggcacc aaaatcaacg ggactttcca aaatgtcgta   4740
acaactccgc cccattgacg caaatgggcg gtaggcgtgt acggtgggag gtctatataa   4800
gcagagctgg tttagtgaac cgtcagatcc gctagcatgc ccctcaacgt tagcttcacc   4860
aacaggaact atgacctcga ctacgactcg gtgcagccgt atttctactg cgacgaggag   4920
gagaacttct accagcagca gcagcagagc gagctgcagc ccccggcgcc cagcgaggat   4980
atctggaaga aattcgagct gctgcccacc ccgcccctgt cccctagccg ccgctccggg   5040
ctctgctcgc cctcctacgt tgcggtcaca cccttctccc ttcggggaga caacgacggc   5100
ggtggcggga gcttctccac ggccgaccag ctggagatgg tgaccgagct gctgggagga   5160
gacatggtga accagagttt catctgcgac ccggacgacg agaccttcat caaaaacatc   5220
atcatccagg actgtatgtg gagcggcttc tcggccgccg ccaagctcgt ctcagagaag   5280
ctggcctcct accaggctgc gcgcaaagac agcggcagcc cgaaccccgc ccgcggccac   5340
```

```
agcgtctgct ccacctccag cttgtacctg caggatctga gcgccgccgc ctcagagtgc   5400
atcgacccct cggtggtctt cccctaccct ctcaacgaca gcagctcgcc caagtcctgc   5460
gcctcgcaag actccagcgc cttctctccg tcctcggatt ctctgctctc ctcgacggag   5520
tcctccccgc agggcagccc cgagcccctg gtgctccatg aggagacacc gcccaccacc   5580
agcagcgact ctgaggagga acaagaagat gaggaagaaa tcgatgttgt ttctgtggaa   5640
aagaggcagg ctcctggcaa aaggtcagag tctggatcac cttctgctgg aggccacagc   5700
aaacctcctc acagcccact ggtcctcaag aggtgccacg tctccacaca tcagcacaac   5760
tacgcagcgc ctccctccac tcggaaggac tatcctgctg ccaagagggt caagttggac   5820
agtgtcagag tcctgagaca gatcagcaac aaccgaaaat gcaccagccc caggtcctcg   5880
gacaccgagg agaatgtcaa gaggcgaaca cacaacgtct tggagcgcca gaggaggaac   5940
gagctaaaac ggagcttttt tgccctgcgt gaccagatcc cggagttgga aaacaatgaa   6000
aaggccccca aggtagttat ccttaaaaaa gccacagcat acatcctgtc cgtccaagca   6060
gaggagcaaa agctcatttc tgaagaggac ttgttgcgga aacgacgaga acagttgaaa   6120
cacaaacttg aacagctacg gaactcttgt gcgtaagcta gcgctaccgg actcagatcg   6180
gccgcgactc tagatcataa tcagccatac cacatttgta gaggttttac ttgctttaaa   6240
aaacctccca cacctccccc tgaacctgaa acataaaatg aatgcaattg ttgttgttaa   6300
cttgtttatt gcagcttata atggttacaa ataaagcaat agcatcacaa atttcacaaa   6360
taaagcattt ttttcactgc attctagttg tggtttgtcc aaactcatca atgtatctta   6420
aggccgcgat taatagtaat caattacggg gtcattagtt catagcccat atatggagtt   6480
ccgcgttaca taacttacgg taaatggccc gcctggctga ccgcccaacg acccccgccc   6540
attgacgtca ataatgacgt atgttcccat agtaacgcca atagggactt tccattgacg   6600
tcaatgggtg gagtatttac ggtaaactgc ccacttggca gtacatcaag tgtatcatat   6660
gccaagtacg ccccctattg acgtcaatga cggtaaatgg cccgcctggc attatgccca   6720
gtacatgacc ttatgggact ttcctacttg gcagtacatc tacgtattag tcatcgctat   6780
taccatggtg atgcggtttt ggcagtacat caatgggcgt ggatagcggt ttgactcacg   6840
gggatttcca agtctccacc ccattgacgt caatgggagt ttgttttggc accaaaatca   6900
acgggacttt ccaaaatgtc gtaacaactc cgccccattg acgcaaatgg gcggtaggcg   6960
tgtacggtgg gaggtctata taagcagagc tggtttagtg aaccgtcaga tccgctagca   7020
tggcgggaca cctggcttcg gatttcgcct tctcgccccc tccaggtggt ggaggtgatg   7080
ggccaggggg gccggagccg ggctgggttg atcctcggac ctggctaagc ttccaaggcc   7140
ctcctggagg gccaggaatc gggccggggg ttgggccagg ctctgaggtg tgggggattc   7200
ccccatgccc cccgccgtat gagttctgtg gggggatggc gtactgtggg ccccaggttg   7260
gagtggggct agtgccccaa ggcggcttgg agacctctca gcctgagggt gaagcangag   7320
tcggggtgga gagcaactcc gatggggcct ccccggagcc ctgcaccgtc acccctggtg   7380
ccgtgaagct ggagaaggag aagctggagc aaaacccgga ggagtcccag gacatcaaag   7440
ctctgcagaa agaactcgag caatttgcca agctcctgaa gcagaagagg atcaccctgg   7500
gatatacaca ggccgatgtg gggctcaccc tgggggttct atttgggaag gtattcagcc   7560
aaacgaccat ctgccgcttt gaggctctgc agcttagctt caagaacatg tgtaagctgc   7620
ggcccttgct gcagaagtgg gtggaggaag ctgacaacaa tgaaaatctt caggagatat   7680
gcaaagcaga aaccctcgtg caggcccgaa agagaaagcg aaccagtatc gagaaccgag   7740
```

```
tgagaggcaa cctggagaat ttgttcctgc agtgcccgaa acccacactg cagcagatca   7800
gccacatcgc ccagcagctt gggctcgaga aggatgtggt ccgagtgtgg ttctgtaacc   7860
ggcgccagaa gggcaagcga tcaagcagcg actatgcaca acgagaggat tttgaggctg   7920
ctgggtctcc tttctcaggg ggaccagtgt cctttcctct ggccccaggg ccccattttg   7980
gtaccccagg ctatgggagc cctcacttca ctgcactgta ctcctcggtc cctttccctg   8040
agggggaagc ctttcccccct gtctccgtca ccactctggg ctctcccatg cattcaaact   8100
gagctagcgc taccggactc agatcggccg cgactctaga tcataatcag ccataccaca   8160
tttgtagagg ttttacttgc tttaaaaaac ctcccacacc tcccccctgaa cctgaaacat   8220
aaaatgaatg caattgttgt tgttaacttg tttattgcag cttataatgg ttacaaataa   8280
agcaatagca tcacaaattt cacaaataaa gcattttttt cactgcattc tagttgtggt   8340
ttgtccaaac tcatcaatgt atcttaaatc ctcgagaagc ttaatagtaa tcaattacgg   8400
ggtcattagt tcatagccca tatatggagt tccgcgttac ataacttacg gtaaatggcc   8460
cgcctggctg accgcccaac gacccccgcc cattgacgtc aataatgacg tatgttccca   8520
tagtaacgcc aatagggact ttccattgac gtcaatgggt ggagtattta cggtaaactg   8580
cccacttggc agtacatcaa gtgtatcata tgccaagtac gccccctatt gacgtcaatg   8640
acggtaaatg gcccgcctgg cattatgccc agtacatgac cttatgggac tttcctactt   8700
ggcagtacat ctacgtatta gtcatcgcta ttaccatggt gatgcggttt tggcagtaca   8760
tcaatgggcg tggatagcgg tttgactcac ggggatttcc aagtctccac cccattgacg   8820
tcaatgggag tttgttttgg caccaaaatc aacgggactt tccaaaatgt cgtaacaact   8880
ccgccccatt gacgcaaatg ggcggtaggc gtgtacggtg ggaggtctat ataagcagag   8940
ctggtttagt gaaccgtcag atccgctagc atgtacaaca tgatggagac ggagctgaag   9000
ccgccgggcc cgcagcaaac ttcgggggc ggcggcggca actccaccgc ggcggcggcc   9060
ggcggcaacc agaaaaacag cccggaccgc gtcaagcggc ccatgaatgc cttcatggtg   9120
tggtcccgcg ggcagcggcg caagatggcc caggagaacc ccaagatgca caactcggag   9180
atcagcaagc gcctgggcgc cgagtggaaa cttttgtcgg agacggagaa gcggccgttc   9240
atcgacgagg ctaagcggct gcgagcgctg cacatgaagg agcacccgga ttataaatac   9300
cggccccggc ggaaaaccaa gacgctcatg aagaaggata agtacacgct gcccggcggg   9360
ctgctggccc ccggcggcaa tagcatggcg agcggggtcg gggtgggcgc cggcctgggc   9420
gcgggcgtga accagcgcat ggacagttac gcgcacatga acggctggag caacggcagc   9480
tacagcatga tgcaggacca gctgggctac ccgcagcacc cgggcctcaa tgcgcacggc   9540
gcagcgcaga tgcagcccat gcaccgctac gacgtgagcg ccctgcagta caactccatg   9600
accagctcgc agacctacat gaacggctcg cccacctaca gcatgtccta ctcgcagcag   9660
ggcacccctg gcatggctct tggctccatg ggttcggtgg tcaagtccga ggccagctcc   9720
agccccccctg tggttacctc ttcctcccac tccagggcgc cctgccaggc cggggacctc   9780
cgggacatga tcagcatgta tctccccggc gccgaggtgc cggaacccgc cgcccccagc   9840
agacttcaca tgtcccagca ctaccagagc ggcccggtgc ccggcacggc cattaacggc   9900
acactgcccc tctcacacat gtgagctagc gctaccggac tcagatcggc cgcgactcta   9960
gatcataatc agccatacca catttgtaga ggttttactt gctttaaaaa acctcccaca  10020
cctcccccctg aacctgaaac ataaaatgaa tgcaattgtt gttgttaact tgtttattgc  10080
```

```
agcttataat ggttacaaat aaagcaatag catcacaaat ttcacaaata aagcattttt  10140
ttcactgcat tctagttgtg gtttgtccaa actcatcaat gtatcttaaa gctttctaga  10200
gnnntaaggg tgggaaagaa tatataaggt gggggtctta tgtagttttg tatctgtttt  10260
gcagcagccg ccgccgccat gagcaccaac tcgtttgatg gaagcattgt gagctcatat  10320
ttgacaacgc gcatgccccc atgggccggg gtgcgtcaga atgtgatggg ctccagcatt  10380
gatggtcgcc ccgtcctgcc cgcaaactct actaccttga cctacgagac cgtgtctgga  10440
acgccgttgg agactgcagc ctccgccgcc gcttcagccg ctgcagccac cgcccgcggg  10500
attgtgactg actttgcttt cctgagcccg cttgcaagca gtgcagcttc ccgttcatcc  10560
gcccgcgatg acaagttgac ggctcttttg gcacaattgg attctttgac ccgggaactt  10620
aatgtcgttt ctcagcagct gttggatctg cgccagcagg tttctgccct gaaggcttcc  10680
tcccctccca atgcggttta aaacataaat aaaaaaccag actctgtttg gatttggatc  10740
aagcaagtgt cttgctgtct ttatttaggg gttttgcgcg cgcggtaggc ccgggaccag  10800
cggtctcggt cgttgagggt cctgtgtatt ttttccagga cgtggtaaag gtgactctgg  10860
atgttcagat acatgggcat aagcccgtct ctggggtgga ggtagcacca ctgcagagct  10920
tcatgctgcg gggtggtgtt gtagatgatc cagtcgtagc aggagcgctg ggcgtggtgc  10980
ctaaaaatgt ctttcagtag caagctgatt gccaggggca ggcccttggt gtaagtgttt  11040
acaaagcggt taagctggga tgggtgcata cgtggggata tgagatgcat cttggactgt  11100
atttttaggt tggctatgtt cccagccata tccctccggg gattcatgtt gtgcagaacc  11160
accagcacag tgtatccggt gcacttggga aatttgtcat gtagcttaga aggaaatgcg  11220
tggaagaact tggagacgcc cttgtgacct ccaagatttt ccatgcattc gtccataatg  11280
atggcaatgg gcccacgggc ggcggcctgg gcgaagatat ttctgggatc actaacgtca  11340
tagttgtgtt ccaggatgag atcgtcatag gccattttta caaagcgcgg gcggagggtg  11400
ccagactgcg gtataatggt tccatccggc ccaggggcgt agttaccctc acagatttgc  11460
atttcccacg ctttgagttc agatgggggg atcatgtcta cctgcggggc gatgaagaaa  11520
acggtttccg ggtaggggga gatcagctgg gaagaaagca ggttcctgag cagctgcgac  11580
ttaccgcagc cggtgggccc gtaaatcaca cctattaccg ggtgcaactg gtagttaaga  11640
gagctgcagc tgccgtcatc cctgagcagg ggggccactt cgttaagcat gtccctgact  11700
cgcatgtttt ccctgaccaa atccgccaga aggcgctcgc cgcccagcga tagcagttct  11760
tgcaaggaag caaagttttt caacggtttg agaccgtccg ccgtaggcat gcttttgagc  11820
gtttgaccaa gcagttccag gcggtcccac agctcggtca cctgctctac ggcatctcga  11880
tccagcatat ctcctcgttt cgcgggttgg ggcggctttc gctgtacggc agtagtcggt  11940
gctcgtccag acgggccagg gtcatgtctt tccacgggcg cagggtcctc gtcagcgtag  12000
tctgggtcac ggtgaagggg tgcgctccgg gctgcgcgct ggccagggtg cgcttgaggc  12060
tggtcctgct ggtgctgaag cgctgccggt cttcgccctg cgcgtcggcc aggtagcatt  12120
tgaccatggt gtcatagtcc agcccctccg cggcgtggcc cttggcgcgc agcttgccct  12180
tggaggaggc gccgcacgag gggcagtgca gacttttgag ggcgtagagc ttgggcgcga  12240
gaaataccga ttccggggag taggcatccg cgccgcaggc cccgcagacg gtctcgcatt  12300
ccacgagcca ggtgagctct ggccgttcgg ggtcaaaaac caggtttccc ccatgctttt  12360
tgatgcgttt cttacctctg gtttccatga gccggtgtcc acgctcggtg acgaaaaggc  12420
tgtccgtgtc cccgtataca gactnnngtt taaacgaatt cnnntataaa atgcaaggtg  12480
```

```
ctgctcaaaa aatcaggcaa agcctcgcgc aaaaaagaaa gcacatcgta gtcatgctca  12540
tgcagataaa ggcaggtaag ctccggaacc accacagaaa aagacaccat ttttctctca  12600
aacatgtctg cgggtttctg cataaacaca aaataaaata acaaaaaaac atttaaacat  12660
tagaagcctg tcttacaaca ggaaaaacaa cccttataag cataagacgg actacggcca  12720
tgccggcgtg accgtaaaaa aactggtcac cgtgattaaa aagcaccacc gacagctcct  12780
cggtcatgtc cggagtcata atgtaagact cggtaaacac atcaggttga ttcatcggtc  12840
agtgctaaaa agcgaccgaa atagcccggg ggaatacata cccgcaggcg tagagacaac  12900
attacagccc ccataggagg tataacaaaa ttaataggag agaaaaacac ataaacacct  12960
gaaaaaccct cctgcctagg caaaatagca ccctcccgct ccagaacaac atacagcgct  13020
tcacagcggc agcctaacag tcagccttac cagtaaaaaa gaaaacctat taaaaaaaca  13080
ccactcgaca cggcaccagc tcaatcagtc acagtgtaaa aaagggccaa gtgcagagcg  13140
agtatatata ggactaaaaa atgacgtaac ggttaaagtc cacaaaaaac acccagaaaa  13200
ccgcacgcga acctacgccc agaaacgaaa gccaaaaaac ccacaacttc ctcaaatcgt  13260
cacttccgtt ttcccacgtt acgtaacttc ccattttaag aaaactacaa ttcccaacac  13320
atacaagtta ctccgcccta aaacctacgt cacccgcccc gttcccacgc cccgcgccac  13380
gtcacaaact ccacccccctc attatcatat tggcttcaat ccaaaataag gtatattatt  13440
gatgatnnnt taattaagga tccnnncggt gtgaaatacc gcacagatgc gtaaggagaa  13500
aataccgcat caggcgctct tccgcttcct cgctcactga ctcgctgcgc tcggtcgttc  13560
ggctgcggcg agcggtatca gctcactcaa aggcggtaat acggttatcc acagaatcag  13620
gggataacgc aggaaagaac atgtgagcaa aaggccagca aaaggccagg aaccgtaaaa  13680
aggccgcgtt gctggcgttt ttccataggc tccgcccccc tgacgagcat cacaaaaatc  13740
gacgctcaag tcagaggtgg cgaaacccga caggactata aagataccag gcgtttcccc  13800
ctggaagctc cctcgtgcgc tctcctgttc cgaccctgcc gcttaccgga tacctgtccg  13860
cctttctccc ttcgggaagc gtggcgcttt ctcatagctc acgctgtagg tatctcagtt  13920
cggtgtaggt cgttcgctcc aagctgggct gtgtgcacga accccccgtt cagcccgacc  13980
gctgcgcctt atccggtaac tatcgtcttg agtccaaccc ggtaagacac gacttatcgc  14040
cactggcagc agccactggt aacaggatta gcagagcgag gtatgtaggc ggtgctacag  14100
agttcttgaa gtggtggcct aactacggct acactagaag gacagtattt ggtatctgcg  14160
ctctgctgaa gccagttacc ttcggaaaaa gagttggtag ctcttgatcc ggcaaacaaa  14220
ccaccgctgg tagcggtggt ttttttgttt gcaagcagca gattacgcgc agaaaaaaag  14280
gatctcaaga agatcctttg atcttttcta cggggtctga cgctcagtgg aacgaaaact  14340
cacgttaagg gattttggtc atgagattat caaaaaggat cttcacctag atccttttaa  14400
attaaaaatg aagttttaaa tcaatctaaa gtatatatga gtaaacttgg tctgacagtt  14460
accaatgctt aatcagtgag gcacctatct cagcgatctg tctatttcgt tcatccatag  14520
ttgcctgact ccccgtcgtg tagataacta cgatacggga gggcttacca tctggcccca  14580
gtgctgcaat gataccgcga gacccacgct caccggctcc agatttatca gcaataaacc  14640
agccagccgg aagggccgag cgcagaagtg gtcctgcaac tttatccgcc tccatccagt  14700
ctattaattg ttgccgggaa gctagagtaa gtagttcgcc agttaatagt ttgcgcaacg  14760
ttgttgnnnn nnaaaaagga tcttcaccta gatccttttc acgtagaaag ccagtccgca  14820
```

-continued

```
gaaacggtgc tgaccccgga tgaatgtcag ctactgggct atctggacaa gggaaaacgc  14880

aagcgcaaag agaaagcagg tagcttgcag tgggcttaca tggcgatagc tagactgggc  14940

ggttttatgg acagcaagcg aaccggaatt gccagctggg gcgccctctg gtaaggttgg  15000

gaagccctgc aaagtaaact ggatggcttt ctcgccgcca aggatctgat ggcgcagggg  15060

atcaagctct gatcaagaga caggatgagg atcgtttcgc atgattgaac aagatggatt  15120

gcacgcaggt tctccggccg cttgggtgga gaggctattc ggctatgact gggcacaaca  15180

gacaatcggc tgctctgatg ccgccgtgtt ccggctgtca gcgcaggggc gcccggttct  15240

ttttgtcaag accgacctgt ccggtgccct gaatgaactg caagacgagg cagcgcggct  15300

atcgtggctg gccacgacgg gcgttccttg cgcagctgtg ctcgacgttg tcactgaagc  15360

gggaagggac tggctgctat tgggcgaagt gccggggcag gatctcctgt catctcacct  15420

tgctcctgcc gagaaagtat ccatcatggc tgatgcaatg cggcggctgc atacgcttga  15480

tccggctacc tgcccattcg accaccaagc gaaacatcgc atcgagcgag cacgtactcg  15540

gatggaagcc ggtcttgtcg atcaggatga tctggacgaa gagcatcagg ggctcgcgcc  15600

agccgaactg ttcgccaggc tcaaggcgag catgcccgac ggcgaggatc tcgtcgtgac  15660

ccatggcgat gcctgcttgc cgaatatcat ggtggaaaat ggccgctttt ctggattcat  15720

cgactgtggc cggctgggtg tggcggaccg ctatcaggac atagcgttgg ctacccgtga  15780

tattgctgaa gagcttggcg gcgaatgggc tgaccgcttc ctcgtgcttt acggtatcgc  15840

cgctcccgat tcgcagcgca tcgccttcta tcgccttctt gacgagttct tctgaatttt  15900

gttaaaattt ttgttaaatc agctcatttt ttaaccaata ggccgaaatc ggcaacatcc  15960

cttataaatc aaaagaatag accgcgatag ggttgagtgt tgttccagtt tggaacaaga  16020

gtccactatt aaagaacgtg gactccaacg tcaaagggcg aaaaaccgtc tatcagggcg  16080

atggcccact acgtgaacca tcacccaaat caagtttttt gcggtcgagg tgccgtaaag  16140

ctctaaatcg gaaccctaaa gggagccccc gatttagagc ttgacgggga aagccggcga  16200

acgtggcgag aaaggaaggg aagaaagcga aaggagcggg cgctagggcg ctggcaagtg  16260

tagcggtcac gctgcgcgta accaccacac ccgcgcgctt aatgcgccg             16309
```

```
<210> SEQ ID NO 2
<211> LENGTH: 14736
<212> TYPE: DNA
<213> ORGANISM: Artificial Sequence
<220> FEATURE:
<223> OTHER INFORMATION: The adeno shuttle vector containing multi-RFs
      under CMV weak promoter (CMVWP) has been provided as
      pAd(CMVWP)-GFP-cMKSO (cM; c-Myc, K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (7564)..(7564)
<223> OTHER INFORMATION: n is a, c, g, or t
<220> FEATURE:
<221> NAME/KEY: misc_feature
<222> LOCATION: (8622)..(8624)
<223> OTHER INFORMATION: n is a, c, g, or t
```

<220> FEATURE:
<221> NAME/KEY: misc_feature
<222> LOCATION: (10865)..(10867)
<223> OTHER INFORMATION: n is a, c, g, or t
<220> FEATURE:
<221> NAME/KEY: misc_feature
<222> LOCATION: (10882)..(10884)
<223> OTHER INFORMATION: n is a, c, g, or t
<220> FEATURE:
<221> NAME/KEY: misc_feature
<222> LOCATION: (11867)..(11869)
<223> OTHER INFORMATION: n is a, c, g, or t
<220> FEATURE:
<221> NAME/KEY: misc_feature
<222> LOCATION: (11884)..(11886)
<223> OTHER INFORMATION: n is a, c, g, or t
<220> FEATURE:
<221> NAME/KEY: misc_feature
<222> LOCATION: (13187)..(13192)
<223> OTHER INFORMATION: n is a, c, g, or t
<220> FEATURE:
<221> NAME/KEY: misc_feature
<222> LOCATION: (14730)..(14736)
<223> OTHER INFORMATION: n is a, c, g, or t

<400> SEQUENCE: 2
nnnttaatta annntccctt ccagctctct gccccttttg gattgaagcc aatatgataa 60
tgagggggtg gagtttgtga cgtggcgcgg ggcgtgggaa cggggcgggt gacgtagtag 120
tgtggcggaa gtgtgatgtt gcaagtgtgg cggaacacat gtaagcgacg gatgtggcaa 180
aagtgacgtt tttggtgtgc gccggtgtac acaggaagtg acaattttcg cgcggtttta 240
ggcggatgtt gtagtaaatt tgggcgtaac cgagtaagat ttggccattt tcgcgggaaa 300
actgaataag aggaagtgaa atctgaataa ttttgtgtta ctcatagcgc gtaannnggt 360
accgcggcct aatagtaatc aattacgggg tcattagttc atagcccata tatggagttc 420
cgcgttacat aacttacggt aaatggcccg cctggctgac cgcccaacga cccccgccca 480
ttgacgtcaa tgggagtttg ttttggcacc aaaatcaacg ggactttcca aaatgtcgta 540
acaactccgc cccattgacg caaatgggcg gtaggcgtgt acggtgggag gtctatataa 600
gcagagctgg tttagtgaac cgtcagatcc gctagcgcta ccggactcag atctcgagct 660
caagcttcga attctgcagt cgacggtacc gcgggcccgg gatccaccgg tcgccaccat 720
ggtgagcaag ggcgaggagc tgttcaccgg ggtggtgccc atcctggtcg agctggacgg 780
cgacgtaaac ggccacaagt tcagcgtgtc cggcgagggc gagggcgatg ccacctacgg 840
caagctgacc ctgaagttca tctgcaccac cggcaagctg cccgtgccct ggcccaccct 900
cgtgaccacc ctgacctacg gcgtgcagtg cttcagccgc taccccgacc acatgaagca 960
gcacgacttc ttcaagtccg ccatgcccga aggctacgtc caggagcgca ccatcttctt 1020
caaggacgac ggcaactaca agacccgcgc cgaggtgaag ttcgagggcg acaccctggt 1080
gaaccgcatc gagctgaagg gcatcgactt caaggaggac ggcaacatcc tggggcacaa 1140
gctggagtac aactacaaca gccacaacgt ctatatcatg gccgacaagc agaagaacgg 1200
catcaaggtg aacttcaaga tccgccacaa catcgaggac ggcagcgtgc agctcgccga 1260
ccactaccag cagaacaccc ccatcggcga cggccccgtg ctgctgcccg acaaccacta 1320
cctgagcacc cagtccgccc tgagcaaaga ccccaacgag aagcgcgatc acatggtcct 1380
gctggagttc gtgaccgccg ccgggatcac tctcggcatg gacgagctgt acaagtaaag 1440
cggccgcgac tctagatcat aatcagccat accacatttg tagaggtttt acttgcttta 1500
aaaaacctcc cacacctccc cctgaacctg aaacataaaa tgaatgcaat tgttgttgtt 1560

```
aacttgttta ttgcagctta taatggttac aaataaagca atagcatcac aaatttcaca   1620
aataaagcat ttttttcact gcattctagt tgtggtttgt ccaaactcat caatgtatct   1680
taaggccgcc tcgagtctag aagtaatcaa ttacggggtc attagttcat agcccatata   1740
tggagttccg cgttacataa cttacggtaa atggcccgcc tggctgaccg cccaacgacc   1800
cccgcccatt gacgtcaatg ggagtttgtt ttggcaccaa aatcaacggg actttccaaa   1860
atgtcgtaac aactccgccc cattgacgca aatgggcggt aggcgtgtac ggtgggaggt   1920
ctatataagc agagctggtt tagtgaaccg tcagatccgc tagcatgccc ctcaacgtta   1980
gcttcaccaa caggaactat gacctcgact acgactcggt gcagccgtat ttctactgcg   2040
acgaggagga gaacttctac cagcagcagc agcagagcga gctgcagccc ccggcgccca   2100
gcgaggatat ctggaagaaa ttcgagctgc tgcccacccc gcccctgtcc cctagccgcc   2160
gctccgggct ctgctcgccc tcctacgttg cggtcacacc cttctccctt cggggagaca   2220
acgacggcgg tggcgggagc ttctccacgg ccgaccagct ggagatggtg accgagctgc   2280
tgggaggaga catggtgaac cagagtttca tctgcgaccc ggacgacgag accttcatca   2340
aaaacatcat catccaggac tgtatgtgga gcggcttctc ggccgccgcc aagctcgtct   2400
cagagaagct ggcctcctac caggctgcgc gcaaagacag cggcagcccg aaccccgccc   2460
gcggccacag cgtctgctcc acctccagct tgtacctgca ggatctgagc gccgccgcct   2520
cagagtgcat cgacccctcg gtggtcttcc cctaccctct caacgacagc agctcgccca   2580
agtcctgcgc ctcgcaagac tccagcgcct tctctccgtc ctcggattct ctgctctcct   2640
cgacggagtc ctccccgcag ggcagccccg agcccctggt gctccatgag gagacaccgc   2700
ccaccaccag cagcgactct gaggaggaac aagaagatga ggaagaaatc gatgttgttt   2760
ctgtggaaaa gaggcaggct cctggcaaaa ggtcagagtc tggatcacct tctgctggag   2820
gccacagcaa acctcctcac agcccactgg tcctcaagag gtgccacgtc tccacacatc   2880
agcacaacta cgcagcgcct ccctccactc ggaaggacta tcctgctgcc aagagggtca   2940
agttggacag tgtcagagtc ctgagacaga tcagcaacaa ccgaaaatgc accagcccca   3000
ggtcctcgga caccgaggag aatgtcaaga ggcgaacaca caacgtcttg gagcgccaga   3060
ggaggaacga gctaaaacgg agcttttttg ccctgcgtga ccagatcccg gagttggaaa   3120
acaatgaaaa ggcccccaag gtagttatcc ttaaaaaagc cacagcatac atcctgtccg   3180
tccaagcaga ggagcaaaag ctcatttctg aagaggactt gttgcggaaa cgacgagaac   3240
agttgaaaca caaacttgaa cagctacgga actcttgtgc gtaagctagc gctaccggac   3300
tcagatcggc cgcgactcta gatcataatc agccatacca catttgtaga ggttttactt   3360
gctttaaaaa acctcccaca cctccccctg aacctgaaac ataaaatgaa tgcaattgtt   3420
gttgttaact tgtttattgc agcttataat ggttacaaat aaagcaatag catcacaaat   3480
ttcacaaata aagcattttt ttcactgcat tctagttgtg gtttgtccaa actcatcaat   3540
gtattctaga gataattcag taatcaatta cggggtcatt agttcatagc ccatatatgg   3600
agttccgcgt tacataactt acggtaaatg gcccgcctgg ctgaccgccc aacgaccccc   3660
gcccattgac gtcaatggga gtttgttttg gcaccaaaat caacgggact ttccaaaatg   3720
tcgtaacaac tccgccccat tgacgcaaat gggcggtagg cgtgtacggt gggaggtcta   3780
tataagcaga gctggtttag tgaaccgtca gatccgctag catggctgtc agcgacgcgc   3840
tgctcccatc tttctccacg ttcgcgtctg gcccggcggg aagggagaag acactgcgtc   3900
aagcaggtgc ccgaataac cgctggcggg aggagctctc ccacatgaag cgacttcccc   3960
```

```
cagtgcttcc cggccgcccc tatgacctgg cggcggcgac cgtggccaca gacctggaga   4020
gcggcggagc cggtgcggct tgcggcggta gcaacctggc gcccctacct cggagagaga   4080
ccgaggagtt caacgatctc ctggacctgg actttattct ctccaattcg ctgacccatc   4140
ctccggagtc agtggccgcc accgtgtcct cgtcagcgtc agcctcctct tcgtcgtcgc   4200
cgtcgagcag cggccctgcc agcgcgccct ccacctgcag cttcacctat ccgatccggg   4260
ccgggaacga cccgggcgtg gcgccgggcg gcacgggcgg aggcctcctc tatggcaggg   4320
agtccgctcc ccctccgacg gctcccttca acctggcgga catcaacgac gtgagcccct   4380
cgggcggctt catggccgag ctcctgcggc cagaattgga cccggtgtac attccgccgc   4440
agcagccgca gccgccaggt ggcgggctga tgggcaagtt cgtgctgaag gcgtcgctga   4500
gcgcccctgg cagcgagtac ggcagcccgt cggtcatcag cgtcagcaaa ggcagccctg   4560
acggcagcca cccggtggtg gtggcgccct acaacggcgg gccgccgcgc acgtgcccca   4620
agatcaagca ggaggcggtc tcttcgtgca cccacttggg cgctggaccc cctctcagca   4680
atggccaccg gccggctgca cacgacttcc ccctggggcg gcagctcccc agcaggacta   4740
ccccgaccct gggtcttgag gaagtgctga gcagcaggga ctgtcaccct gccctgccgc   4800
ttcctcccgg cttccatccc cacccggggc ccaattaccc atccttcctg cccgatcaga   4860
tgcagccgca agtcccgccg ctccattacc aagagctcat gccacccggt tcctgcatgc   4920
cagaggagcc caagccaaag aggggaagac gatcgtggcc ccggaaaagg accgccaccc   4980
acacttgtga ttacgcgggc tgcggcaaaa cctacacaaa gagttcccat ctcaaggcac   5040
acctgcgaac ccacacaggt gagaaacctt accactgtga ctgggacggc tgtggatgga   5100
aattcgcccg ctcagatgaa ctgaccaggc actaccgtaa acacacgggg caccgcccgt   5160
tccagtgcca aaaatgcgac cgagcatttt ccaggtcgga ccacctcgcc ttacacatga   5220
agaggcattt ttaagctagc gctaccggac tcagatcggc cgcgactcta gatcataatc   5280
agccatacca catttgtaga ggttttactt gctttaaaaa acctcccaca cctccccctg   5340
aacctgaaac ataaaatgaa tgcaattgtt gttgttaact tgtttattgc agcttataat   5400
ggttacaaat aaagcaatag catcacaaat ttcacaaata aagcattttt ttcactgcat   5460
tctagttgtg gtttgtccaa actcatcaat gtatgaatta tcgaattcaa gcttagtaat   5520
caattacggg gtcattagtt catagcccat atatggagtt ccgcgttaca taacttacgg   5580
taaatggccc gcctggctga ccgcccaacg acccccgccc attgacgtca atgggagttt   5640
gttttggcac caaaatcaac gggactttcc aaaatgtcgt aacaactccg ccccattgac   5700
gcaaatgggc ggtaggcgtg tacggtggga ggtctatata agcagagctg gtttagtgaa   5760
ccgtcagatc cgctagcatg tacaacatga tggagacgga gctgaagccg ccgggcccgc   5820
agcaaacttc ggggggcggc ggcggcaact ccaccgcggc ggcggccggc ggcaaccaga   5880
aaaacagccc ggaccgcgtc aagcggccca tgaatgcctt catggtgtgg tcccgcgggc   5940
agcggcgcaa gatggcccag gagaacccca agatgcacaa ctcggagatc agcaagcgcc   6000
tgggcgccga gtggaaactt ttgtcggaga cggagaagcg gccgttcatc gacgaggcta   6060
agcggctgcg agcgctgcac atgaaggagc acccggatta taaataccgg ccccggcgga   6120
aaaccaagac gctcatgaag aaggataagt acacgctgcc cggcgggctg ctggcccccg   6180
gcggcaatag catggcgagc ggggtcgggg tgggcgccgg cctgggcgcg ggcgtgaacc   6240
agcgcatgga cagttacgcg cacatgaacg gctggagcaa cggcagctac agcatgatgc   6300
```

```
aggaccagct gggctacccg cagcacccgg gcctcaatgc gcacggcgca gcgcagatgc   6360
agcccatgca ccgctacgac gtgagcgccc tgcagtacaa ctccatgacc agctcgcaga   6420
cctacatgaa cggctcgccc acctacagca tgtcctactc gcagcagggc acccctggca   6480
tggctcttgg ctccatgggt tcggtggtca agtccgaggc cagctccagc cccccctgtgg  6540
ttacctcttc ctcccactcc agggcgccct gccaggccgg ggacctccgg gacatgatca   6600
gcatgtatct ccccggcgcc gaggtgccgg aacccgccgc ccccagcaga cttcacatgt   6660
cccagcacta ccagagcggc ccggtgcccg gcacggccat taacggcaca ctgcccctct   6720
cacacatgtg agctagcgct accggactca gatcggccgc gactctagat cataatcagc   6780
cataccacat ttgtagaggt tttacttgct ttaaaaaacc tcccacacct ccccctgaac   6840
ctgaaacata aaatgaatgc aattgttgtt gttaacttgt ttattgcagc ttataatggt   6900
tacaaataaa gcaatagcat cacaaatttc acaaataaag catttttttc actgcattct   6960
agttgtggtt tgtccaaact catcaatgta taagcttgtc gacagtaatc aattacgggg   7020
tcattagttc atagcccata tatggagttc cgcgttacat aacttacggt aaatggcccg   7080
cctggctgac cgcccaacga cccccgccca ttgacgtcaa tgggagtttg ttttggcacc   7140
aaaatcaacg ggactttcca aaatgtcgta acaactccgc cccattgacg caaatgggcg   7200
gtaggcgtgt acggtgggag gtctatataa gcagagctgg tttagtgaac cgtcagatcc   7260
gctagcatgg cgggacacct ggcttcggat ttcgccttct cgccccctcc aggtggtgga   7320
ggtgatgggc caggggggcc ggagccgggc tgggttgatc ctcggacctg gctaagcttc   7380
caaggccctc ctggagggcc aggaatcggg ccgggggttg ggccaggctc tgaggtgtgg   7440
gggattcccc catgcccccc gccgtatgag ttctgtgggg ggatggcgta ctgtgggccc   7500
caggttggag tggggctagt gccccaaggc ggcttggaga cctctcagcc tgagggtgaa   7560
gcangagtcg ggggtggagag caactccgat ggggcctccc cggagccctg caccgtcacc  7620
cctggtgccg tgaagctgga gaaggagaag ctggagcaaa acccggagga gtcccaggac   7680
atcaaagctc tgcagaaaga actcgagcaa tttgccaagc tcctgaagca gaagaggatc   7740
accctgggat atacacaggc cgatgtgggg ctcaccctgg gggttctatt tgggaaggta   7800
ttcagccaaa cgaccatctg ccgctttgag gctctgcagc ttagcttcaa gaacatgtgt   7860
aagctgcggc ccttgctgca gaagtgggtg gaggaagctg acaacaatga aaatcttcag   7920
gagatatgca aagcagaaac cctcgtgcag gcccgaaaga gaaagcgaac cagtatcgag   7980
aaccgagtga gaggcaacct ggagaatttg ttcctgcagt gcccgaaacc cacactgcag   8040
cagatcagcc acatcgccca gcagcttggg ctcgagaagg atgtggtccg agtgtggttc   8100
tgtaaccggc gccagaaggg caagcgatca agcagcgact atgcacaacg agaggatttt   8160
gaggctgctg ggtctccttt ctcaggggga ccagtgtcct ttcctctggc cccagggccc   8220
cattttggta ccccaggcta tgggagccct cacttcactg cactgtactc ctcggtccct   8280
ttccctgagg gggaagcctt tccccctgtc tccgtcacca ctctgggctc tcccatgcat   8340
tcaaactgag ctagcgctac cggactcaga tcggccgcga ctctagatca taatcagcca   8400
taccacattt gtagaggttt tacttgcttt aaaaaacctc ccacacctcc ccctgaacct   8460
gaaacataaa atgaatgcaa ttgttgttgt taacttgttt attgcagctt ataatggtta   8520
caaataaagc aatagcatca caaatttcac aaataaagca tttttttcac tgcattctag   8580
ttgtggtttg tccaaactca tcaatgtatg tcgacagatc tnnntaaggg tgggaaagaa   8640
tatataaggt gggggtctta tgtagttttg tatctgtttt gcagcagccg ccgccgccat   8700
```

```
gagcaccaac tcgtttgatg gaagcattgt gagctcatat ttgacaacgc gcatgccccc   8760
atgggccggg gtgcgtcaga atgtgatggg ctccagcatt gatggtcgcc ccgtcctgcc   8820
cgcaaactct actaccttga cctacgagac cgtgtctgga acgccgttgg agactgcagc   8880
ctccgccgcc gcttcagccg ctgcagccac cgcccgcggg attgtgactg actttgcttt   8940
cctgagcccg cttgcaagca gtgcagcttc ccgttcatcc gcccgcgatg acaagttgac   9000
ggctcttttg gcacaattgg attctttgac ccgggaactt aatgtcgttt ctcagcagct   9060
gttggatctg cgccagcagg tttctgccct gaaggcttcc tcccctccca atgcggttta   9120
aaacataaat aaaaaaccag actctgtttg gatttggatc aagcaagtgt cttgctgtct   9180
ttatttaggg gttttgcgcg cgcggtaggc ccgggaccag cggtctcggt cgttgagggt   9240
cctgtgtatt ttttccagga cgtggtaaag gtgactctgg atgttcagat acatgggcat   9300
aagcccgtct ctggggtgga ggtagcacca ctgcagagct tcatgctgcg gggtggtgtt   9360
gtagatgatc cagtcgtagc aggagcgctg ggcgtggtgc ctaaaaatgt ctttcagtag   9420
caagctgatt gccaggggca ggcccttggt gtaagtgttt acaaagcggt taagctggga   9480
tgggtgcata cgtggggata tgagatgcat cttggactgt atttttaggt tggctatgtt   9540
cccagccata tccctccggg gattcatgtt gtgcagaacc accagcacag tgtatccggt   9600
gcacttggga aatttgtcat gtagcttaga aggaaatgcg tggaagaact tggagacgcc   9660
cttgtgacct ccaagatttt ccatgcattc gtccataatg atggcaatgg gcccacgggc   9720
ggcggcctgg gcgaagatat ttctgggatc actaacgtca tagttgtgtt ccaggatgag   9780
atcgtcatag gccattttta caaagcgcgg gcggagggtg ccagactgcg gtataatggt   9840
tccatccggc ccaggggcgt agttaccctc acagatttgc atttcccacg ctttgagttc   9900
agatgggggg atcatgtcta cctgcggggc gatgaagaaa acggtttccg gggtagggga   9960
gatcagctgg gaagaaagca ggttcctgag cagctgcgac ttaccgcagc cggtgggccc  10020
gtaaatcaca cctattaccg ggtgcaactg gtagttaaga gagctgcagc tgccgtcatc  10080
cctgagcagg ggggccactt cgttaagcat gtccctgact cgcatgtttt ccctgaccaa  10140
atccgccaga aggcgctcgc cgcccagcga tagcagttct tgcaaggaag caaagttttt  10200
caacggtttg agaccgtccg ccgtaggcat gcttttgagc gtttgaccaa gcagttccag  10260
gcggtcccac agctcggtca cctgctctac ggcatctcga tccagcatat ctcctcgttt  10320
cgcgggttgg ggcggctttc gctgtacggc agtagtcggt gctcgtccag acgggccagg  10380
gtcatgtctt tccacgggcg cagggtcctc gtcagcgtag tctgggtcac ggtgaagggg  10440
tgcgctccgg gctgcgcgct ggccagggtg cgcttgaggc tggtcctgct ggtgctgaag  10500
cgctgccggt cttcgccctg cgcgtcggcc aggtagcatt tgaccatggt gtcatagtcc  10560
agcccctccg cggcgtggcc cttggcgcgc agcttgccct tggaggaggc gccgcacgag  10620
gggcagtgca gacttttgag ggcgtagagc ttgggcgcga gaaataccga ttccggggag  10680
taggcatccg cgccgcaggc cccgcagacg gtctcgcatt ccacgagcca ggtgagctct  10740
ggccgttcgg ggtcaaaaac caggtttccc ccatgctttt tgatgcgttt cttacctctg  10800
gtttccatga gccggtgtcc acgctcggtg acgaaaaggc tgtccgtgtc cccgtataca  10860
gactnnngtt taaacgaatt cnnntataaa atgcaaggtg ctgctcaaaa aatcaggcaa  10920
agcctcgcgc aaaaaagaaa gcacatcgta gtcatgctca tgcagataaa ggcaggtaag  10980
ctccggaacc accacagaaa aagacaccat ttttctctca aacatgtctg cgggtttctg  11040
```

```
cataaacaca aaataaaata acaaaaaaac atttaaacat tagaagcctg tcttacaaca  11100
ggaaaaacaa cccttataag cataagacgg actacggcca tgccggcgtg accgtaaaaa  11160
aactggtcac cgtgattaaa aagcaccacc gacagctcct cggtcatgtc cggagtcata  11220
atgtaagact cggtaaacac atcaggttga ttcatcggtc agtgctaaaa agcgaccgaa  11280
atagcccggg ggaatacata cccgcaggcg tagagacaac attacagccc ccataggagg  11340
tataacaaaa ttaataggag agaaaaacac ataaacacct gaaaaaccct cctgcctagg  11400
caaaatagca ccctcccgct ccagaacaac atacagcgct tcacagcggc agcctaacag  11460
tcagccttac cagtaaaaaa gaaaacctat taaaaaaaca ccactcgaca cggcaccagc  11520
tcaatcagtc acagtgtaaa aaagggccaa gtgcagagcg agtatatata ggactaaaaa  11580
atgacgtaac ggttaaagtc cacaaaaaac acccagaaaa ccgcacgcga acctacgccc  11640
agaaacgaaa gccaaaaaac ccacaacttc ctcaaatcgt cacttccgtt ttcccacgtt  11700
acgtaacttc ccattttaag aaaactacaa ttcccaacac atacaagtta ctccgcccta  11760
aaacctacgt cacccgcccc gttcccacgc cccgcgccac gtcacaaact ccaccccctc  11820
attatcatat tggcttcaat ccaaaataag gtatattatt gatgatnnnt taattaagga  11880
tccnnncggt gtgaaatacc gcacagatgc gtaaggagaa aataccgcat caggcgctct  11940
tccgcttcct cgctcactga ctcgctgcgc tcggtcgttc ggctgcggcg agcggtatca  12000
gctcactcaa aggcggtaat acggttatcc acagaatcag gggataacgc aggaaagaac  12060
atgtgagcaa aaggccagca aaaggccagg aaccgtaaaa aggccgcgtt gctggcgttt  12120
ttccataggc tccgcccccc tgacgagcat cacaaaaatc gacgctcaag tcagaggtgg  12180
cgaaacccga caggactata aagataccag gcgtttcccc ctggaagctc cctcgtgcgc  12240
tctcctgttc cgaccctgcc gcttaccgga tacctgtccg cctttctccc ttcgggaagc  12300
gtggcgcttt ctcatagctc acgctgtagg tatctcagtt cggtgtaggt cgttcgctcc  12360
aagctgggct gtgtgcacga accccccgtt cagcccgacc gctgcgcctt atccggtaac  12420
tatcgtcttg agtccaaccc ggtaagacac gacttatcgc cactggcagc agccactggt  12480
aacaggatta gcagagcgag gtatgtaggc ggtgctacag agttcttgaa gtggtggcct  12540
aactacggct acactagaag gacagtattt ggtatctgcg ctctgctgaa gccagttacc  12600
ttcggaaaaa gagttggtag ctcttgatcc ggcaaacaaa ccaccgctgg tagcggtggt  12660
ttttttgttt gcaagcagca gattacgcgc agaaaaaaag gatctcaaga agatcctttg  12720
atcttttcta cggggtctga cgctcagtgg aacgaaaact cacgttaagg gattttggtc  12780
atgagattat caaaaaggat cttcacctag atccttttaa attaaaaatg aagttttaaa  12840
tcaatctaaa gtatatatga gtaaacttgg tctgacagtt accaatgctt aatcagtgag  12900
gcacctatct cagcgatctg tctatttcgt tcatccatag ttgcctgact ccccgtcgtg  12960
tagataacta cgatacggga gggcttacca tctggcccca gtgctgcaat gataccgcga  13020
gacccacgct caccggctcc agatttatca gcaataaacc agccagccgg aagggccgag  13080
cgcagaagtg gtcctgcaac tttatccgcc tccatccagt ctattaattg ttgccgggaa  13140
gctagagtaa gtagttcgcc agttaatagt ttgcgcaacg ttgttgnnnn nnaaaaagga  13200
tcttcaccta gatccttttc acgtagaaag ccagtccgca gaaacggtgc tgaccccgga  13260
tgaatgtcag ctactgggct atctggacaa gggaaaacgc aagcgcaaag agaaagcagg  13320
tagcttgcag tgggcttaca tggcgatagc tagactgggc ggttttatgg acagcaagcg  13380
aaccggaatt gccagctggg gcgccctctg gtaaggttgg gaagccctgc aaagtaaact  13440
```

```
ggatggcttt ctcgccgcca aggatctgat ggcgcagggg atcaagctct gatcaagaga  13500

caggatgagg atcgtttcgc atgattgaac aagatggatt gcacgcaggt tctccggccg  13560

cttgggtgga gaggctattc ggctatgact gggcacaaca gacaatcggc tgctctgatg  13620

ccgccgtgtt ccggctgtca gcgcaggggc gcccggttct ttttgtcaag accgacctgt  13680

ccggtgccct gaatgaactg caagacgagg cagcgcggct atcgtggctg gccacgacgg  13740

gcgttccttg cgcagctgtg ctcgacgttg tcactgaagc gggaagggac tggctgctat  13800

tgggcgaagt gccggggcag gatctcctgt catctcacct tgctcctgcc gagaaagtat  13860

ccatcatggc tgatgcaatg cggcggctgc atacgcttga tccggctacc tgcccattcg  13920

accaccaagc gaaacatcgc atcgagcgag cacgtactcg gatggaagcc ggtcttgtcg  13980

atcaggatga tctggacgaa gagcatcagg ggctcgcgcc agccgaactg ttcgccaggc  14040

tcaaggcgag catgcccgac ggcgaggatc tcgtcgtgac ccatggcgat gcctgcttgc  14100

cgaatatcat ggtggaaaat ggccgctttt ctggattcat cgactgtggc cggctgggtg  14160

tggcggaccg ctatcaggac atagcgttgg ctacccgtga tattgctgaa gagcttggcg  14220

gcgaatgggc tgaccgcttc ctcgtgcttt acggtatcgc cgctcccgat tcgcagcgca  14280

tcgccttcta tcgccttctt gacgagttct tctgaatttt gttaaaattt ttgttaaatc  14340

agctcatttt ttaaccaata ggccgaaatc ggcaacatcc cttataaatc aaaagaatag  14400

accgcgatag ggttgagtgt tgttccagtt tggaacaaga gtccactatt aaagaacgtg  14460

gactccaacg tcaaagggcg aaaaaccgtc tatcagggcg atggcccact acgtgaacca  14520

tcacccaaat caagtttttt gcggtcgagg tgccgtaaag ctctaaatcg gaaccctaaa  14580

gggagccccc gatttagagc ttgacgggga aagccggcga acgtggcgag aaaggaaggg  14640

aagaaagcga aaggagcggg cgctagggcg ctggcaagtg tagcggtcac gctgcgcgta  14700

accaccacac ccgcgcgctt aatgcgccgn nnnnnn                           14736
```

```
<210> SEQ ID NO 3
<211> LENGTH: 13418
<212> TYPE: DNA
<213> ORGANISM: Artificial Sequence
<220> FEATURE:
<223> OTHER INFORMATION: The adeno shuttle vector containing multi-RFs
      under CMV weak promoter (CMVWP) has been provided as
      pAd(CMVWP)-cMKSO (cM; c-Myc, K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (6246)..(6246)
<223> OTHER INFORMATION: n is a, c, g, or t
<220> FEATURE:
<221> NAME/KEY: misc_feature
<222> LOCATION: (7304)..(7306)
<223> OTHER INFORMATION: n is a, c, g, or t
<220> FEATURE:
<221> NAME/KEY: misc_feature
<222> LOCATION: (9547)..(9549)
<223> OTHER INFORMATION: n is a, c, g, or t
<220> FEATURE:
```

<221> NAME/KEY: misc_feature
<222> LOCATION: (9564)..(9566)
<223> OTHER INFORMATION: n is a, c, g, or t
<220> FEATURE:
<221> NAME/KEY: misc_feature
<222> LOCATION: (10549)..(10551)
<223> OTHER INFORMATION: n is a, c, g, or t
<220> FEATURE:
<221> NAME/KEY: misc_feature
<222> LOCATION: (10566)..(10568)
<223> OTHER INFORMATION: n is a, c, g, or t
<220> FEATURE:
<221> NAME/KEY: misc_feature
<222> LOCATION: (11869)..(11874)
<223> OTHER INFORMATION: n is a, c, g, or t
<220> FEATURE:
<221> NAME/KEY: misc_feature
<222> LOCATION: (13412)..(13418)
<223> OTHER INFORMATION: n is a, c, g, or t

<400> SEQUENCE: 3

```
nnnttaatta annntccctt ccagctctct gccccttttg gattgaagcc aatatgataa     60

tgagggggtg gagtttgtga cgtggcgcgg ggcgtgggaa cggggcgggt gacgtagtag    120

tgtggcggaa gtgtgatgtt gcaagtgtgg cggaacacat gtaagcgacg gatgtggcaa    180

aagtgacgtt tttggtgtgc gccggtgtac acaggaagtg acaattttcg cgcggtttta    240

ggcggatgtt gtagtaaatt tgggcgtaac cgagtaagat ttggccattt tcgcgggaaa    300

actgaataag aggaagtgaa atctgaataa ttttgtgtta ctcatagcgc gtaannnggt    360

accgcggccg cctcgagtct agaagtaatc aattacgggg tcattagttc atagcccata    420

tatggagttc cgcgttacat aacttacggt aaatggcccg cctggctgac cgcccaacga    480

cccccgccca ttgacgtcaa tgggagtttg ttttggcacc aaaatcaacg ggactttcca    540

aaatgtcgta acaactccgc cccattgacg caaatgggcg gtaggcgtgt acggtgggag    600

gtctatataa gcagagctgg tttagtgaac cgtcagatcc gctagcatgc ccctcaacgt    660

tagcttcacc aacaggaact atgacctcga ctacgactcg gtgcagccgt atttctactg    720

cgacgaggag gagaacttct accagcagca gcagcagagc gagctgcagc ccccggcgcc    780

cagcgaggat atctggaaga aattcgagct gctgcccacc ccgcccctgt cccctagccg    840

ccgctccggg ctctgctcgc cctcctacgt tgcggtcaca cccttctccc ttcggggaga    900

caacgacggc ggtggcggga gcttctccac ggccgaccag ctggagatgg tgaccgagct    960

gctgggagga gacatggtga accagagttt catctgcgac ccggacgacg agaccttcat   1020

caaaaacatc atcatccagg actgtatgtg gagcggcttc tcggccgccg ccaagctcgt   1080

ctcagagaag ctggcctcct accaggctgc gcgcaaagac agcggcagcc cgaaccccgc   1140

ccgcggccac agcgtctgct ccacctccag cttgtacctg caggatctga gcgccgccgc   1200

ctcagagtgc atcgacccct cggtggtctt cccctaccct ctcaacgaca gcagctcgcc   1260

caagtcctgc gcctcgcaag actccagcgc cttctctccg tcctcggatt ctctgctctc   1320

ctcgacggag tcctccccgc agggcagccc cgagcccctg gtgctccatg aggagacacc   1380

gcccaccacc agcagcgact ctgaggagga acaagaagat gaggaagaaa tcgatgttgt   1440

ttctgtggaa aagaggcagg ctcctggcaa aaggtcagag tctggatcac cttctgctgg   1500

aggccacagc aaacctcctc acagcccact ggtcctcaag aggtgccacg tctccacaca   1560

tcagcacaac tacgcagcgc ctccctccac tcggaaggac tatcctgctg ccaagagggt   1620

caagttggac agtgtcagag tcctgagaca gatcagcaac aaccgaaaat gcaccagccc   1680

caggtcctcg gacaccgagg agaatgtcaa gaggcgaaca cacaacgtct tggagcgcca   1740
```

-continued

```
gaggaggaac gagctaaaac ggagcttttt tgccctgcgt gaccagatcc cggagttgga   1800
aaacaatgaa aaggccccca aggtagttat ccttaaaaaa gccacagcat acatcctgtc   1860
cgtccaagca gaggagcaaa agctcatttc tgaagaggac ttgttgcgga aacgacgaga   1920
acagttgaaa cacaaacttg aacagctacg gaactcttgt gcgtaagcta gcgctaccgg   1980
actcagatcg gccgcgactc tagatcataa tcagccatac cacatttgta gaggttttac   2040
ttgctttaaa aaacctccca cacctccccc tgaacctgaa acataaaatg aatgcaattg   2100
ttgttgttaa cttgtttatt gcagcttata atggttacaa ataaagcaat agcatcacaa   2160
atttcacaaa taaagcattt ttttcactgc attctagttg tggtttgtcc aaactcatca   2220
atgtattcta gagataattc agtaatcaat tacggggtca ttagttcata gcccatatat   2280
ggagttccgc gttacataac ttacggtaaa tggcccgcct ggctgaccgc ccaacgaccc   2340
ccgcccattg acgtcaatgg gagtttgttt tggcaccaaa atcaacggga ctttccaaaa   2400
tgtcgtaaca actccgcccc attgacgcaa atgggcggta ggcgtgtacg gtgggaggtc   2460
tatataagca gagctggttt agtgaaccgt cagatccgct agcatggctg tcagcgacgc   2520
gctgctccca tctttctcca cgttcgcgtc tggcccggcg ggaagggaga agacactgcg   2580
tcaagcaggt gccccgaata accgctggcg ggaggagctc tcccacatga agcgacttcc   2640
cccagtgctt cccggccgcc cctatgacct ggcggcggcg accgtggcca cagacctgga   2700
gagcggcgga gccggtgcgg cttgcggcgg tagcaacctg gcgcccctac ctcggagaga   2760
gaccgaggag ttcaacgatc tcctggacct ggactttatt ctctccaatt cgctgaccca   2820
tcctccggag tcagtggccg ccaccgtgtc ctcgtcagcg tcagcctcct cttcgtcgtc   2880
gccgtcgagc agcggccctg ccagcgcgcc ctccacctgc agcttcacct atccgatccg   2940
ggccgggaac gacccgggcg tggcgccggg cggcacgggc ggaggcctcc tctatggcag   3000
ggagtccgct ccccctccga cggctccctt caacctggcg gacatcaacg acgtgagccc   3060
ctcgggcggc ttcatggccg agctcctgcg gccagaattg gacccggtgt acattccgcc   3120
gcagcagccg cagccgccag gtggcgggct gatgggcaag ttcgtgctga aggcgtcgct   3180
gagcgcccct ggcagcgagt acggcagccc gtcggtcatc agcgtcagca aaggcagccc   3240
tgacggcagc cacccggtgg tggtggcgcc ctacaacggc gggccgccgc gcacgtgccc   3300
caagatcaag caggaggcgg tctcttcgtg cacccacttg ggcgctggac cccctctcag   3360
caatggccac cggccggctg cacacgactt cccccctgggg cggcagctcc ccagcaggac   3420
taccccgacc ctgggtcttg aggaagtgct gagcagcagg gactgtcacc ctgccctgcc   3480
gcttcctccc ggcttccatc cccacccggg gcccaattac ccatccttcc tgcccgatca   3540
gatgcagccg caagtcccgc cgctccatta ccaagagctc atgccacccg gttcctgcat   3600
gccagaggag cccaagccaa agaggggaag acgatcgtgg ccccggaaaa ggaccgccac   3660
ccacacttgt gattacgcgg gctgcggcaa aacctacaca aagagttccc atctcaaggc   3720
acacctgcga acccacacag gtgagaaacc ttaccactgt gactgggacg gctgtggatg   3780
gaaattcgcc cgctcagatg aactgaccag gcactaccgt aaacacacgg ggcaccgccc   3840
gttccagtgc caaaaatgcg accgagcatt ttccaggtcg gaccacctcg ccttacacat   3900
gaagaggcat ttttaagcta gcgctaccgg actcagatcg gccgcgactc tagatcataa   3960
tcagccatac cacatttgta gaggttttac ttgctttaaa aaacctccca cacctccccc   4020
tgaacctgaa acataaaatg aatgcaattg ttgttgttaa cttgtttatt gcagcttata   4080
```

```
atggttacaa ataaagcaat agcatcacaa atttcacaaa taaagcattt ttttcactgc   4140
attctagttg tggtttgtcc aaactcatca atgtatgaat tatcgaattc aagcttagta   4200
atcaattacg gggtcattag ttcatagccc atatatggag ttccgcgtta cataacttac   4260
ggtaaatggc ccgcctggct gaccgcccaa cgacccccgc ccattgacgt caatgggagt   4320
ttgttttggc accaaaatca acgggacttt ccaaaatgtc gtaacaactc cgccccattg   4380
acgcaaatgg gcggtaggcg tgtacggtgg gaggtctata taagcagagc tggtttagtg   4440
aaccgtcaga tccgctagca tgtacaacat gatggagacg gagctgaagc cgccgggccc   4500
gcagcaaact tcggggggcg gcggcggcaa ctccaccgcg gcggcggccg gcggcaacca   4560
gaaaaacagc ccggaccgcg tcaagcggcc catgaatgcc ttcatggtgt ggtcccgcgg   4620
gcagcggcgc aagatggccc aggagaaccc caagatgcac aactcggaga tcagcaagcg   4680
cctgggcgcc gagtggaaac ttttgtcgga gacggagaag cggccgttca tcgacgaggc   4740
taagcggctg cgagcgctgc acatgaagga gcacccggat tataaatacc ggccccggcg   4800
gaaaaccaag acgctcatga agaaggataa gtacacgctg cccggcgggc tgctggcccc   4860
cggcggcaat agcatggcga gcggggtcgg ggtgggcgcc ggcctgggcg cgggcgtgaa   4920
ccagcgcatg gacagttacg cgcacatgaa cggctggagc aacggcagct acagcatgat   4980
gcaggaccag ctgggctacc cgcagcaccc gggcctcaat gcgcacggcg cagcgcagat   5040
gcagcccatg caccgctacg acgtgagcgc cctgcagtac aactccatga ccagctcgca   5100
gacctacatg aacggctcgc ccacctacag catgtcctac tcgcagcagg gcacccctgg   5160
catggctctt ggctccatgg gttcggtggt caagtccgag gccagctcca gcccccctgt   5220
ggttacctct tcctcccact ccagggcgcc ctgccaggcc ggggacctcc gggacatgat   5280
cagcatgtat ctccccggcg ccgaggtgcc ggaacccgcc gcccccagca gacttcacat   5340
gtcccagcac taccagagcg gcccggtgcc cggcacggcc attaacggca cactgcccct   5400
ctcacacatg tgagctagcg ctaccggact cagatcggcc gcgactctag atcataatca   5460
gccataccac atttgtagag gttttacttg ctttaaaaaa cctcccacac ctccccctga   5520
acctgaaaca taaaatgaat gcaattgttg ttgttaactt gtttattgca gcttataatg   5580
gttacaaata aagcaatagc atcacaaatt tcacaaataa agcatttttt tcactgcatt   5640
ctagttgtgg tttgtccaaa ctcatcaatg tataagcttg tcgacagtaa tcaattacgg   5700
ggtcattagt tcatagccca tatatggagt tccgcgttac ataacttacg gtaaatggcc   5760
cgcctggctg accgcccaac gacccccgcc cattgacgtc aatgggagtt tgttttggca   5820
ccaaaatcaa cgggactttc caaaatgtcg taacaactcc gccccattga cgcaaatggg   5880
cggtaggcgt gtacggtggg aggtctatat aagcagagct ggtttagtga accgtcagat   5940
ccgctagcat ggcgggacac ctggcttcgg atttcgcctt ctcgcccccct ccaggtggtg   6000
gaggtgatgg gccagggggg ccggagccgg gctgggttga tcctcggacc tggctaagct   6060
tccaaggccc tcctggaggg ccaggaatcg ggccgggggt tgggccaggc tctgaggtgt   6120
gggggattcc cccatgcccc ccgccgtatg agttctgtgg ggggatggcg tactgtgggc   6180
cccaggttgg agtggggcta gtgccccaag gcggcttgga gacctctcag cctgagggtg   6240
aagcangagt cggggtggag agcaactccg atggggcctc ccccggagccc tgcaccgtca   6300
cccctggtgc cgtgaagctg gagaaggaga agctggagca aaacccggag gagtcccagg   6360
acatcaaagc tctgcagaaa gaactcgagc aatttgccaa gctcctgaag cagaagagga   6420
tcaccctggg atatacacag gccgatgtgg ggctcaccct gggggttcta tttgggaagg   6480
```

```
tattcagcca aacgaccatc tgccgctttg aggctctgca gcttagcttc aagaacatgt   6540
gtaagctgcg gcccttgctg cagaagtggg tggaggaagc tgacaacaat gaaaatcttc   6600
aggagatatg caaagcagaa accctcgtgc aggcccgaaa gagaaagcga accagtatcg   6660
agaaccgagt gagaggcaac ctggagaatt tgttcctgca gtgcccgaaa cccacactgc   6720
agcagatcag ccacatcgcc cagcagcttg ggctcgagaa ggatgtggtc cgagtgtggt   6780
tctgtaaccg gcgccagaag ggcaagcgat caagcagcga ctatgcacaa cgagaggatt   6840
ttgaggctgc tgggtctcct ttctcagggg gaccagtgtc ctttcctctg gccccagggc   6900
cccatttggg taccccaggc tatgggagcc ctcacttcac tgcactgtac tcctcggtcc   6960
ctttccctga gggggaagcc tttccccctg tctccgtcac cactctgggc tctcccatgc   7020
attcaaactg agctagcgct accggactca gatcggccgc gactctagat cataatcagc   7080
cataccacat ttgtagaggt tttacttgct ttaaaaaacc tcccacacct ccccctgaac   7140
ctgaaacata aaatgaatgc aattgttgtt gttaacttgt ttattgcagc ttataatggt   7200
tacaaataaa gcaatagcat cacaaatttc acaaataaag catttttttc actgcattct   7260
agttgtggtt tgtccaaact catcaatgta tgtcgacaga tctnnntaag ggtgggaaag   7320
aatatataag gtgggggtct tatgtagttt tgtatctgtt ttgcagcagc cgccgccgcc   7380
atgagcacca actcgtttga tggaagcatt gtgagctcat atttgacaac gcgcatgccc   7440
ccatgggccg gggtgcgtca gaatgtgatg ggctccagca ttgatggtcg ccccgtcctg   7500
cccgcaaact ctactacctt gacctacgag accgtgtctg gaacgccgtt ggagactgca   7560
gcctccgccg ccgcttcagc cgctgcagcc accgcccgcg ggattgtgac tgactttgct   7620
ttcctgagcc cgcttgcaag cagtgcagct tcccgttcat ccgcccgcga tgacaagttg   7680
acggctcttt tggcacaatt ggattctttg acccgggaac ttaatgtcgt ttctcagcag   7740
ctgttggatc tgcgccagca ggtttctgcc ctgaaggctt cctcccctcc caatgcggtt   7800
taaaacataa ataaaaaacc agactctgtt tggatttgga tcaagcaagt gtcttgctgt   7860
ctttatttag gggttttgcg cgcgcggtag gcccgggacc agcggtctcg gtcgttgagg   7920
gtcctgtgta tttttccag gacgtggtaa aggtgactct ggatgttcag atacatgggc   7980
ataagcccgt ctctggggtg gaggtagcac cactgcagag cttcatgctg cggggtggtg   8040
ttgtagatga tccagtcgta gcaggagcgc tgggcgtggt gcctaaaaat gtctttcagt   8100
agcaagctga ttgccagggg caggcccttg gtgtaagtgt ttacaaagcg gttaagctgg   8160
gatgggtgca tacgtgggga tatgagatgc atcttggact gtatttttag gttggctatg   8220
ttcccagcca tatccctccg ggattcatg ttgtgcagaa ccaccagcac agtgtatccg   8280
gtgcacttgg gaaatttgtc atgtagctta gaaggaaatg cgtggaagaa cttggagacg   8340
cccttgtgac ctccaagatt ttccatgcat tcgtccataa tgatggcaat gggcccacgg   8400
gcggcggcct gggcgaagat atttctggga tcactaacgt catagttgtg ttccaggatg   8460
agatcgtcat aggccatttt tacaaagcgc gggcggaggg tgccagactg cggtataatg   8520
gttccatccg gcccaggggc gtagttaccc tcacagattt gcatttccca cgctttgagt   8580
tcagatgggg ggatcatgtc tacctgcggg gcgatgaaga aaacggtttc cggggtaggg   8640
gagatcagct gggaagaaag caggttcctg agcagctgcg acttaccgca gccggtgggc   8700
ccgtaaatca cacctattac cgggtgcaac tggtagttaa gagagctgca gctgccgtca   8760
tccctgagca ggggggccac ttcgttaagc atgtccctga ctcgcatgtt ttccctgacc   8820
```

```
aaatccgcca gaaggcgctc gccgcccagc gatagcagtt cttgcaagga agcaaagttt   8880
ttcaacggtt tgagaccgtc cgccgtaggc atgcttttga gcgtttgacc aagcagttcc   8940
aggcggtccc acagctcggt cacctgctct acggcatctc gatccagcat atctcctcgt   9000
ttcgcgggtt ggggcggctt tcgctgtacg gcagtagtcg gtgctcgtcc agacgggcca   9060
gggtcatgtc tttccacggg cgcagggtcc tcgtcagcgt agtctgggtc acggtgaagg   9120
ggtgcgctcc gggctgcgcg ctggccaggg tgcgcttgag gctggtcctg ctggtgctga   9180
agcgctgccg gtcttcgccc tgcgcgtcgg ccaggtagca tttgaccatg gtgtcatagt   9240
ccagcccctc cgcggcgtgg cccttggcgc gcagcttgcc cttggaggag gcgccgcacg   9300
aggggcagtg cagacttttg agggcgtaga gcttgggcgc gagaaatacc gattccgggg   9360
agtaggcatc cgcgccgcag gccccgcaga cggtctcgca ttccacgagc caggtgagct   9420
ctggccgttc ggggtcaaaa accaggtttc ccccatgctt tttgatgcgt ttcttacctc   9480
tggtttccat gagccggtgt ccacgctcgg tgacgaaaag gctgtccgtg tccccgtata   9540
cagactnnng tttaaacgaa ttcnnntata aaatgcaagg tgctgctcaa aaaatcaggc   9600
aaagcctcgc gcaaaaaaga aagcacatcg tagtcatgct catgcagata aaggcaggta   9660
agctccggaa ccaccacaga aaaagacacc atttttctct caaacatgtc tgcgggtttc   9720
tgcataaaca caaaataaaa taacaaaaaa acatttaaac attagaagcc tgtcttacaa   9780
caggaaaaac aacccttata agcataagac ggactacggc catgccggcg tgaccgtaaa   9840
aaaactggtc accgtgatta aaaagcacca ccgacagctc ctcggtcatg tccggagtca   9900
taatgtaaga ctcggtaaac acatcaggtt gattcatcgg tcagtgctaa aaagcgaccg   9960
aaatagcccg gggggaatac atacccgcagg cgtagagaca acattacagc cccatagga  10020
ggtataacaa aattaatagg agagaaaaac acataaacac ctgaaaaacc ctcctgccta  10080
ggcaaaatag caccctcccg ctccagaaca acatacagcg cttcacagcg gcagcctaac  10140
agtcagcctt accagtaaaa aagaaaacct attaaaaaaa caccactcga cacggcacca  10200
gctcaatcag tcacagtgta aaaaagggcc aagtgcagag cgagtatata taggactaaa  10260
aaatgacgta acggttaaag tccacaaaaa acacccagaa aaccgcacgc gaacctacgc  10320
ccagaaacga aagccaaaaa acccacaact tcctcaaatc gtcacttccg ttttcccacg  10380
ttacgtaact tcccatttta agaaaactac aattcccaac acatacaagt tactccgccc  10440
taaaacctac gtcacccgcc ccgttcccac gccccgcgcc acgtcacaaa ctccaccccc  10500
tcattatcat attggcttca atccaaaata aggtatatta ttgatgatnn nttaattaag  10560
gatccnnncg gtgtgaaata ccgcacagat gcgtaaggag aaaataccgc atcaggcgct  10620
cttccgcttc ctcgctcact gactcgctgc gctcggtcgt tcggctgcgg cgagcggtat  10680
cagctcactc aaaggcggta atacggttat ccacagaatc aggggataac gcaggaaaga  10740
acatgtgagc aaaaggccag caaaaggcca ggaaccgtaa aaaggccgcg ttgctggcgt  10800
ttttccatag gctccgcccc cctgacgagc atcacaaaaa tcgacgctca agtcagaggt  10860
ggcgaaaccc gacaggacta taaagatacc aggcgtttcc ccctggaagc tccctcgtgc  10920
gctctcctgt tccgaccctg ccgcttaccg gatacctgtc cgcctttctc ccttcgggaa  10980
gcgtggcgct ttctcatagc tcacgctgta ggtatctcag ttcggtgtag gtcgttcgct  11040
ccaagctggg ctgtgtgcac gaaccccccg ttcagcccga ccgctgcgcc ttatccggta  11100
actatcgtct tgagtccaac ccggtaagac acgacttatc gccactggca gcagccactg  11160
gtaacaggat tagcagagcg aggtatgtag gcggtgctac agagttcttg aagtggtggc  11220
```

```
ctaactacgg ctacactaga aggacagtat ttggtatctg cgctctgctg aagccagtta  11280

ccttcggaaa aagagttggt agctcttgat ccggcaaaca aaccaccgct ggtagcggtg  11340

gtttttttgt ttgcaagcag cagattacgc gcagaaaaaa aggatctcaa gaagatcctt  11400

tgatcttttc tacggggtct gacgctcagt ggaacgaaaa ctcacgttaa gggattttgg  11460

tcatgagatt atcaaaaagg atcttcacct agatcctttt aaattaaaaa tgaagtttta  11520

aatcaatcta aagtatatat gagtaaactt ggtctgacag ttaccaatgc ttaatcagtg  11580

aggcacctat ctcagcgatc tgtctatttc gttcatccat agttgcctga ctccccgtcg  11640

tgtagataac tacgatacgg gagggcttac catctggccc cagtgctgca atgataccgc  11700

gagacccacg ctcaccggct ccagatttat cagcaataaa ccagccagcc ggaagggccg  11760

agcgcagaag tggtcctgca actttatccg cctccatcca gtctattaat tgttgccggg  11820

aagctagagt aagtagttcg ccagttaata gtttgcgcaa cgttgttgnn nnnnaaaaag  11880

gatcttcacc tagatccttt tcacgtagaa agccagtccg cagaaacggt gctgaccccg  11940

gatgaatgtc agctactggg ctatctggac aagggaaaac gcaagcgcaa agagaaagca  12000

ggtagcttgc agtgggctta catggcgata gctagactgg gcggttttat ggacagcaag  12060

cgaaccggaa ttgccagctg gggcgccctc tggtaaggtt gggaagccct gcaaagtaaa  12120

ctggatggct ttctcgccgc caaggatctg atggcgcagg ggatcaagct ctgatcaaga  12180

gacaggatga ggatcgtttc gcatgattga acaagatgga ttgcacgcag gttctccggc  12240

cgcttgggtg gagaggctat tcggctatga ctgggcacaa cagacaatcg gctgctctga  12300

tgccgccgtg ttccggctgt cagcgcaggg gcgcccggtt ctttttgtca agaccgacct  12360

gtccggtgcc ctgaatgaac tgcaagacga ggcagcgcgg ctatcgtggc tggccacgac  12420

gggcgttcct tgcgcagctg tgctcgacgt tgtcactgaa gcgggaaggg actggctgct  12480

attgggcgaa gtgccggggc aggatctcct gtcatctcac cttgctcctg ccgagaaagt  12540

atccatcatg gctgatgcaa tgcggcggct gcatacgctt gatccggcta cctgcccatt  12600

cgaccaccaa gcgaaacatc gcatcgagcg agcacgtact cggatggaag ccggtcttgt  12660

cgatcaggat gatctggacg aagagcatca ggggctcgcg ccagccgaac tgttcgccag  12720

gctcaaggcg agcatgcccg acggcgagga tctcgtcgtg acccatggcg atgcctgctt  12780

gccgaatatc atggtggaaa atggccgctt ttctggattc atcgactgtg gccggctggg  12840

tgtggcggac cgctatcagg acatagcgtt ggctacccgt gatattgctg aagagcttgg  12900

cggcgaatgg gctgaccgct tcctcgtgct ttacggtatc gccgctcccg attcgcagcg  12960

catcgccttc tatcgccttc ttgacgagtt cttctgaatt ttgttaaaat tttgttaaa   13020

tcagctcatt ttttaaccaa taggccgaaa tcggcaacat cccttataaa tcaaaagaat  13080

agaccgcgat agggttgagt gttgttccag tttggaacaa gagtccacta ttaaagaacg  13140

tggactccaa cgtcaaaggg cgaaaaaccg tctatcaggg cgatggccca ctacgtgaac  13200

catcacccaa atcaagtttt ttgcggtcga ggtgccgtaa agctctaaat cggaacccta  13260

aagggagccc ccgatttaga gcttgacggg gaaagccggc gaacgtggcg agaaaggaag  13320

ggaagaaagc gaaaggagcg ggcgctaggg cgctggcaag tgtagcggtc acgctgcgcg  13380

taaccaccac acccgcgcgc ttaatgcgcc gnnnnnnn                          13418
```

<210> SEQ ID NO 4
<211> LENGTH: 12887
<212> TYPE: DNA

<213> ORGANISM: Artificial Sequence
<220> FEATURE:
<223> OTHER INFORMATION: The adeno shuttle vector containing multi-RFs under CMV weak promoter (CMVWP) has been provided as pAd(CMVWP)-GFP-KSO (K; KLF4, S; SOX2, O; OCT3/4).
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (5715)..(5715)
<223> OTHER INFORMATION: n is a, c, g, or t
<220> FEATURE:
<221> NAME/KEY: misc_feature
<222> LOCATION: (6773)..(6775)
<223> OTHER INFORMATION: n is a, c, g, or t
<220> FEATURE:
<221> NAME/KEY: misc_feature
<222> LOCATION: (9016)..(9018)
<223> OTHER INFORMATION: n is a, c, g, or t
<220> FEATURE:
<221> NAME/KEY: misc_feature
<222> LOCATION: (9033)..(9035)
<223> OTHER INFORMATION: n is a, c, g, or t
<220> FEATURE:
<221> NAME/KEY: misc_feature
<222> LOCATION: (10018)..(10020)
<223> OTHER INFORMATION: n is a, c, g, or t
<220> FEATURE:
<221> NAME/KEY: misc_feature
<222> LOCATION: (10035)..(10037)
<223> OTHER INFORMATION: n is a, c, g, or t
<220> FEATURE:
<221> NAME/KEY: misc_feature
<222> LOCATION: (11338)..(11343)
<223> OTHER INFORMATION: n is a, c, g, or t
<220> FEATURE:
<221> NAME/KEY: misc_feature
<222> LOCATION: (12881)..(12887)
<223> OTHER INFORMATION: n is a, c, g, or t

<400> SEQUENCE: 4

```
nnnttaatta annntccctt ccagctctct gccccttttg gattgaagcc aatatgataa      60

tgaggggggtg gagtttgtga cgtggcgcgg ggcgtgggaa cggggcgggt gacgtagtag    120

tgtggcggaa gtgtgatgtt gcaagtgtgg cggaacacat gtaagcgacg gatgtggcaa    180

aagtgacgtt tttggtgtgc gccggtgtac acaggaagtg acaattttcg cgcggtttta    240

ggcggatgtt gtagtaaatt tgggcgtaac cgagtaagat ttggccattt tcgcgggaaa    300

actgaataag aggaagtgaa atctgaataa ttttgtgtta ctcatagcgc gtaannnggt    360

accgcggcct aatagtaatc aattacgggg tcattagttc atagcccata tatggagttc    420

cgcgttacat aacttacggt aaatggcccg cctggctgac cgcccaacga cccccgccca    480

ttgacgtcaa tgggagtttg ttttggcacc aaaatcaacg ggactttcca aaatgtcgta    540

acaactccgc cccattgacg caaatgggcg gtaggcgtgt acggtgggag gtctatataa    600

gcagagctgg tttagtgaac cgtcagatcc gctagcgcta ccggactcag atctcgagct    660

caagcttcga attctgcagt cgacggtacc gcgggcccgg gatccaccgg tcgccaccat    720

ggtgagcaag ggcgaggagc tgttcaccgg ggtggtgccc atcctggtcg agctggacgg    780

cgacgtaaac ggccacaagt tcagcgtgtc cggcgagggc gagggcgatg ccacctacgg    840
```

```
caagctgacc ctgaagttca tctgcaccac cggcaagctg cccgtgccct ggcccaccct    900
cgtgaccacc ctgacctacg gcgtgcagtg cttcagccgc taccccgacc acatgaagca    960
gcacgacttc ttcaagtccg ccatgcccga aggctacgtc caggagcgca ccatcttctt   1020
caaggacgac ggcaactaca agacccgcgc cgaggtgaag ttcgagggcg acaccctggt   1080
gaaccgcatc gagctgaagg gcatcgactt caaggaggac ggcaacatcc tggggcacaa   1140
gctggagtac aactacaaca gccacaacgt ctatatcatg gccgacaagc agaagaacgg   1200
catcaaggtg aacttcaaga tccgccacaa catcgaggac ggcagcgtgc agctcgccga   1260
ccactaccag cagaacaccc ccatcggcga cggccccgtg ctgctgcccg acaaccacta   1320
cctgagcacc cagtccgccc tgagcaaaga ccccaacgag aagcgcgatc acatggtcct   1380
gctggagttc gtgaccgccg ccgggatcac tctcggcatg gacgagctgt acaagtaaag   1440
cggccgcgac tctagatcat aatcagccat accacatttg tagaggtttt acttgcttta   1500
aaaaacctcc cacacctccc cctgaacctg aaacataaaa tgaatgcaat tgttgttgtt   1560
aacttgttta ttgcagctta taatggttac aaataaagca atagcatcac aaatttcaca   1620
aataaagcat ttttttcact gcattctagt tgtggtttgt ccaaactcat caatgtatct   1680
taaggccgcc tcgagtctag agataattca gtaatcaatt acggggtcat tagttcatag   1740
cccatatatg gagttccgcg ttacataact tacggtaaat ggcccgcctg gctgaccgcc   1800
caacgacccc cgcccattga cgtcaatggg agtttgtttt ggcaccaaaa tcaacgggac   1860
tttccaaaat gtcgtaacaa ctccgcccca ttgacgcaaa tgggcggtag gcgtgtacgg   1920
tgggaggtct atataagcag agctggttta gtgaaccgtc agatccgcta gcatggctgt   1980
cagcgacgcg ctgctcccat ctttctccac gttcgcgtct ggcccggcgg gaagggagaa   2040
gacactgcgt caagcaggtg ccccgaataa ccgctggcgg gaggagctct cccacatgaa   2100
gcgacttccc ccagtgcttc ccggccgccc ctatgacctg gcggcggcga ccgtggccac   2160
agacctggag agcggcggag ccggtgcggc ttgcggcggt agcaacctgg cgcccctacc   2220
tcggagagag accgaggagt tcaacgatct cctggacctg gactttattc tctccaattc   2280
gctgacccat cctccggagt cagtggccgc caccgtgtcc tcgtcagcgt cagcctcctc   2340
ttcgtcgtcg ccgtcgagca gcggccctgc cagcgcgccc tccacctgca gcttcaccta   2400
tccgatccgg gccgggaacg acccgggcgt ggcgccgggc ggcacgggcg gaggcctcct   2460
ctatggcagg gagtccgctc cccctccgac ggctcccttc aacctggcgg acatcaacga   2520
cgtgagcccc tcgggcggct tcatggccga gctcctgcgg ccagaattgg acccggtgta   2580
cattccgccg cagcagccgc agccgccagg tggcgggctg atgggcaagt tcgtgctgaa   2640
ggcgtcgctg agcgcccctg gcagcgagta cggcagcccg tcggtcatca gcgtcagcaa   2700
aggcagccct gacggcagcc acccggtggt ggtggcgccc tacaacggcg ggccgccgcg   2760
cacgtgcccc aagatcaagc aggaggcggt ctcttcgtgc acccacttgg gcgctggacc   2820
ccctctcagc aatggccacc ggccggctgc acacgacttc cccctggggc ggcagctccc   2880
cagcaggact accccgaccc tgggtcttga ggaagtgctg agcagcaggg actgtcaccc   2940
tgccctgccg cttcctcccg gcttccatcc ccacccgggg cccaattacc catccttcct   3000
gcccgatcag atgcagccgc aagtcccgcc gctccattac caagagctca tgccacccgg   3060
ttcctgcatg ccagaggagc ccaagccaaa gaggggaaga cgatcgtggc cccggaaaag   3120
gaccgccacc cacacttgtg attacgcggg ctgcggcaaa acctacacaa agagttccca   3180
```

-continued

```
tctcaaggca cacctgcgaa cccacacagg tgagaaacct taccactgtg actgggacgg   3240
ctgtggatgg aaattcgccc gctcagatga actgaccagg cactaccgta aacacacggg   3300
gcaccgcccg ttccagtgcc aaaaatgcga ccgagcattt tccaggtcgg accacctcgc   3360
cttacacatg aagaggcatt tttaagctag cgctaccgga ctcagatcgg ccgcgactct   3420
agatcataat cagccatacc acatttgtag aggttttact tgctttaaaa aacctcccac   3480
acctccccct gaacctgaaa cataaaatga atgcaattgt tgttgttaac ttgtttattg   3540
cagcttataa tggttacaaa taaagcaata gcatcacaaa tttcacaaat aaagcatttt   3600
tttcactgca ttctagttgt ggtttgtcca aactcatcaa tgtatgaatt atcgaattca   3660
agcttagtaa tcaattacgg ggtcattagt tcatagccca tatatggagt tccgcgttac   3720
ataacttacg gtaaatggcc cgcctggctg accgcccaac gacccccgcc cattgacgtc   3780
aatgggagtt tgttttggca ccaaaatcaa cgggactttc caaaatgtcg taacaactcc   3840
gccccattga cgcaaatggg cggtaggcgt gtacggtggg aggtctatat aagcagagct   3900
ggtttagtga accgtcagat ccgctagcat gtacaacatg atggagacgg agctgaagcc   3960
gccgggcccg cagcaaactt cggggggcgg cggcggcaac tccaccgcgg cggcggccgg   4020
cggcaaccag aaaaacagcc cggaccgcgt caagcggccc atgaatgcct tcatggtgtg   4080
gtcccgcggg cagcggcgca agatggccca ggagaacccc aagatgcaca actcggagat   4140
cagcaagcgc ctgggcgccg agtggaaact tttgtcggag acggagaagc ggccgttcat   4200
cgacgaggct aagcggctgc gagcgctgca catgaaggag cacccggatt ataaataccg   4260
gccccggcgg aaaaccaaga cgctcatgaa gaaggataag tacacgctgc ccggcgggct   4320
gctggccccc ggcggcaata gcatggcgag cggggtcggg gtgggcgccg gcctgggcgc   4380
gggcgtgaac cagcgcatgg acagttacgc gcacatgaac ggctggagca acggcagcta   4440
cagcatgatg caggaccagc tgggctaccc gcagcacccg ggcctcaatg cgcacggcgc   4500
agcgcagatg cagcccatgc accgctacga cgtgagcgcc ctgcagtaca actccatgac   4560
cagctcgcag acctacatga acggctcgcc cacctacagc atgtcctact cgcagcaggg   4620
cacccctggc atggctcttg gctccatggg ttcggtggtc aagtccgagg ccagctccag   4680
cccccctgtg gttacctctt cctcccactc cagggcgccc tgccaggccg gggacctccg   4740
ggacatgatc agcatgtatc tccccggcgc cgaggtgccg gaacccgccg cccccagcag   4800
acttcacatg tcccagcact accagagcgg cccggtgccc ggcacggcca ttaacggcac   4860
actgcccctc tcacacatgt gagctagcgc taccggactc agatcggccg cgactctaga   4920
tcataatcag ccataccaca tttgtagagg ttttacttgc tttaaaaaac ctcccacacc   4980
tccccctgaa cctgaaacat aaaatgaatg caattgttgt tgttaacttg tttattgcag   5040
cttataatgg ttacaaataa agcaatagca tcacaaattt cacaaataaa gcattttttt   5100
cactgcattc tagttgtggt ttgtccaaac tcatcaatgt ataagcttgt cgacagtaat   5160
caattacggg gtcattagtt catagcccat atatggagtt ccgcgttaca taacttacgg   5220
taaatggccc gcctggctga ccgcccaacg acccccgccc attgacgtca atgggagttt   5280
gttttggcac caaaatcaac gggactttcc aaaatgtcgt aacaactccg ccccattgac   5340
gcaaatgggc ggtaggcgtg tacggtggga ggtctatata agcagagctg gtttagtgaa   5400
ccgtcagatc cgctagcatg gcgggacacc tggcttcgga tttcgccttc tcgccccctc   5460
caggtggtgg aggtgatggg ccagggggc cggagccggg ctgggttgat cctcggacct   5520
ggctaagctt ccaaggccct cctggagggc caggaatcgg gccgggggtt gggccaggct   5580
```

```
ctgaggtgtg ggggattccc ccatgccccc cgccgtatga gttctgtggg gggatggcgt   5640
actgtgggcc ccaggttgga gtggggctag tgccccaagg cggcttggag acctctcagc   5700
ctgagggtga agcangagtc ggggtggaga gcaactccga tggggcctcc ccggagccct   5760
gcaccgtcac ccctggtgcc gtgaagctgg agaaggagaa gctggagcaa aacccggagg   5820
agtcccagga catcaaagct ctgcagaaag aactcgagca atttgccaag ctcctgaagc   5880
agaagaggat caccctggga tatacacagg ccgatgtggg gctcaccctg gggttctat    5940
ttgggaaggt attcagccaa acgaccatct gccgctttga ggctctgcag cttagcttca   6000
agaacatgtg taagctgcgg cccttgctgc agaagtgggt ggaggaagct gacaacaatg   6060
aaaatcttca ggagatatgc aaagcagaaa ccctcgtgca ggcccgaaag agaaagcgaa   6120
ccagtatcga gaaccgagtg agaggcaacc tggagaattt gttcctgcag tgcccgaaac   6180
ccacactgca gcagatcagc cacatcgccc agcagcttgg gctcgagaag gatgtggtcc   6240
gagtgtggtt ctgtaaccgg cgccagaagg gcaagcgatc aagcagcgac tatgcacaac   6300
gagaggattt tgaggctgct gggtctcctt tctcaggggg accagtgtcc tttcctctgg   6360
ccccagggcc ccattttggt accccaggct atggagccc tcacttcact gcactgtact    6420
cctcggtccc tttccctgag ggggaagcct ttcccccctgt ctccgtcacc actctgggct  6480
ctcccatgca ttcaaactga gctagcgcta ccggactcag atcggccgcg actctagatc   6540
ataatcagcc ataccacatt tgtagaggtt ttacttgctt taaaaaacct cccacacctc   6600
cccctgaacc tgaaacataa aatgaatgca attgttgttg ttaacttgtt tattgcagct   6660
tataatggtt acaaataaag caatagcatc acaaatttca caaataaagc atttttttca   6720
ctgcattcta gttgtggttt gtccaaactc atcaatgtat gtcgacagat ctnnntaagg   6780
gtgggaaaga atatataagg tgggggtctt atgtagtttt gtatctgttt tgcagcagcc   6840
gccgccgcca tgagcaccaa ctcgtttgat ggaagcattg tgagctcata tttgacaacg   6900
cgcatgcccc catgggccgg ggtgcgtcag aatgtgatgg gctccagcat tgatggtcgc   6960
cccgtcctgc ccgcaaactc tactaccttg acctacgaga ccgtgtctgg aacgccgttg   7020
gagactgcag cctccgccgc cgcttcagcc gctgcagcca ccgcccgcgg gattgtgact   7080
gactttgctt tcctgagccc gcttgcaagc agtgcagctt cccgttcatc cgcccgcgat   7140
gacaagttga cggctctttt ggcacaattg gattctttga cccgggaact taatgtcgtt   7200
tctcagcagc tgttggatct gcgccagcag gtttctgccc tgaaggcttc ctcccctccc   7260
aatgcggttt aaaacataaa taaaaaacca gactctgttt ggatttggat caagcaagtg   7320
tcttgctgtc tttatttagg ggttttgcgc gcgcggtagg cccgggacca gcggtctcgg   7380
tcgttgaggg tcctgtgtat tttttccagg acgtggtaaa ggtgactctg gatgttcaga   7440
tacatgggca taagcccgtc tctggggtgg aggtagcacc actgcagagc ttcatgctgc   7500
ggggtggtgt tgtagatgat ccagtcgtag caggagcgct gggcgtggtg cctaaaaatg   7560
tctttcagta gcaagctgat tgccaggggc aggcccttgg tgtaagtgtt tacaaagcgg   7620
ttaagctggg atgggtgcat acgtggggat atgagatgca tcttggactg tatttttagg   7680
ttggctatgt tcccagccat atccctccgg ggattcatgt tgtgcagaac caccagcaca   7740
gtgtatccgg tgcacttggg aaatttgtca tgtagcttag aaggaaatgc gtggaagaac   7800
ttggagacgc ccttgtgacc tccaagattt tccatgcatt cgtccataat gatggcaatg   7860
ggcccacggg cggcggcctg ggcgaagata tttctgggat cactaacgtc atagttgtgt   7920
```

```
tccaggatga gatcgtcata ggccattttt acaaagcgcg ggcggagggt gccagactgc   7980
ggtataatgg ttccatccgg cccaggggcg tagttaccct cacagatttg catttcccac   8040
gctttgagtt cagatggggg gatcatgtct acctgcgggg cgatgaagaa aacggtttcc   8100
ggggtagggg agatcagctg ggaagaaagc aggttcctga gcagctgcga cttaccgcag   8160
ccggtgggcc cgtaaatcac acctattacc gggtgcaact ggtagttaag agagctgcag   8220
ctgccgtcat ccctgagcag gggggccact tcgttaagca tgtccctgac tcgcatgttt   8280
tccctgacca aatccgccag aaggcgctcg ccgcccagcg atagcagttc ttgcaaggaa   8340
gcaaagtttt tcaacggttt gagaccgtcc gccgtaggca tgcttttgag cgtttgacca   8400
agcagttcca ggcggtccca cagctcggtc acctgctcta cggcatctcg atccagcata   8460
tctcctcgtt tcgcgggttg gggcggcttt cgctgtacgg cagtagtcgg tgctcgtcca   8520
gacgggccag ggtcatgtct ttccacgggc gcagggtcct cgtcagcgta gtctgggtca   8580
cggtgaaggg gtgcgctccg ggctgcgcgc tggccagggt gcgcttgagg ctggtcctgc   8640
tggtgctgaa gcgctgccgg tcttcgccct gcgcgtcggc caggtagcat ttgaccatgg   8700
tgtcatagtc cagcccctcc gcggcgtggc ccttggcgcg cagcttgccc ttggaggagg   8760
cgccgcacga ggggcagtgc agacttttga gggcgtagag cttgggcgcg agaaataccg   8820
attccgggga gtaggcatcc gcgccgcagg ccccgcagac ggtctcgcat tccacgagcc   8880
aggtgagctc tggccgttcg ggtcaaaaa ccaggtttcc cccatgcttt ttgatgcgtt   8940
tcttacctct ggtttccatg agccggtgtc cacgctcggt gacgaaaagg ctgtccgtgt   9000
ccccgtatac agactnnngt ttaaacgaat tcnnntataa aatgcaaggt gctgctcaaa   9060
aaatcaggca aagcctcgcg caaaaaagaa agcacatcgt agtcatgctc atgcagataa   9120
aggcaggtaa gctccggaac caccacagaa aaagacacca tttttctctc aaacatgtct   9180
gcgggtttct gcataaacac aaaataaaat aacaaaaaaa catttaaaca ttagaagcct   9240
gtcttacaac aggaaaaaca acccttataa gcataagacg gactacggcc atgccggcgt   9300
gaccgtaaaa aaactggtca ccgtgattaa aaagcaccac cgacagctcc tcggtcatgt   9360
ccggagtcat aatgtaagac tcggtaaaca catcaggttg attcatcggt cagtgctaaa   9420
aagcgaccga aatagcccgg gggaatacat acccgcaggc gtagagacaa cattacagcc   9480
cccataggag gtataacaaa attaatagga gagaaaaaca cataaacacc tgaaaaaccc   9540
tcctgcctag gcaaaatagc accctcccgc tccagaacaa catacagcgc ttcacagcgg   9600
cagcctaaca gtcagcctta ccagtaaaaa agaaaaccta ttaaaaaaac accactcgac   9660
acggcaccag ctcaatcagt cacagtgtaa aaaagggcca agtgcagagc gagtatatat   9720
aggactaaaa aatgacgtaa cggttaaagt ccacaaaaaa cacccagaaa accgcacgcg   9780
aacctacgcc cagaaacgaa agccaaaaaa cccacaactt cctcaaatcg tcacttccgt   9840
tttcccacgt tacgtaactt cccattttaa gaaaactaca attcccaaca catacaagtt   9900
actccgccct aaaacctacg tcacccgccc cgttcccacg ccccgcgcca cgtcacaaac   9960
tccacccccct cattatcata ttggcttcaa tccaaaataa ggtatattat tgatgatnnn  10020
ttaattaagg atccnnncgg tgtgaaatac cgcacagatg cgtaaggaga aaataccgca  10080
tcaggcgctc ttccgcttcc tcgctcactg actcgctgcg ctcggtcgtt cggctgcggc  10140
gagcggtatc agctcactca aaggcggtaa tacggttatc cacagaatca ggggataacg  10200
caggaaagaa catgtgagca aaaggccagc aaaaggccag gaaccgtaaa aaggccgcgt  10260
tgctggcgtt tttccatagg ctccgccccc ctgacgagca tcacaaaaat cgacgctcaa  10320
```

```
gtcagaggtg gcgaaacccg acaggactat aaagatacca ggcgtttccc cctggaagct  10380
ccctcgtgcg ctctcctgtt ccgaccctgc cgcttaccgg atacctgtcc gcctttctcc  10440
cttcgggaag cgtggcgctt tctcatagct cacgctgtag gtatctcagt tcggtgtagg  10500
tcgttcgctc caagctgggc tgtgtgcacg aaccccccgt tcagcccgac cgctgcgcct  10560
tatccggtaa ctatcgtctt gagtccaacc cggtaagaca cgacttatcg ccactggcag  10620
cagccactgg taacaggatt agcagagcga ggtatgtagg cggtgctaca gagttcttga  10680
agtggtggcc taactacggc tacactagaa ggacagtatt tggtatctgc gctctgctga  10740
agccagttac cttcggaaaa agagttggta gctcttgatc cggcaaacaa accaccgctg  10800
gtagcggtgg tttttttgtt tgcaagcagc agattacgcg cagaaaaaaa ggatctcaag  10860
aagatccttt gatcttttct acggggtctg acgctcagtg gaacgaaaac tcacgttaag  10920
ggattttggt catgagatta tcaaaaagga tcttcaccta gatcctttta aattaaaaat  10980
gaagttttaa atcaatctaa agtatatatg agtaaacttg gtctgacagt taccaatgct  11040
taatcagtga ggcacctatc tcagcgatct gtctatttcg ttcatccata gttgcctgac  11100
tccccgtcgt gtagataact acgatacggg agggcttacc atctggcccc agtgctgcaa  11160
tgataccgcg agacccacgc tcaccggctc cagatttatc agcaataaac cagccagccg  11220
gaagggccga gcgcagaagt ggtcctgcaa ctttatccgc ctccatccag tctattaatt  11280
gttgccggga agctagagta agtagttcgc cagttaatag tttgcgcaac gttgttgnnn  11340
nnnaaaaagg atcttcacct agatcctttt cacgtagaaa gccagtccgc agaaacggtg  11400
ctgaccccgg atgaatgtca gctactgggc tatctggaca agggaaaacg caagcgcaaa  11460
gagaaagcag gtagcttgca gtgggcttac atggcgatag ctagactggg cggttttatg  11520
gacagcaagc gaaccggaat tgccagctgg ggcgccctct ggtaaggttg ggaagccctg  11580
caaagtaaac tggatggctt tctcgccgcc aaggatctga tggcgcaggg gatcaagctc  11640
tgatcaagag acaggatgag gatcgtttcg catgattgaa caagatggat tgcacgcagg  11700
ttctccggcc gcttgggtgg agaggctatt cggctatgac tgggcacaac agacaatcgg  11760
ctgctctgat gccgccgtgt tccggctgtc agcgcagggg cgcccggttc tttttgtcaa  11820
gaccgacctg tccggtgccc tgaatgaact gcaagacgag gcagcgcggc tatcgtggct  11880
ggccacgacg ggcgttcctt gcgcagctgt gctcgacgtt gtcactgaag cgggaaggga  11940
ctggctgcta ttgggcgaag tgccggggca ggatctcctg tcatctcacc ttgctcctgc  12000
cgagaaagta tccatcatgg ctgatgcaat gcggcggctg catacgcttg atccggctac  12060
ctgcccattc gaccaccaag cgaaacatcg catcgagcga gcacgtactc ggatggaagc  12120
cggtcttgtc gatcaggatg atctggacga agagcatcag gggctcgcgc cagccgaact  12180
gttcgccagg ctcaaggcga gcatgcccga cggcgaggat ctcgtcgtga cccatggcga  12240
tgcctgcttg ccgaatatca tggtggaaaa tggccgcttt tctggattca tcgactgtgg  12300
ccggctgggt gtggcggacc gctatcagga catagcgttg gctacccgtg atattgctga  12360
agagcttggc ggcgaatggg ctgaccgctt cctcgtgctt tacggtatcg ccgctcccga  12420
ttcgcagcgc atcgccttct atcgccttct tgacgagttc ttctgaattt tgttaaaatt  12480
tttgttaaat cagctcattt tttaaccaat aggccgaaat cggcaacatc ccttataaat  12540
caaaagaata gaccgcgata gggttgagtg ttgttccagt ttggaacaag agtccactat  12600
taaagaacgt ggactccaac gtcaaagggc gaaaaaccgt ctatcagggc gatggcccac  12660
```

```
tacgtgaacc atcacccaaa tcaagttttt tgcggtcgag gtgccgtaaa gctctaaatc  12720

ggaaccctaa agggagcccc cgatttagag cttgacgggg aaagccggcg aacgtggcga  12780

gaaaggaagg gaagaaagcg aaaggagcgg gcgctagggc gctggcaagt gtagcggtca  12840

cgctgcgcgt aaccaccaca cccgcgcgct taatgcgccg nnnnnnn              12887


<210> SEQ ID NO 5
<211> LENGTH: 24
<212> TYPE: DNA
<213> ORGANISM: Artificial Sequence
<220> FEATURE:
<223> OTHER INFORMATION: Entirely synthesized

<400> SEQUENCE: 5

agccatgggc ccttggagcc gcag                                          24


<210> SEQ ID NO 6
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 6

ggaataaccc agtctctctt ctgtc                                         25


<210> SEQ ID NO 7
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 7

tgcggcccga agatgacatg aaacc                                         25


<210> SEQ ID NO 8
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 8

cccaggaggc tctcaggacc gctc                                          24


<210> SEQ ID NO 9
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 9

gaggaggctg cagcagcgga agac                                          24


<210> SEQ ID NO 10
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 10

gagccagcag gctgatgccc tcac                                          24
```

<210> SEQ ID NO 11
<211> LENGTH: 28
<212> TYPE: DNA
<213> ORGANISM: Artificial Sequence
<220> FEATURE:
<223> OTHER INFORMATION: Entirely Synthesized

<400> SEQUENCE: 11
ccttgcccaa aatcccctat gtcaaagc 28

<210> SEQ ID NO 12
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 12
gtatcgccaa tgccgcctga gacctc 26

<210> SEQ ID NO 13
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 13
attataaatc tagagactcc agg 23

<210> SEQ ID NO 14
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 14
catggaggaa ggaagaggag agac 24

<210> SEQ ID NO 15
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 15
ctgctgcctg aatgggggaa cctgc 25

<210> SEQ ID NO 16
<211> LENGTH: 27
<212> TYPE: DNA
<213> ORGANISM: Artificial Sequence
<220> FEATURE:
<223> OTHER INFORMATION: Entirely Synthesized

<400> SEQUENCE: 16
gccacgaggt gctcatccat cacaagg 27

<210> SEQ ID NO 17
<211> LENGTH: 24
<212> TYPE: DNA
<213> ORGANISM: Artificial Sequence
<220> FEATURE:

<223> OTHER INFORMATION: Entirely Synthesized

<400> SEQUENCE: 17
ttataaggcg gcgggggtgg tggc 24

<210> SEQ ID NO 18
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 18
cgaaggggaa cttgtccatc tccag 25

<210> SEQ ID NO 19
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 19
atcatccgca gcctacaggc ag 22

<210> SEQ ID NO 20
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 20
ctgtccctcc tgggcccgcc agg 23

<210> SEQ ID NO 21
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 21
cctgctcaag ctgactcgac accgtg 26

<210> SEQ ID NO 22
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 22
ggaaaagctg gccctggggt ggagc 25

<210> SEQ ID NO 23
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 23
ctcaaccagc agctcctaga aggg 24

<210> SEQ ID NO 24
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 24
gctggcccgc gcctggcagc tgc 23

<210> SEQ ID NO 25
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 25
cttatgctac gtaaaggagc tggg 24

<210> SEQ ID NO 26
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 26
gtgccaaccc aggtcccgga agtt 24

<210> SEQ ID NO 27
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 27
tgaaggtcgg agtcaacgga tttgg 25

<210> SEQ ID NO 28
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 28
ggaggccatg tgggccatga g 21

<210> SEQ ID NO 29
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 29
ctacaacgcc tacgagtcct acaag 25

<210> SEQ ID NO 30
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 30
gttgcaccag aaaagtcaga gttg 24

<210> SEQ ID NO 31
<211> LENGTH: 26
<212> TYPE: DNA
<213> ORGANISM: Artificial Sequence
<220> FEATURE:
<223> OTHER INFORMATION: Entirely Synthesized

<400> SEQUENCE: 31
aggagtccca ggacatcaaa gctctg 26

<210> SEQ ID NO 32
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 32
ccggcggcaa tagcatggcg agcgg 25

<210> SEQ ID NO 33
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 33
atatcccgcc gtgggtgaaa gttc 24

<210> SEQ ID NO 34
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 34
actcagccat ggactggagc atcc 24

<210> SEQ ID NO 35
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 35
tccaattcgc tgacccatcc tccg 24

<210> SEQ ID NO 36
<211> LENGTH: 28
<212> TYPE: DNA
<213> ORGANISM: Artificial Sequence
<220> FEATURE:
<223> OTHER INFORMATION: Entirely Synthesized

<400> SEQUENCE: 36
ccccaaagcc agaagatgca caaggagg 28

<210> SEQ ID NO 37
<211> LENGTH: 27

<212> TYPE: DNA
<213> ORGANISM: Artificial Sequence
<220> FEATURE:
<223> OTHER INFORMATION: Entirely Synthesized

<400> SEQUENCE: 37
cgtcgccaac catcttcctg tccctag 27

<210> SEQ ID NO 38
<211> LENGTH: 25
<212> TYPE: DNA
<213> ORGANISM: Artificial Sequence
<220> FEATURE:
<223> OTHER INFORMATION: Entirely Synthesized

<400> SEQUENCE: 38
atggtgaccg agctgctggg aggag 25

<210> SEQ ID NO 39
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 39
atacattgat gagtttggac aaac 24

<210> SEQ ID NO 40
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 40
gaggaggctg cagcagcgga agac 24

<210> SEQ ID NO 41
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 41
ccactaggca ggccgttagg ctgg 24

<210> SEQ ID NO 42
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 42
ggatacagca cagtaaggag c 21

<210> SEQ ID NO 43
<211> LENGTH: 19
<212> TYPE: DNA
<213> ORGANISM: Artificial Sequence
<220> FEATURE:
<223> OTHER INFORMATION: Entirely Synthesized

<400> SEQUENCE: 43
gcacagaccc acagttctc 19

<210> SEQ ID NO 44
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 44
tctcccatgc attcaaactg ag 22

<210> SEQ ID NO 45
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 45
cctttgtgtt cccaattcct tc 22

<210> SEQ ID NO 46
<211> LENGTH: 23
<212> TYPE: DNA
<213> ORGANISM: Artificial Sequence
<220> FEATURE:
<223> OTHER INFORMATION: Entirely Synthesized

<400> SEQUENCE: 46
cccgagactt atgctacgta aag 23

<210> SEQ ID NO 47
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 47
ggcagacagg ttaaagtaga gg 22

<210> SEQ ID NO 48
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 48
agctacaaac aggtgaagac c 21

<210> SEQ ID NO 49
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 49
gtggtaggaa gagtaaaggc tg 22

<210> SEQ ID NO 50
<211> LENGTH: 22
<212> TYPE: DNA
<213> ORGANISM: Artificial Sequence

```
<220> FEATURE:
<223> OTHER INFORMATION: Entirely Synthesized

<400> SEQUENCE: 50

gatgtggagt atgagagtga cg                                            22


<210> SEQ ID NO 51
<211> LENGTH: 19
<212> TYPE: DNA
<213> ORGANISM: Artificial Sequence
<220> FEATURE:
<223> OTHER INFORMATION: Entirely Synthesized

<400> SEQUENCE: 51

ggtcaagggt caggagttc                                                19


<210> SEQ ID NO 52
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 52

gcacggcttt tgttcagatg                                               20


<210> SEQ ID NO 53
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 53

cggttgaagg tgagactggc                                               20


<210> SEQ ID NO 54
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 54

caaggcaaag aatgaccgtt c                                             21


<210> SEQ ID NO 55
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 55

tgctgaattc ctggtatcgc                                               20


<210> SEQ ID NO 56
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 56

gcagaagcgc agatcaaaag                                               20
```

<210> SEQ ID NO 57
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 57
cggacatgag gctaccatat g 21

<210> SEQ ID NO 58
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 58
aggagtttca tccgaccaac 20

<210> SEQ ID NO 59
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 59
tctgccatta tccacataca gc 22

<210> SEQ ID NO 60
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 60
atcaacatcc acagcgagac 20

<210> SEQ ID NO 61
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 61
caaccatctt cctgtcccta g 21

<210> SEQ ID NO 62
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 62
ccatgaaggt cacccacttc 20

<210> SEQ ID NO 63
<211> LENGTH: 24
<212> TYPE: DNA
<213> ORGANISM: Artificial Sequence
<220> FEATURE:
<223> OTHER INFORMATION: Entirely Synthesized

<400> SEQUENCE: 63
ctcttgcatt aaactcttca tccg 24

<210> SEQ ID NO 64
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 64
cccagcgaag agaatgaaga g 21

<210> SEQ ID NO 65
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 65
aatggaacct gccttctcag 20

<210> SEQ ID NO 66
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 66
cccaatacat ctcccttcac ag 22

<210> SEQ ID NO 67
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 67
ccacctctaa ggccatcttt g 21

<210> SEQ ID NO 68
<211> LENGTH: 22
<212> TYPE: DNA
<213> ORGANISM: Artificial Sequence
<220> FEATURE:
<223> OTHER INFORMATION: Entirely Synthesized

<400> SEQUENCE: 68
gcgcacaatc attgagtttc tg 22

<210> SEQ ID NO 69
<211> LENGTH: 20
<212> TYPE: DNA
<213> ORGANISM: Artificial Sequence
<220> FEATURE:
<223> OTHER INFORMATION: Entirely Synthesized

<400> SEQUENCE: 69
agacaaacat gcccaggagg 20

<210> SEQ ID NO 70

<211> LENGTH: 23
<212> TYPE: DNA
<213> ORGANISM: Artificial Sequence
<220> FEATURE:
<223> OTHER INFORMATION: Entirely Synthesized

<400> SEQUENCE: 70
gaaggtgaag gtcggagtca acg 23

<210> SEQ ID NO 71
<211> LENGTH: 21
<212> TYPE: DNA
<213> ORGANISM: Artificial Sequence
<220> FEATURE:
<223> OTHER INFORMATION: Entirely Synthesized

<400> SEQUENCE: 71
gaagatggtg atgggatttc c 21

<210> SEQ ID NO 72
<211> LENGTH: 16309
<212> TYPE: DNA
<213> ORGANISM: artificial sequence
<220> FEATURE:
<223> OTHER INFORMATION: The pAdTrack adeno shuttle vector containing multi-reprogramming factors sequence has been provided as pAd-KcMOS.
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t
<220> FEATURE:
<221> NAME/KEY: misc_feature
<222> LOCATION: (355)..(357)
<223> OTHER INFORMATION: n is a, c, g, or t
<220> FEATURE:
<221> NAME/KEY: misc_feature
<222> LOCATION: (1945)..(1947)
<223> OTHER INFORMATION: n is a, c, g, or t
<220> FEATURE:
<221> NAME/KEY: misc_feature
<222> LOCATION: (7317)..(7317)
<223> OTHER INFORMATION: n is a, c, g, or t
<220> FEATURE:
<221> NAME/KEY: misc_feature
<222> LOCATION: (10202)..(10204)
<223> OTHER INFORMATION: n is a, c, g, or t
<220> FEATURE:
<221> NAME/KEY: misc_feature
<222> LOCATION: (12445)..(12447)
<223> OTHER INFORMATION: n is a, c, g, or t
<220> FEATURE:
<221> NAME/KEY: misc_feature
<222> LOCATION: (12462)..(12464)
<223> OTHER INFORMATION: n is a, c, g, or t
<220> FEATURE:
<221> NAME/KEY: misc_feature
<222> LOCATION: (13447)..(13449)
<223> OTHER INFORMATION: n is a, c, g, or t
<220> FEATURE:
<221> NAME/KEY: misc_feature
<222> LOCATION: (13464)..(13466)
<223> OTHER INFORMATION: n is a, c, g, or t
<220> FEATURE:
<221> NAME/KEY: misc_feature
<222> LOCATION: (14767)..(14772)
<223> OTHER INFORMATION: n is a, c, g, or t

<400> SEQUENCE: 72
nnnttaatta annntccctt ccagctctct gccccttttg gattgaagcc aatatgataa 60

```
tgagggggtg gagtttgtga cgtggcgcgg ggcgtgggaa cggggcgggt gacgtagtag    120

tgtggcggaa gtgtgatgtt gcaagtgtgg cggaacacat gtaagcgacg gatgtggcaa    180

aagtgacgtt tttggtgtgc gccggtgtac acaggaagtg acaattttcg cgcggtttta    240

ggcggatgtt gtagtaaatt tgggcgtaac cgagtaagat ttggccattt tcgcgggaaa    300

actgaataag aggaagtgaa atctgaataa ttttgtgtta ctcatagcgc gtaannncgc    360

gttaagatac attgatgagt ttggacaaac cacaactaga atgcagtgaa aaaaatgctt    420

tatttgtgaa atttgtgatg ctattgcttt atttgtaacc attataagct gcaataaaca    480

agttaacaac aacaattgca ttcattttat gtttcaggtt cagggggagg tgtgggaggt    540

tttttaaagc aagtaaaacc tctacaaatg tggtatggct gattatgatc agttatctag    600

atccggtgga tctgagtccg gacttgtaca gctcgtccat gccgagagtg atcccggcgg    660

cggtcacgaa ctccagcagg accatgtgat cgcgcttctc gttggggtct ttgctcaggg    720

cggactgggt gctcaggtag tggttgtcgg gcagcagcac ggggccgtcg ccgatggggg    780

tgttctgctg gtagtggtcg gcgagctgca cgctgccgtc ctcgatgttg tggcggatct    840

tgaagttcac cttgatgccg ttcttctgct tgtcggccat gatatagacg ttgtggctgt    900

tgtagttgta ctccagcttg tgccccagga tgttgccgtc ctccttgaag tcgatgccct    960

tcagctcgat gcggttcacc agggtgtcgc cctcgaactt cacctcggcg cgggtcttgt   1020

agttgccgtc gtccttgaag aagatggtgc gctcctggac gtagccttcg ggcatggcgg   1080

acttgaagaa gtcgtgctgc ttcatgtggt cggggtagcg gctgaagcac tgcacgccgt   1140

aggtcagggt ggtcacgagg gtgggccagg gcacgggcag cttgccggtg gtgcagatga   1200

acttcagggt cagcttgccg taggtggcat cgccctcgcc ctcgccggac acgctgaact   1260

tgtggccgtt tacgtcgccg tccagctcga ccaggatggg caccaccccg gtgaacagct   1320

cctcgccctt gctcaccatg gtggcgaccg gtagcgctag cggatctgac ggttcactaa   1380

accagctctg cttatataga cctcccaccg tacacgccta ccgcccattt gcgtcaatgg   1440

ggcggagttg ttacgacatt ttggaaagtc ccgttgattt tggtgccaaa acaaactccc   1500

attgacgtca atggggtgga gacttggaaa tccccgtgag tcaaaccgct atccacgccc   1560

attgatgtac tgccaaaacc gcatcaccat ggtaatagcg atgactaata cgtagatgta   1620

ctgccaagta ggaaagtccc ataaggtcat gtactgggca taatgccagg cgggccattt   1680

accgtcattg acgtcaatag ggggcgtact tggcatatga tacacttgat gtactgccaa   1740

gtgggcagtt taccgtaaat actccaccca ttgacgtcaa tggaaagtcc ctattggcgt   1800

tactatggga acatacgtca ttattgacgt caatgggcgg gggtcgttgg gcggtcagcc   1860

aggcgggcca tttaccgtaa gttatgtaac gcggaactcc atatatgggc tatgaactaa   1920

tgaccccgta attgattact attannncta gcagatctgg taccgtcgat aatagtaatc   1980

aattacgggg tcattagttc atagcccata tatggagttc cgcgttacat aacttacggt   2040

aaatggcccg cctggctgac cgcccaacga cccccgccca ttgacgtcaa taatgacgta   2100

tgttcccata gtaacgccaa tagggacttt ccattgacgt caatgggtgg agtatttacg   2160

gtaaactgcc cacttggcag tacatcaagt gtatcatatg ccaagtacgc cccctattga   2220

cgtcaatgac ggtaaatggc ccgcctggca ttatgcccag tacatgacct tatgggactt   2280

tcctacttgg cagtacatct acgtattagt catcgctatt accatggtga tgcggttttg   2340

gcagtacatc aatgggcgtg gatagcggtt tgactcacgg ggatttccaa gtctccaccc   2400
```

```
cattgacgtc aatgggagtt tgttttggca ccaaaatcaa cgggactttc caaaatgtcg   2460
taacaactcc gccccattga cgcaaatggg cggtaggcgt gtacggtggg aggtctatat   2520
aagcagagct ggtttagtga accgtcagat ccgctagcat ggctgtcagc gacgcgctgc   2580
tcccatcttt ctccacgttc gcgtctggcc cggcgggaag ggagaagaca ctgcgtcaag   2640
caggtgcccc gaataaccgc tggcgggagg agctctccca catgaagcga cttcccccag   2700
tgcttcccgg ccgcccctat gacctggcgg cggcgaccgt ggccacagac ctggagagcg   2760
gcggagccgg tgcggcttgc ggcggtagca acctggcgcc cctacctcgg agagagaccg   2820
aggagttcaa cgatctcctg gacctggact ttattctctc caattcgctg acccatcctc   2880
cggagtcagt ggccgccacc gtgtcctcgt cagcgtcagc ctcctcttcg tcgtcgccgt   2940
cgagcagcgg ccctgccagc gcgccctcca cctgcagctt cacctatccg atccgggccg   3000
ggaacgaccc gggcgtggcg ccgggcggca cgggcggagg cctcctctat ggcagggagt   3060
ccgctccccc tccgacggct cccttcaacc tggcggacat caacgacgtg agcccctcgg   3120
gcggcttcat ggccgagctc ctgcggccag aattggaccc ggtgtacatt ccgccgcagc   3180
agccgcagcc gccaggtggc gggctgatgg gcaagttcgt gctgaaggcg tcgctgagcg   3240
cccctggcag cgagtacggc agcccgtcgg tcatcagcgt cagcaaaggc agccctgacg   3300
gcagccaccc ggtggtggtg gcgccctaca acggcgggcc gccgcgcacg tgccccaaga   3360
tcaagcagga ggcggtctct tcgtgcaccc acttgggcgc tggacccccct ctcagcaatg   3420
gccaccggcc ggctgcacac gacttccccc tggggcggca gctccccagc aggactaccc   3480
cgaccctggg tcttgaggaa gtgctgagca gcagggactg tcaccctgcc ctgccgcttc   3540
ctcccggctt ccatccccac ccggggccca attacccatc cttcctgccc gatcagatgc   3600
agccgcaagt cccgccgctc cattaccaag agctcatgcc acccggttcc tgcatgccag   3660
aggagcccaa gccaaagagg ggaagacgat cgtggccccg gaaaaggacc gccacccaca   3720
cttgtgatta cgcgggctgc ggcaaaacct acacaaagag ttcccatctc aaggcacacc   3780
tgcgaaccca cacaggtgag aaaccttacc actgtgactg ggacggctgt ggatggaaat   3840
tcgcccgctc agatgaactg accaggcact accgtaaaca cacggggcac cgcccgttcc   3900
agtgccaaaa atgcgaccga gcattttcca ggtcggacca cctcgcctta cacatgaaga   3960
ggcattttta agctagcgct accggactca gatcggccgc gactctagat cataatcagc   4020
cataccacat ttgtagaggt tttacttgct ttaaaaaacc tcccacacct ccccctgaac   4080
ctgaaacata aaatgaatgc aattgttgtt gttaacttgt ttattgcagc ttataatggt   4140
tacaaataaa gcaatagcat cacaaatttc acaaataaag catttttttc actgcattct   4200
agttgtggtt tgtccaaact catcaatgta tcttaatcga cgcggcctaa tagtaatcaa   4260
ttacggggtc attagttcat agcccatata tggagttccg cgttacataa cttacggtaa   4320
atggcccgcc tggctgaccg cccaacgacc cccgcccatt gacgtcaata atgacgtatg   4380
ttcccatagt aacgccaata gggactttcc attgacgtca atgggtggag tatttacggt   4440
aaactgccca cttggcagta catcaagtgt atcatatgcc aagtacgccc cctattgacg   4500
tcaatgacgg taaatggccc gcctggcatt atgcccagta catgacctta tgggactttc   4560
ctacttggca gtacatctac gtattagtca tcgctattac catggtgatg cggttttggc   4620
agtacatcaa tgggcgtgga tagcggtttg actcacgggg atttccaagt ctccacccca   4680
ttgacgtcaa tgggagtttg ttttggcacc aaaatcaacg ggactttcca aaatgtcgta   4740
acaactccgc cccattgacg caaatgggcg gtaggcgtgt acggtgggag gtctatataa   4800
```

```
gcagagctgg tttagtgaac cgtcagatcc gctagcatgc ccctcaacgt tagcttcacc   4860
aacaggaact atgacctcga ctacgactcg gtgcagccgt atttctactg cgacgaggag   4920
gagaacttct accagcagca gcagcagagc gagctgcagc ccccggcgcc cagcgaggat   4980
atctggaaga aattcgagct gctgcccacc ccgcccctgt cccctagccg ccgctccggg   5040
ctctgctcgc cctcctacgt tgcggtcaca cccttctccc ttcggggaga caacgacggc   5100
ggtggcggga gcttctccac ggccgaccag ctggagatgg tgaccgagct gctgggagga   5160
gacatggtga accagagttt catctgcgac ccggacgacg agaccttcat caaaaacatc   5220
atcatccagg actgtatgtg gagcggcttc tcggccgccg ccaagctcgt ctcagagaag   5280
ctggcctcct accaggctgc gcgcaaagac agcggcagcc cgaaccccgc ccgcggccac   5340
agcgtctgct ccacctccag cttgtacctg caggatctga gcgccgccgc ctcagagtgc   5400
atcgacccct cggtggtctt cccctaccct ctcaacgaca gcagctcgcc caagtcctgc   5460
gcctcgcaag actccagcgc cttctctccg tcctcggatt ctctgctctc ctcgacggag   5520
tcctccccgc agggcagccc cgagcccctg gtgctccatg aggagacacc gcccaccacc   5580
agcagcgact ctgaggagga acaagaagat gaggaagaaa tcgatgttgt ttctgtggaa   5640
aagaggcagg ctcctggcaa aaggtcagag tctggatcac cttctgctgg aggccacagc   5700
aaacctcctc acagcccact ggtcctcaag aggtgccacg tctccacaca tcagcacaac   5760
tacgcagcgc ctccctccac tcggaaggac tatcctgctg ccaagagggt caagttggac   5820
agtgtcagag tcctgagaca gatcagcaac aaccgaaaat gcaccagccc caggtcctcg   5880
gacaccgagg agaatgtcaa gaggcgaaca cacaacgtct tggagcgcca gaggaggaac   5940
gagctaaaac ggagcttttt tgccctgcgt gaccagatcc cggagttgga aaacaatgaa   6000
aaggccccca aggtagttat ccttaaaaaa gccacagcat acatcctgtc cgtccaagca   6060
gaggagcaaa agctcatttc tgaagaggac ttgttgcgga aacgacgaga acagttgaaa   6120
cacaaacttg aacagctacg gaactcttgt gcgtaagcta gcgctaccgg actcagatcg   6180
gccgcgactc tagatcataa tcagccatac cacatttgta gaggttttac ttgctttaaa   6240
aaacctccca cacctccccc tgaacctgaa acataaaatg aatgcaattg ttgttgttaa   6300
cttgtttatt gcagcttata atggttacaa ataaagcaat agcatcacaa atttcacaaa   6360
taaagcattt ttttcactgc attctagttg tggtttgtcc aaactcatca atgtatctta   6420
aggccgcgat taatagtaat caattacggg gtcattagtt catagcccat atatggagtt   6480
ccgcgttaca taacttacgg taaatggccc gcctggctga ccgcccaacg acccccgccc   6540
attgacgtca ataatgacgt atgttcccat agtaacgcca atagggactt tccattgacg   6600
tcaatgggtg gagtatttac ggtaaactgc ccacttggca gtacatcaag tgtatcatat   6660
gccaagtacg ccccctattg acgtcaatga cggtaaatgg cccgcctggc attatgccca   6720
gtacatgacc ttatgggact ttcctacttg gcagtacatc tacgtattag tcatcgctat   6780
taccatggtg atgcggtttt ggcagtacat caatgggcgt ggatagcggt ttgactcacg   6840
gggatttcca agtctccacc ccattgacgt caatgggagt ttgttttggc accaaaatca   6900
acgggacttt ccaaaatgtc gtaacaactc cgccccattg acgcaaatgg gcggtaggcg   6960
tgtacggtgg gaggtctata taagcagagc tggtttagtg aaccgtcaga tccgctagca   7020
tggcgggaca cctggcttcg gatttcgcct tctcgccccc tccaggtggt ggaggtgatg   7080
ggccaggggg gccggagccg ggctgggttg atcctcggac ctggctaagc ttccaaggcc   7140
```

```
ctcctggagg gccaggaatc gggccggggg ttgggccagg ctctgaggtg tgggggattc   7200
ccccatgccc cccgccgtat gagttctgtg gggggatggc gtactgtggg ccccaggttg   7260
gagtggggct agtgccccaa ggcggcttgg agacctctca gcctgagggt gaagcangag   7320
tcggggtgga gagcaactcc gatggggcct ccccggagcc ctgcaccgtc accccctggtg  7380
ccgtgaagct ggagaaggag aagctggagc aaaacccgga ggagtcccag gacatcaaag   7440
ctctgcagaa agaactcgag caatttgcca agctcctgaa gcagaagagg atcaccctgg   7500
gatatacaca ggccgatgtg gggctcaccc tgggggttct atttgggaag gtattcagcc   7560
aaacgaccat ctgccgcttt gaggctctgc agcttagctt caagaacatg tgtaagctgc   7620
ggcccttgct gcagaagtgg gtggaggaag ctgacaacaa tgaaaatctt caggagatat   7680
gcaaagcaga aaccctcgtg caggcccgaa agagaaagcg aaccagtatc gagaaccgag   7740
tgagaggcaa cctggagaat ttgttcctgc agtgcccgaa acccacactg cagcagatca   7800
gccacatcgc ccagcagctt gggctcgaga aggatgtggt ccgagtgtgg ttctgtaacc   7860
ggcgccagaa gggcaagcga tcaagcagcg actatgcaca acgagaggat tttgaggctg   7920
ctgggtctcc tttctcaggg ggaccagtgt cctttcctct ggccccaggg ccccattttg   7980
gtaccccagg ctatgggagc cctcacttca ctgcactgta ctcctcggtc cctttccctg   8040
agggggaagc ctttcccccct gtctccgtca ccactctggg ctctcccatg cattcaaact  8100
gagctagcgc taccggactc agatcggccg cgactctaga tcataatcag ccataccaca   8160
tttgtagagg ttttacttgc tttaaaaaac ctcccacacc tcccccctgaa cctgaaacat  8220
aaaatgaatg caattgttgt tgttaacttg tttattgcag cttataatgg ttacaaataa   8280
agcaatagca tcacaaattt cacaaataaa gcattttttt cactgcattc tagttgtggt   8340
ttgtccaaac tcatcaatgt atcttaaatc ctcgagaagc ttaatagtaa tcaattacgg   8400
ggtcattagt tcatagccca tatatggagt tccgcgttac ataacttacg gtaaatggcc   8460
cgcctggctg accgcccaac gacccccgcc cattgacgtc aataatgacg tatgttccca   8520
tagtaacgcc aatagggact ttccattgac gtcaatgggt ggagtattta cggtaaactg   8580
cccacttggc agtacatcaa gtgtatcata tgccaagtac gccccctatt gacgtcaatg   8640
acggtaaatg gcccgcctgg cattatgccc agtacatgac cttatgggac tttcctactt   8700
ggcagtacat ctacgtatta gtcatcgcta ttaccatggt gatgcggttt tggcagtaca   8760
tcaatgggcg tggatagcgg tttgactcac ggggatttcc aagtctccac cccattgacg   8820
tcaatgggag tttgttttgg caccaaaatc aacgggactt tccaaaatgt cgtaacaact   8880
ccgccccatt gacgcaaatg ggcggtaggc gtgtacggtg ggaggtctat ataagcagag   8940
ctggtttagt gaaccgtcag atccgctagc atgtacaaca tgatggagac ggagctgaag   9000
ccgccgggcc cgcagcaaac ttcggggggc ggcggcggca actccaccgc ggcggcggcc   9060
ggcggcaacc agaaaaacag cccggaccgc gtcaagcggc ccatgaatgc cttcatggtg   9120
tggtcccgcg ggcagcggcg caagatggcc caggagaacc ccaagatgca caactcggag   9180
atcagcaagc gcctgggcgc cgagtggaaa cttttgtcgg agacggagaa gcggccgttc   9240
atcgacgagg ctaagcggct gcgagcgctg cacatgaagg agcacccgga ttataaatac   9300
cggccccggc ggaaaaccaa gacgctcatg aagaaggata agtacacgct gcccggcggg   9360
ctgctggccc ccggcggcaa tagcatggcg agcggggtcg gggtgggcgc cggcctgggc   9420
gcgggcgtga accagcgcat ggacagttac gcgcacatga acggctggag caacggcagc   9480
tacagcatga tgcaggacca gctgggctac ccgcagcacc cgggcctcaa tgcgcacggc   9540
```

```
gcagcgcaga tgcagcccat gcaccgctac gacgtgagcg ccctgcagta caactccatg   9600
accagctcgc agacctacat gaacggctcg cccacctaca gcatgtccta ctcgcagcag   9660
ggcacccctg gcatggctct tggctccatg ggttcggtgg tcaagtccga ggccagctcc   9720
agccccccctg tggttacctc ttcctcccac tccagggcgc cctgccaggc cggggacctc   9780
cgggacatga tcagcatgta tctccccggc gccgaggtgc cggaacccgc cgccccccagc   9840
agacttcaca tgtcccagca ctaccagagc ggcccggtgc ccggcacggc cattaacggc   9900
acactgcccc tctcacacat gtgagctagc gctaccggac tcagatcggc cgcgactcta   9960
gatcataatc agccatacca catttgtaga ggttttactt gctttaaaaa acctcccaca  10020
cctccccctg aacctgaaac ataaaatgaa tgcaattgtt gttgttaact tgtttattgc  10080
agcttataat ggttacaaat aaagcaatag catcacaaat ttcacaaata aagcattttt  10140
ttcactgcat tctagttgtg gtttgtccaa actcatcaat gtatcttaaa gctttctaga  10200
gnnntaaggg tgggaaagaa tatataaggt gggggtctta tgtagttttg tatctgtttt  10260
gcagcagccg ccgccgccat gagcaccaac tcgtttgatg gaagcattgt gagctcatat  10320
ttgacaacgc gcatgccccc atgggccggg gtgcgtcaga atgtgatggg ctccagcatt  10380
gatggtcgcc ccgtcctgcc cgcaaactct actaccttga cctacgagac cgtgtctgga  10440
acgccgttgg agactgcagc ctccgccgcc gcttcagccg ctgcagccac cgcccgcggg  10500
attgtgactg actttgcttt cctgagcccg cttgcaagca gtgcagcttc ccgttcatcc  10560
gcccgcgatg acaagttgac ggctcttttg gcacaattgg attctttgac ccgggaactt  10620
aatgtcgttt ctcagcagct gttggatctg cgccagcagg tttctgccct gaaggcttcc  10680
tcccctccca atgcggttta aaacataaat aaaaaaccag actctgtttg gatttggatc  10740
aagcaagtgt cttgctgtct ttatttaggg gttttgcgcg cgcggtaggc ccgggaccag  10800
cggtctcggt cgttgagggt cctgtgtatt ttttccagga cgtggtaaag gtgactctgg  10860
atgttcagat acatgggcat aagcccgtct ctggggtgga ggtagcacca ctgcagagct  10920
tcatgctgcg gggtggtgtt gtagatgatc cagtcgtagc aggagcgctg ggcgtggtgc  10980
ctaaaaatgt ctttcagtag caagctgatt gccaggggca ggcccttggt gtaagtgttt  11040
acaaagcggt taagctggga tgggtgcata cgtggggata tgagatgcat cttggactgt  11100
atttttaggt tggctatgtt cccagccata tccctccggg gattcatgtt gtgcagaacc  11160
accagcacag tgtatccggt gcacttggga aatttgtcat gtagcttaga aggaaatgcg  11220
tggaagaact tggagacgcc cttgtgacct ccaagatttt ccatgcattc gtccataatg  11280
atggcaatgg gcccacgggc ggcggcctgg gcgaagatat ttctgggatc actaacgtca  11340
tagttgtgtt ccaggatgag atcgtcatag gccattttta caaagcgcgg gcggagggtg  11400
ccagactgcg gtataatggt tccatccggc ccaggggcgt agttaccctc acagatttgc  11460
atttcccacg ctttgagttc agatgggggg atcatgtcta cctgcggggc gatgaagaaa  11520
acggtttccg ggtaggggga gatcagctgg gaagaaagca ggttcctgag cagctgcgac  11580
ttaccgcagc cggtgggccc gtaaatcaca cctattaccg ggtgcaactg gtagttaaga  11640
gagctgcagc tgccgtcatc cctgagcagg ggggccactt cgttaagcat gtccctgact  11700
cgcatgtttt ccctgaccaa atccgccaga aggcgctcgc cgcccagcga tagcagttct  11760
tgcaaggaag caaagttttt caacggtttg agaccgtccg ccgtaggcat gcttttgagc  11820
gtttgaccaa gcagttccag gcggtcccac agctcggtca cctgctctac ggcatctcga  11880
```

```
tccagcatat ctcctcgttt cgcgggttgg ggcggctttc gctgtacggc agtagtcggt  11940

gctcgtccag acgggccagg gtcatgtctt tccacgggcg cagggtcctc gtcagcgtag  12000

tctgggtcac ggtgaagggg tgcgctccgg gctgcgcgct ggccagggtg cgcttgaggc  12060

tggtcctgct ggtgctgaag cgctgccggt cttcgccctg cgcgtcggcc aggtagcatt  12120

tgaccatggt gtcatagtcc agcccctccg cggcgtggcc cttggcgcgc agcttgccct  12180

tggaggaggc gccgcacgag gggcagtgca gacttttgag ggcgtagagc ttgggcgcga  12240

gaaataccga ttccggggag taggcatccg cgccgcaggc cccgcagacg gtctcgcatt  12300

ccacgagcca ggtgagctct ggccgttcgg ggtcaaaaac caggtttccc ccatgctttt  12360

tgatgcgttt cttacctctg gtttccatga gccggtgtcc acgctcggtg acgaaaaggc  12420

tgtccgtgtc cccgtataca gactnnngtt taaacgaatt cnnntataaa atgcaaggtg  12480

ctgctcaaaa aatcaggcaa agcctcgcgc aaaaaagaaa gcacatcgta gtcatgctca  12540

tgcagataaa ggcaggtaag ctccggaacc accacagaaa aagacaccat ttttctctca  12600

aacatgtctg cgggtttctg cataaacaca aaataaaata acaaaaaaac atttaaacat  12660

tagaagcctg tcttacaaca ggaaaaacaa cccttataag cataagacgg actacggcca  12720

tgccggcgtg accgtaaaaa aactggtcac cgtgattaaa aagcaccacc gacagctcct  12780

cggtcatgtc cggagtcata atgtaagact cggtaaacac atcaggttga ttcatcggtc  12840

agtgctaaaa agcgaccgaa atagcccggg ggaatacata cccgcaggcg tagagacaac  12900

attacagccc ccataggagg tataacaaaa ttaataggag agaaaaacac ataaacacct  12960

gaaaaaccct cctgcctagg caaaatagca ccctcccgct ccagaacaac atacagcgct  13020

tcacagcggc agcctaacag tcagccttac cagtaaaaaa gaaaacctat taaaaaaaca  13080

ccactcgaca cggcaccagc tcaatcagtc acagtgtaaa aaagggccaa gtgcagagcg  13140

agtatatata ggactaaaaa atgacgtaac ggttaaagtc cacaaaaaac acccagaaaa  13200

ccgcacgcga acctacgccc agaaacgaaa gccaaaaaac ccacaacttc ctcaaatcgt  13260

cacttccgtt ttcccacgtt acgtaacttc ccattttaag aaaactacaa ttcccaacac  13320

atacaagtta ctccgcccta aaacctacgt cacccgcccc gttcccacgc cccgcgccac  13380

gtcacaaact ccaccccctc attatcatat tggcttcaat ccaaaataag gtatattatt  13440

gatgatnnnt taattaagga tccnnnncggt gtgaaatacc gcacagatgc gtaaggagaa  13500

aataccgcat caggcgctct tccgcttcct cgctcactga ctcgctgcgc tcggtcgttc  13560

ggctgcggcg agcggtatca gctcactcaa aggcggtaat acggttatcc acagaatcag  13620

gggataacgc aggaaagaac atgtgagcaa aaggccagca aaaggccagg aaccgtaaaa  13680

aggccgcgtt gctggcgttt ttccataggc tccgcccccc tgacgagcat cacaaaaatc  13740

gacgctcaag tcagaggtgg cgaaacccga caggactata aagataccag gcgtttcccc  13800

ctggaagctc cctcgtgcgc tctcctgttc cgaccctgcc gcttaccgga tacctgtccg  13860

cctttctccc ttcgggaagc gtggcgcttt ctcatagctc acgctgtagg tatctcagtt  13920

cggtgtaggt cgttcgctcc aagctgggct gtgtgcacga accccccgtt cagcccgacc  13980

gctgcgcctt atccggtaac tatcgtcttg agtccaaccc ggtaagacac gacttatcgc  14040

cactggcagc agccactggt aacaggatta gcagagcgag gtatgtaggc ggtgctacag  14100

agttcttgaa gtggtggcct aactacggct acactagaag gacagtattt ggtatctgcg  14160

ctctgctgaa gccagttacc ttcggaaaaa gagttggtag ctcttgatcc ggcaaacaaa  14220

ccaccgctgg tagcggtggt ttttttgttt gcaagcagca gattacgcgc agaaaaaaag  14280
```

```
gatctcaaga agatcctttg atcttttcta cggggtctga cgctcagtgg aacgaaaact  14340

cacgttaagg gattttggtc atgagattat caaaaaggat cttcacctag atccttttaa  14400

attaaaaatg aagttttaaa tcaatctaaa gtatatatga gtaaacttgg tctgacagtt  14460

accaatgctt aatcagtgag gcacctatct cagcgatctg tctatttcgt tcatccatag  14520

ttgcctgact ccccgtcgtg tagataacta cgatacggga gggcttacca tctggcccca  14580

gtgctgcaat gataccgcga gacccacgct caccggctcc agatttatca gcaataaacc  14640

agccagccgg aagggccgag cgcagaagtg gtcctgcaac tttatccgcc tccatccagt  14700

ctattaattg ttgccgggaa gctagagtaa gtagttcgcc agttaatagt ttgcgcaacg  14760

ttgttgnnnn nnaaaaagga tcttcaccta gatccttttc acgtagaaag ccagtccgca  14820

gaaacggtgc tgaccccgga tgaatgtcag ctactgggct atctggacaa gggaaaacgc  14880

aagcgcaaag agaaagcagg tagcttgcag tgggcttaca tggcgatagc tagactgggc  14940

ggttttatgg acagcaagcg aaccggaatt gccagctggg gcgccctctg gtaaggttgg  15000

gaagccctgc aaagtaaact ggatggcttt ctcgccgcca aggatctgat ggcgcagggg  15060

atcaagctct gatcaagaga caggatgagg atcgtttcgc atgattgaac aagatggatt  15120

gcacgcaggt tctccggccg cttgggtgga gaggctattc ggctatgact gggcacaaca  15180

gacaatcggc tgctctgatg ccgccgtgtt ccggctgtca gcgcaggggc gcccggttct  15240

ttttgtcaag accgacctgt ccggtgccct gaatgaactg caagacgagg cagcgcggct  15300

atcgtggctg gccacgacgg gcgttccttg cgcagctgtg ctcgacgttg tcactgaagc  15360

gggaagggac tggctgctat tgggcgaagt gccggggcag gatctcctgt catctcacct  15420

tgctcctgcc gagaaagtat ccatcatggc tgatgcaatg cggcggctgc atacgcttga  15480

tccggctacc tgcccattcg accaccaagc gaaacatcgc atcgagcgag cacgtactcg  15540

gatggaagcc ggtcttgtcg atcaggatga tctggacgaa gagcatcagg ggctcgcgcc  15600

agccgaactg ttcgccaggc tcaaggcgag catgcccgac ggcgaggatc tcgtcgtgac  15660

ccatggcgat gcctgcttgc cgaatatcat ggtggaaaat ggccgctttt ctggattcat  15720

cgactgtggc cggctgggtg tggcggaccg ctatcaggac atagcgttgg ctacccgtga  15780

tattgctgaa gagcttggcg gcgaatgggc tgaccgcttc ctcgtgcttt acggtatcgc  15840

cgctcccgat tcgcagcgca tcgccttcta tcgccttctt gacgagttct tctgaatttt  15900

gttaaaattt ttgttaaatc agctcatttt ttaaccaata ggccgaaatc ggcaacatcc  15960

cttataaatc aaaagaatag accgcgatag ggttgagtgt tgttccagtt tggaacaaga  16020

gtccactatt aaagaacgtg gactccaacg tcaaagggcg aaaaaccgtc tatcagggcg  16080

atggcccact acgtgaacca tcacccaaat caagtttttt gcggtcgagg tgccgtaaag  16140

ctctaaatcg gaaccctaaa gggagccccc gatttagagc ttgacgggga aagccggcga  16200

acgtggcgag aaaggaaggg aagaaagcga aaggagcggg cgctagggcg ctggcaagtg  16260

tagcggtcac gctgcgcgta accaccacac ccgcgcgctt aatgcgccg             16309
```